US007566770B2

(12) United States Patent
Watkins et al.

(10) Patent No.: US 7,566,770 B2
(45) Date of Patent: Jul. 28, 2009

(54) HUMANIZED COLLAGEN ANTIBODIES AND RELATED METHODS

(75) Inventors: Jeffry D. Watkins, Encinitas, CA (US); William D. Huse, Del Mar, CA (US); Ying Tang, San Diego, CA (US); Daniel Broek, Los Angeles, CA (US); Peter Brooks, Carmel, NY (US)

(73) Assignee: Cell-Matrix, Inc., Bethesda, MD (US)

( * ) Notice: Subject to any disclaimer, the term of this patent is extended or adjusted under 35 U.S.C. 154(b) by 0 days.

(21) Appl. No.: 11/486,894

(22) Filed: Jul. 14, 2006

(65) Prior Publication Data

US 2007/0077199 A1    Apr. 5, 2007

Related U.S. Application Data

(60) Division of application No. 10/011,250, filed on Dec. 6, 2001, now Pat. No. 7,390,885, which is a continuation-in-part of application No. 09/995,529, filed on Nov. 26, 2001, now Pat. No. 7,365,167.

(51) Int. Cl.
  *C07K 16/00* (2006.01)
(52) U.S. Cl. .................. 530/387.1; 424/130.1
(58) Field of Classification Search ........................ None
  See application file for complete search history.

(56) References Cited

U.S. PATENT DOCUMENTS

| | | | |
|---|---|---|---|
| 4,342,566 | A | 8/1982 | Theofilopoulos et al. |
| 4,604,463 | A | 8/1986 | Miyasaka et al. |
| 5,092,885 | A | 3/1992 | Yamada et al. |
| 5,112,946 | A | 5/1992 | Maione |
| 5,192,744 | A | 3/1993 | Bouck et al. |
| 5,202,352 | A | 4/1993 | Okada et al. |
| 5,223,409 | A | 6/1993 | Ladner et al. |
| 5,264,563 | A | 11/1993 | Huse |
| 5,320,970 | A | 6/1994 | Eyre |
| 5,403,484 | A | 4/1995 | Ladner et al. |
| 5,464,826 | A | 11/1995 | Grindey et al. |
| 5,465,826 | A | 11/1995 | Noestheden |
| 5,523,388 | A | 6/1996 | Huse |
| 5,530,101 | A | 6/1996 | Queen et al. |
| 5,541,295 | A | 7/1996 | Barrach et al. |
| 5,565,332 | A | 10/1996 | Hoogneboom et al. |
| 5,693,762 | A | 12/1997 | Queen et al. |
| 5,763,272 | A | 6/1998 | Naser et al. |
| 5,817,699 | A | 10/1998 | Flores et al. |
| 5,869,045 | A | 2/1999 | Hellstrom et al. |
| 5,871,974 | A | 2/1999 | Huse |
| 5,912,366 | A | 6/1999 | Weigel |
| 5,972,623 | A | 10/1999 | Krane et al. |
| 6,001,994 | A | 12/1999 | Weigel |
| 6,030,792 | A | 2/2000 | Otterness et al. |
| 6,132,976 | A | 10/2000 | Poole et al. |
| 6,521,593 | B1 | 2/2003 | Laug |
| 6,849,599 | B2 | 2/2005 | Calabresi et al. |
| 2003/0099655 | A1 | 5/2003 | Watkins |
| 2003/0113331 | A1 | 6/2003 | Brooks |
| 2004/0091482 | A9 | 5/2004 | Watkins |

FOREIGN PATENT DOCUMENTS

| | | |
|---|---|---|
| DE | 4127790 A1 | 2/1993 |
| EP | 0510949 B2 | 10/1992 |
| EP | 0921395 | 6/1999 |
| EP | 0528767 B1 | 1/2000 |
| EP | 0992586 | 4/2000 |
| JP | 2005-347062 | 12/2005 |
| JP | 06-075216 | 3/2006 |
| WO | WO94/14070 | 6/1994 |
| WO | WO95/04282 | 2/1995 |
| WO | WO95/11015 A1 | 4/1995 |
| WO | WO96/06636 A1 | 3/1996 |
| WO | WO97/39746 A1 | 10/1997 |
| WO | WO97/44059 | 11/1997 |
| WO | WO97/48418 A1 | 12/1997 |
| WO | WO98/33919 A2 | 8/1998 |
| WO | WO98/35235 | 8/1998 |
| WO | WO99/06834 A2 | 2/1999 |
| WO | WO99/06840 | 2/1999 |
| WO | WO99/11208 A1 | 3/1999 |
| WO | WO00/23593 A2 | 4/2000 |
| WO | WO00/40597 A1 | 7/2000 |
| WO | WO00/78815 A1 | 12/2000 |
| WO | WO01/04157 A2 | 1/2001 |
| WO | WO01/27160 A1 | 4/2001 |
| WO | WO01/57226 A1 | 8/2001 |

OTHER PUBLICATIONS

Borza et al. J. of Biological Chemistry, vol. 275, No. 8, pp. 6030-6037, 2000.*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology. (2002) 320, 415-428.*
Chen et al. J. Mol. Bio. (1999) 293, 865-881.*
Wu et al. J. Mol. Biol. (1999) 294, 151-162.*
Holm et al. Molecular Immunology, (2007) 44, 1075-1084.*
Mueller et al. PNAS vol. 89 pp. 11832-11836, Dec. 1992.*

(Continued)

*Primary Examiner*—Larry R. Helms
*Assistant Examiner*—Meera Natarajan
(74) *Attorney, Agent, or Firm*—Wilson Sonsini Goodrich & Rosati

(57) ABSTRACT

The invention provides an antibody, or functional fragment thereof, a grafted antibody, or functional fragment thereof, comprising one or more complementarity determining regions (CDRs) having at least one amino acid substitution in one or more CDRs of a heavy chain CDR, where the antibody or functional fragment thereof has specific binding activity for a cryptic collagen epitope. The invention also provides methods of using an antibody having specific binding activity for a cryptic collagen epitope, including methods of inhibiting angiogenesis, tumor growth, and metastasis.

11 Claims, 20 Drawing Sheets

OTHER PUBLICATIONS

Xu et al. Hybridoma. vol. 19(5) pp. 375-385, Oct. 2000.*
Bowei, J. et al., "Deciphering the message in protein sequences: tolerance to amino acids subsitutions," Science 247(4948):1306-1310 (1990).
Brooks, P.C. et al., "Localization of matrix metalloproteinase MMP-2 to the surface of invasive cells by interaction with integrin αvβ3," Cell 85:683-693 (1996).
Brooks, P.C. et al., "Ionizing radiation modulates the exposure of the HUIV26 cryptic epitope within collagen Type IV during angiogenesis," Int. J. Radiation Oncol. Biol. Phys. 54(4):1194-1201 (2002).
Freimark et al., "Targeting of humanized antibody D93 to sites of angiogenesis and tumor growth by binding to multiple epitopes on denatured collagens," Molecular Immunology, doi.10.1016/j.molimm.2007.03.027 (2007).
Gussow, D. and Seemann, G., "Humanization of monoclonal antibodies," Methods Enzmol. 203:99-121 (1991).
Jo, N. et al., "Inhibitory effect of an antibody to cryptic collagen Type IV epitopes on choroidal neovascularization," Molecular Vision 12:1243-1249 (2006).
Krauer et al., "Antitumor Effect of 2'-Deoxy-5-fluorouridine Conjugates against a Murine Thymoma and Colon Carcinoma Xenografts," Cancer Res. 52:132-137 (1992).
Lopez-Requena et al., "Gangliosides, Ab1 and Ab2 antibodies II. Light versus heavy chain: An idiotype anti-idiotype case study," Mol. Immunol. 44:1015-1028 (2007).
PCT/US07/014001 Partial Search Report dated Feb. 2, 2008.
Pernasetti et al., "Novel anti-denatured collagen humanized antibody D93 inhibits angiogenesis and tumor growth: An extracellular matrix based therapeutic approach," Int. J. Oncol. 29:1371-1379 (2006).
Roth, J. et al., "Inhibition of Experimental Metastasis by Targeting the HUIV26 Cryptic Epitope in Collagen," Am. J. Pathol. 168(5):1576-1586 (2006).
Winkler, K. et al., "Changing the Antigen Binding Specificity by Single Point Mutations of an Anti-p24 (HVI-1) Antibody," J. Immunol. 165:4505-4514 (2000).
Borza et al., "The Goodpasture Autoantigen," J. Biol. Chem. Feb. 25, 2000;275(8):6030-7.
Caldas et al., "Humanization of the anti-CD18 antibody 6.7: an unexpected effect of a framework residue in binding to antigen," Molecular Immunology 39 (2003) 941-952.
Chien et al., "Significant structural and functional change of an antigen-binding site by a distant amino acid substitution: Proposal of a structural mechanism," PNAS USA vol. 86, pp. 5532-5536, Jul. 1989.
David et al., "Hydrophobic Amino Acid Residues Are Critical for the Immunodominant Epitope of the Goodpasture Autoantigen," J. Biol. Chem. Mar. 2, 2001;276(9):6370-7.
Giusti et al., "Somatic diversification of S107 from an antiphosphocholine to an anti-DNA autoantibody is due to a single base change in its heavy hain variable region," PNAS USA vol. 84, pp. 2926-2930, May 1987.
Greenspan et al., "Defining epitopes: It's not as easy as it seems," Nat. Biotech. Oct. 1999;17:936-7.
Kalluri et al., "Specificity of Circulating and Tissue-Bound Antibodies in Goodpasture Syndrome," Proc. Assoc. Am. Physicians Mar. 1996;108(2):134-9.
Mariuzza et al., "The Structural Basis of Antigen-Antibody Recognition," Ann. Rev.Biophys. Biophys. Chem. 1987;16:139-59.
Nakanishi et al., "Immunohistochemical study of ∞1-5 chains of type IV collagen in hereditary nephritis," Kidney Int. 1994;46:1413-21.
Wheatcroft et al., "Evidence of in situ stability of the type IV collagen triple helix in human inflammatory bowel disease using a denaturation specific epitope antibody," Matrix Biol. 18 (1999):361-372.
Yang et al., "CDR Walking Mutagenesis for the Affinity Maturation of a Potent Human Anti-HIV-1 Antibody into the Picomolar Range," J. Mol. Biol. Dec. 1, 1995;254(3):392-403.
Yoshioka et al., "Type IV Collagen ∞6 Chain, Normal Distribution and Abnormalities in X-Linked Alport Syndrome Revealed by Monoclonal Antibody," Am. J. Pathol. 1994;144:986-96.

Hangai, M. et al., "Angiogenic cryptic site of proteolyzed subendothelial type IV collagen as a novel target to treat retinal neovascularization," IOVS 41(4):S641 (2000) (Abstract).
EP 0279569.2 Supplemental Search Report dated Apr. 24, 2007.
U.S. Appl. No. 10/011,250, filed Dec. 6, 2001, Watkins et al.
Amstutz et al., "In vitro display technologies: novel developments and applications," Curr. Op. in Biotech. 2001:12:400-405.
Ausprunk et al., "Vascularization of Normal and Neoplastic Tissues Grafted to the Chick Chorioallontois," Am. J. Pathol. 79:597-618 (1975).
Blood, C.H. and Zetter, B.R., Tumor interactions with the vasculature: angiogenesis and tumor metastasis, Biochim. Biophys. Acta. 1032:89-118 (1995).
Brooks et al., "Subtractive Immunization Yields Monoclonal Antibodies that Specifically Inhibit Metastasis," J. Cell Biol. 122:1351-1359 (1993).
Brooks et al., Integrin αvβ3 Antagonists Promote Tumor Regression by Inducing Aopotosis of Angiogenic Blood Vessels, Cell 79:1157-1164 (1994).
Brooks et al., "Localization of Matrix Metalloproteinase MMP-2 to the Surface of Invasive Cells by Interaction with Integrin αvβ3," Cell 85:683-693 (1996).
Brooks et al., "Disruption of Angiogenesis by PEX, a Noncatalytic Metalloproteinase Fragment with Integrin Binding Activity," Cell 92:391-400 (1998).
Chothia and Lesk, "Canonical Structures for the Hypervariable REgions of Immunoglobins," J. Mol. Biol. 196:901-917 (1987).
"Cancer Management: A Multidisciplinary Approach (Medical, Surgical, and Radiation Oncology)" eds. Pazdur R; Coia Lr, Hoskins WJ, Wagman LD (2000) Publisher RRR, Melville, NY, pp. 984-988.
Davis, George E., "Affinity of integrins for damaged extracellular matrix: alpha v β3 binds to denatured collagen type I through RGD sites", Biochem. & Biophysical Res. Communications, vol. 182, No. 3, pp. 1025-1031, 1992.
De Haard, et al., "A Large Non-immunized Human Fab Fragment Phage Library That Permits Rapid Isolation and Kinetic Analysis of High Affinity Antibodies," J. Biol. Chem. 274:18218-18230 (1999).
Dulbecco et al., "Placque Production by the Polyoma Virus," Virology 8:396-397, 1959.
Engel, J., "Versatile collagens in invertebrates," Science (1997) 277:1785-1786.
Fields, S. and Song, O., "A novel genetic system to detect protein-protein interactions," Nature 340:245-246 (1989).
Folkman, J. and Ingber, D., "Inhibition of angiogenesis," Cancer Biology 3:89-96 (1992).
Glaser et al., "Antibody Engineering by Condon-Based Mutagenesis in a Filamentous Phage Vector System," J. Immun. 149(12):3903-3913 (1992).
Gordon, M.K. and Olsen, B.R., "The contribution of collagenous proteins to tissue-specific matrix assemblies," Curr. Op. in Cell Biol. (1990) 2:833-838.
Green et al., PNAS USA 2003:100L1010-1015.
Guo et al., "In vitro evolution of amphioxus insulin-like pepetide to mammalian insulin," Biochem. 2002:41:10603-10607.
Haar, Ernst ter, "Taxanes and other microtubule stablilising agents," Expert Opinion on Therapeutic Patents 8(5):571-586 (1998).
Gutheil, John C., et al., "Targeted Antiangiogenic Therapy for Cancer Using Vitaxin: A Humanized Monoclonal Antibody to the Integrin ∞vβ31," Clinical Cancer Research vol. 6, pp. 3056-3061, Aug. 2000.
Hangai et al., "Matrix metallaproteinase-9-dependent exposure of a cryptic migratory control site in collagen is required before retinal angiogenesis," Am. J. of Path. 2002; 161(4):1429-1437.
Heeley, R.P., "Mutations Flanking the Polyglutamine Repeat in the Modulatory Domain of Rat Glucocorticoid Receptor in Lead to an Increase in Affinity for Hormone," Endocrine Res. 2002;28:217-229.
Herbst, Roy S. and Sandler, Alan B., "Non-Small Cell Lung Cancer and Antiangiogenic Therapy: What Can Be Expected of Bevacizumab?" The Oncologist 2004;9(Suppl 1):19-26.
Huse et al., "Generation of a Large Combinatorial Library of the Immunoglobulin Repertoire in Phage Lambda," Science 246:1275-1281 (1989).

Huse et al., "Application of a Filamentous Phage pVIII Fusion Protein System Suitable for Efficient Production, Screening and Mutagenesis of F(ab) Antibody Fragments," J. Immun. 149(12):3914-3920 (1992).

Ingber. D. and Folkman, J., "Inhibition of Angiogenesis Through Modulation of Collagen Metabolism," Lab. Invest. 59:44-51 (1988).

Ingham et al., "Type I collagen contains at least 14 cryptic fibronectin binding sites of similar affinity," Arch. Of Biochem. And Biophys. (2002) 407:217-223.

Inoue, K. et al., "Treatment of Human Metastatic Transitional Cell Carcinoma of the Bladder in a Murine Model with the Anti-Vascular Endothelial Growth Factor Receptor Monclonal Antibody DC101 and Paclitaxel," Clinical Cancer Res. vol. 6, 2635-2643, Jul. 2000.

Kabat et al., "Unusual Distributions of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616 (1977).

Kabat et al., "Sequences of Proteins of Immunological Interest," U.S. Dept. of Health and Human Services (1991).

Kaye, J., Clinical Oncology 12, 1527 (1994).

Kristensson et al., "Humanization of a Murine Antibody Against *Cryptococcus neoformans* Polysaccharide Using a Novel Approach," Vaccines 94, pp. 38-43, Cold Spring Harbor Laboratory, Cold Spring Harbor (1995).

Kohler and Milstein, "Continuous cultures of fused cells secreting antibodiy of predefined specificity," Nature 256:495-497 (1975).

Kucharz, E.J., "The Collagens: Biochemistry and Pathophysiology," Springer-Verlag, Berlin (1992).

Kunkel, "Rapid and Efficient Site-Specific Mutagenesis without Phenotype Selection," PNAS USA 82(2):488-492 (1985).

Kunn, K. in Structure and Function of Collagen Types, eds. R. Mayne and R.E. Burgeson, Academic Press, Orlando (1987).

Liljeblad et al., "Analysis of agalacto-IgG in rheumatoid arthritis using surface plasmon resonance," Glycoconjugate Journal 2000;17:323-329.

Lowman, H.B. et al., "Selecting High-Affinity Binding Proteins by Monovalent Phage Display," Biochemistry 30:10832-10838 (1991).

MacCallum et al., "Antibody-antigen interactions: contact analysis and binding site topography," J. Mol. Biol. 262:732-745 (1996).

Margolin et al., "Phase Ib Trial of Intravenous Recombinant Humanized Monoclonal Antibody to Vascular Endothelial Growth Factor in Comination with Chemotherapy in Patients with Advanced Cancer Pharmacologic and long-Term Safety Data," J. of Clin. Onc., vol. 19, No. 3 (Feb. 1, 2001), pp. 851-856.

Moses et al., "Identification of an Inhibitor of Neovascularization from Cartilage," Science 248:1408-1410 (1990).

Olsen, B.R., "New insights into the function of collagens from genetic analysis," Curr. Op. Cell Biol. 7, pp. 720-727 (1995).

Ossowski, L. and Reich, E., "Experimental Model for Quantitative Study of Metastasis," Cancer Research 40:2300-2309 (1980).

Petty, R. et al., "Antibodies to Type IV Collagen in Rheumatic Diseases," J. of Rheumatology 13:246-253 (1986).

Plunkett et al., Nucleosides Nucleotides 8, 775 (1989).

Receptor Binding Techniques, Methods in MOlecular Biology, 106 ed. M. Keen, Humana Press 1999.

Rugo, Hope S., "Bevacizumab in the Treatment of Breast Cancer: Rationale and Current Data," The Oncologist 2004; 9(suppl 1):43-49.

Sastry et al., "Cloning of the immunological repertoire in *Escherichia coli* for generation of monoclonal catalytic antibodies: Construction of a heavy chain variable region-specific cDNA library," PNAS USA 86:5728-5732 (1989).

Steffenson et al., "Human fibronection and MMp-2 collagen binding domains compete for collagen binding sites and modify cellular activation of MMp-2," Matrix Biol. (2002) 21:399-414.

Stephanopoulos, G., "Metabolic engineering by genome shuffling," Nature Biotech. (2002) 20(7):666-668.

Sweeney, C.J. et al., "The Antiangiogenic Property of Docetaxel is Synergistic with a Recombinant Humanized Monoclonal Antibody against Vascular Endothelial Growth Factor or 2-Methoxyestradiol byt Antagonized by Endothelial Growth Factors," Cancer Research 61, 3369-3372, Apr. 15, 2001.

Syrigos, K.N. and Epenetos, A., "Antibody Directed Enzyme Prodrug Therapy (ADEPT): A Review of the Experimental and Clinical Considerations," Anticancer Research 19:605-613 (1999).

Tani et al., "In vitro selection of fibronectin againof-function mutations," Biochem. J. (2002) 365:287-294.

Tennant et al., "Angiogensis Inhibitors," Curr. Onc. Reports 2:Jan. 11-16, 2000.

Van Der Rest, M. and Garrone, R., "Collagen family of proteins," FASEB 5, 2814-2823 (1991).

Varner et al., "Review: The Integrin $\alpha v\beta 3$: Angiogenesis and Apoptosis," Cell Adh. Commun. 3, pp. 367-374 (1995).

Wall, S. et al., "Meeting Report Proteases, Extracellular Matrix, and Cancer: An AACR Special Conference in Cancer Research," Cancer Research 63, 4750-4755, Aug. 1, 2003.

Watkins et al., "Determination of the Relative Affinities of Antibody Fragments Expressed in *Escherichia coli* by Enzyme-Linkied Immunosorbent Assay," Anal. Biochem. 253:37-45 (1997).

Watkins et al., "Engineering IgM Antibodies for Therapeutic Applications," IBC Antibody Engineering Conference, San Diego, Dec. 2-6, 2001, Presented Dec. 3, 2001.

Weidner et al., "Tumor Angiogenesis and Metastasis—Correlation in Invasive Breast Carncinoma," N. Engl. J. Med. 324:1-7 (1991).

Weidner et al., "Tumor Angiogenesis: A New Significant and Independent Prognostic Indicator in Early-Stage Breast Carcinoms," J. National Cancer Institute 84:1875-1887 (1992).

Wilder, R.L., "Integrin alpha V beta 3 as a target for treatment of rhematoid arthritis and related rheumatic diseases," Ann. Rheum. Dis 2002:61;96-99.

Winter et al., "Making Antibodies by Phage Display Technology," Annual Rev. Immunology 12:433-455 (1994).

Wu et al., "Stepwise in virto affinity maturation of Vitaxin, an $\infty v\beta 3$-specific humanized mAB," PNAS USA 95:6037-6042 (1998).

Wu et al., "Humanization of a Murine Monoclonal Antibody by Simultaneous Optimization of Framework and CDR Residues," J. Mol. Biol. 294:151-162 (1999).

Xu et al., "Proteolytic exposure of a cryptic site within collagen type IV is required for angiogenesis and tumor growth in vivo," J. Cell Biol. 154(5):1069-1079 (2001).

Yan et al., "Human/Severe Combined Immunodeficient Mouse Chimeras," J. Clin. Invest. 91:986-996 (1993).

Zhao et al., "Directed evolution of enzymes and pathways for industrial biocatalysis," Curr. Op. in Biotech. (2002) 13:104-110.

Zola, "Monoclonal Antibodies: A Manual of Techniques," CRC Press, Inc. (1987).

Timpl, R., "Antibodies to Collagens and Precollagens," Methods in Enzymology 82 Pt. A: 472-498 (1982).

Jellinek et al., "Inhibition of Receptor Binding by High-Affinity RNA Ligands to Vascular Endothelial Growth Factor," Biochemistry 33(34):10450-6 (1994).

Tuerk, C. et al., "Systematic Evolution of Ligands by Exponential Enrichment: RNA Ligands to Bacteriophage T4 DNA Polymerase," Science 249:505-510 (1990).

Ecker, D. et al., "Rational Screening of Oligonucleotide Combinatorial Libraries for Drug Discovery," Nucleic Acids Res. 21(8):1853-1856 (1993).

Wick, G. et al., "Characterization of Antibodies to Basement Membrane (Type IV) Collagen in Immunohistological Studies," Immunobiol. 156:372-381 (1979).

Petitclerc, E. et al., "Integrin alpha(v)beta3 promotes M21 Melanoma Growth in Human Skin by Regulating Tumor Cell Survival," Cancer Res. 59(11):2724-2730 (1999).

Borza, D. et al., "Identification of Multiple Cryptic Epitopes on the NC1 Domain of the a3(IV) Collagen Chain," J. Biol. Chem. 275(8):6030-6037 (2000).

Xu, J. et al., "Generation of Monoclonal Antibodies to Cryptic Collagen Sites by Using Subtractive Immunization," Hybridoma 19:375-385 (2000).

Bellon, G., Quantification and Specific Detection of Collagenous Proteins Using an Enzyme-Linked Immunosorbent Assay and an Immunoblotting for Cyanogen Bromide Peptides, Anal. Biochem. 150:188-202 (1985).

Brooks et al., "Antiintegrin αvβ3 blocks human breast cancer growth and angiogenesis in human skin," J. Clin. Invest. 96:1815-1822 (1995).

Aboud-Pirak et al., "Cytotoxic Activity of Daunorubicin or Vindesin Conjugated to a Monoclonal Antibody on Cultured MCF-7 Breast Carcinoma Cells," Biochem. Pharmacol. 38:641-648 (1989).

Dillman et al., "Significance of antigen, drug, and tumor cell targets in the preclinical evaluation of doxorubicin, methotrexate, and mitomycin-C monoclonal antibody immunoconjugates," Mol. Biother. 1:250-255 (1989).

Fitzpatrick, John J. and Garnett, Martin C., "Studies on the mechanism of action of an MTX-HSA-MoAb conjugate," Anti-Cancer Drug Des. 10:11-24 (1995).

Henn et al., "Synthesis of 2'-Deoxyuridine and 5-Fluoro-2'-deoxyuridine Derivatives and Evaluation in Antibody Targeting Studies," J. Med. Chem. 36:1570-1579 (1993).

Johnson, Kenneth A., "Advances in transient-state kinetics," Curr. Op. Biotech. 9:87-89(1998).

Jonsson, Ulf and Malmquist, Magnus, "Real Time Biospecific Interaction Analysis," Advances in Biosensors 2:291-336(1992).

Krauer, Kenia G. et al, "Antitumor Effect of 2'-Deoxy-5-fluorouridine Conjugates against a Murine Thymoma and Colon Carcinoma Xenografts," Cancer Res. 52:132-137 (1992).

Lau, A. et al., "Conjugation of Doxorubicin to Monoclonal Anticarcinoembryonic Antigen Antibody via Novel Thiol-directed Cross-linking Reagents," Bioorg.Med.Chem. 3:1299-1304 (1995).

Myszka, David. G. et al., "Extending the Range of Rate Constants from BIACORE: Interpreting Mass Transport-Influenced Binding Data," Biophys.J. 75:5830594 (1998).

Pluckthun, A. and Skerra, A., "Expression of Functional Antibody Fv and Fab Fragments in *Escherichia coli*," Meth. Enzymol. 178:497-515(1989).

Rich, Rebecca L. and Myszka, David G., "Advances in surface plasmon resonance biosensor analysis," Curr.Op. Biotech. 11:54-61 (2000).

Rowland, A.J. et al., "Preclinical investigation of the antitumor effects of anti-CD 19-idarubicin immunoconjugates," Cancer Immunol. Immunother. 37:195-202 (1993).

Schechter, B. et al., "Indirect Immunotargeting of CIS-PT to Human Epidermoid Carcinoma KB Using The Avidin-Biotin System," Int. J. Cancer 48:167-172 (1991).

Shawler, Daniel L. et al., "Preclinical Trials Using an Immunoconjugate of T101 and Methotrexate in an Athymic Mouse/Human T-Cell Tumor Model," J. Biol. Resp. Mod. 7:608-618 (1988).

Shih, Lisa B. et al., "Internalization of intact doxorubicin immunoconjugate," Cancer Immunol. Immunother. 38:92-98 (1994).

Sivam, Gowsala P. et al., "Therapeutic Efficacy of a Doxorubicin Immunoconjugate in a Preclinical Model of Spontaneous Metastatic Human Melanoma," Cancer Res. 55:2352-2356(1995).

Smyth, Mark J. et al., "The cellular uptake and cytotoxicity of chlorambucil-monoclonal antibody conjugates," Immunol. Cell Biol. 65:315-321 (1987).

Starling, James J. et al., "In Vivo Antitumor Activity of a Panel of Four Monoclonal Antibody-Vinca Alkaloid Immunoconjugates Which Bind To Three Distinct Epitopes of Carcinoembryonic Antigen," Bioconj. Chem. 3:315-322 (1992).

Ward, E. Sally et al., "Binding activities of a repertoire of single immunoglobulin variable domains secreted from *Escherichia coli*," Nature 341:544-546 (1989).

Winter. Greg and Harris, William J., "Humanized Antibodies," Immunol. Today 14:243-246(1993).

* cited by examiner

A

| Oilgo # | Name | Primer Sequences (5'-3') |
|---|---|---|
| 2663 | mK1 | TTG GTG CTG ATG TTC TGG |
| 2664 | mK2 | ATC TTC TTG CTG TTC TGG |
| 2665 | mK3 | TGG GTG CTG CTG CTC TGG |
| 2666 | mK4 | GGG CTG CTT GTG CTC TGG |
| 2667 | mK5 | GGA ATC TTG TTG CTC TGG |
| 2668 | mK6 | RTR TTS CTG CTG CTR TGG |
| 2669 | mK7 | GGT CTC CTG TTG CTC TGT |
| 2670 | mK8 | ATA TTT CTA CTG CTC TGT |
| 2671 | mK9 | GTC ATA ATR TCC AGA GGA |

B

| Oilgo # | Name | Primer Sequences (5'-3') |
|---|---|---|
| 2672 | mH1 | CTG AGC TGT GTA TTC CT |
| 2673 | mH2 | CTC ARM TTG ATT TTC CT |
| 2674 | mH3 | TGG RTC ATS TTC TTC CT |
| 2675 | mH4 | TKS RTC TTT CTC TTC CT |
| 2676 | mH5 | TGT ATC ATS CTC TTC TT |
| 2677 | mH6 | TGG RTC TTT CTC TTT TT |
| 2678 | mH7 | TTA AAC TGG GTT TTT CT |
| 2679 | mH8 | GKG CTG YTC YTC TGC CT |
| 2680 | mH9 | TTA AGT CTT CTG TAC CTG |
| 2730 | MH11 | TCAGTAACTGCAGGTGTCCA |
| 2731 | MH12 | TTTTAAAAGGTGTCCAGTGT |
| 2732 | MH13 | GCAACAGCTACAGGTGTCCA |
| 2733 | MH14 | CAGCTACAGRTGTCCACTCC |
| 2734 | MH15 | ATTTCCAAGCTGTGTCCTGTCC |
| 2735 | MH16 | CTCCTGTCAGGAACTGCAGGTGT |
| 2736 | MH17 | CAGTGGTTACAGGGGTCAATTCA |
| 2737 | MH18 | CTGTTSACAGCCHTTCCKGGT |
| 2738 | MH19 | CTGATGGCAGCTGCCCAAAGT |
| 2739 | MH20 | TTTATCAAGGTGTGCATTGT |

C
2650  5' TCACTGGATGGTGGGAAGATGGATACA 3'
2656  5' GACATTTGGGAAGGACTGACTCTC 3'
2706  5' CAG GGG GCT CTC GCA GGA GAC GAG 3'

FIGURE 1

HuIV-26 VL

```
GACATTGTGATGACACAGTCTCCATCTTTGTTGAGTGTGTCAGCAGGAGAGAAGGTCACT
ATGAGCTGCAAGTCCAGTCAGAGTCTGTTAAACAGTGGAAATCAAAAGAACTACTTGGCC
TGGTACCAGCAGAAACCAGGGCAGCCTCCTAAACTGTTGATCTATGGGGCATCCACTAGG
GAATCTGGGGTCCCTGATCGCTTCACAGGCAGTGGATCTGGAACCGATTTCACTCTTATC
ATCAGCAGTGTGCAGGCTGAAGACCTGGCAGTTTATTACTGTCAGAATGATCATAGTTAT
CCGTACACGTTCGGAGGGGGGACCAAGCTGGAAATAAAA
```

FIGURE 2A

HuIV-26 VH

GAGGTGAAGCTTCTCGAGTCTGGAGGTGGCCTGGTGCAGCCTGGAGGATCCCTGAAACT
CTCCTGTGCAGCCTCAGGATTCGATTTTAGTAGATACTGGATGAGTTGGGTCCGGCAGG
CTCCAGGGAAAGGGCTAGAATGGATTGGAGAAATTAATCCAGATAGCAGTACGATAAAC
TATACGCCATCTCTAAAGGATAAATTCATCATCTCCAGAGACAACGCCAAAAATACGCT
GTACCTGCAAATGAGCAAAGTGAGATCTGAGGACACAGCCCTTTATTACTGTGCAAGAC
CGGTTGATGGTTACTACGATGCTATGGACTACTGGGGTCAAGGAACCTCAGTCACCGTC
TCCTCA

FIGURE 2B

Vκ Domain

```
              1            10            20    abcdef   30           40
HUIV26        DIVMTQSPSLLSVSAGEKVTMSCKSSQSLLNSGNQKNYLAWYQQKPGQPPKLLIY
VKIV          DIVMTQSPDSLAVSLGERATINCKSSQSVLYSSNNKNYLAWYQQKPGQPPKLLIY 50           60            70            80            90          100
HUIV26        GASTRESGVPDRFTGSGSGTDFTLIISSVQAEDLAVYYCQNDHSYPYTFGGGTKLEIK
VKIV/JK2      WASTRESGVPDRFSGSGSGTDFTLTISSLQAEDVAVYYCQQDHSYPYTFGQGTKLEIK
```

V_H Domain

```
              1            10            20           30       abc   40
HUIV26        EVKLLESGGGLVQPGGSLKLSCAAASGFDFSRYWMSWVRQAPGKGLEWIG
VHIII         EVQLVESGGGLVQPGGSLRLSCAAASGFTFSSYWMSWVRQAPGKGLEWVA 50 a         60            70            80  abc       90
HUIV26        EINPDSSTINYTPSLKDKFIISRDNAKNTLYLQMSKVRSEDTALYYCAR
VHIII         NIKQDGSEKYYVDSVKGRFTISRDNAKNSLYLQMNSLRAEDTAVYYCAR abc
                    100            110
HUIV26        PVDGYYDAMDYWGQGTSVTVSS
JH6           PDYYYYYGMDVWGQGTTVTVSS
```

FIGURE 2C

HUI77 VL sequence

```
GATGTTTTGATGACCCAAACTCCACTCTCCCTGCCTGTCAGTCTTGGAGATCAAGCCTCC
ATCTCTTGCAGATCTAGTCAGAGCATTGTACATAGTAATGGAAACACCTATTTAGAATGG
TACCTGCAGAAACCAGGCCAGTCTCCAAAGCTCCTGATCTACAAAGTTTCCAACCGATTT
TCTGGTGTCCCAGACAGGTTCAGTGGCAGTGGATCAGGGACAGATTTCACACTCAAGATC
AGCAGAGTGGAGGCTGAGGATCTGGGAGTTTATTACTGCTTTCAAGGTTCACATGTTCCG
TGGACGTTCGGTGGAGGCACCAAGCTGGAAATCAAA
```

FIGURE 3A

HUI77 VH SEQUENCE

CAGGTTACTCTGAAAGAGACTGGCCCTGGGATATTGCAGCCCTCCCAGACCCTCAGTCTG
ACTTGTTCTTTCTCTGGGTTTTCACTGAGCACTTCTGGTATGGGTGTAGGCTGGATTCGT
CAGCCTTCAGGAGAGGGTCTAGAGTGGCTGGCAGACATTTGGTGGGATGACAATAAGTAC
TATAACCCATCCCTGAAGAGCCGGCTCACAATCTCCAAGGATACCTCCAGCAACCAGGTA
TTCCTCAAGATCACCAGTGTGGACACTGCAGATACTGCCACTTACTACTGTGCTCGAAGA
GCTAACTATGGTAACCCCTACTATGCTATGGACTACTGGGGTCAAGGAACCTCAGTCACC
GTCTCCTCA

FIGURE 3B

Vκ Domain

```
            1           10            20       abcde  30              40
HUI-77    DVLMTQTPLSLPVSLGDQASISCRSSQSIVHSNGNTYLEWYLQKPGQSPKLLIY
VKII      DIVMTQTPLSLPVTPGEPASISCRSSQSLLDSDGNTYLDWYLQKPGQSPQLLIY 50           60            70            80           90          100
HUI-77    KVSNRFSGVPDRFSGSGSGTDFTLKISRVEAEDLGVYYCFQGSHVPWTFGGGTKLEIK
VKII/JK1  TLSYRASGVPDRFSGSGSGTDFTLKISRVEAEDVGVYYCMQGSHVPWTFGQGTKVEIK
```

V_H Domain

```
            1           10            20          30  ab         40
HUI-77    QVTLKETGPGILQPSQTLSLTCSFSGFSLSTSGMGVGWIRQPSGEGLEWLA
VHII      QVTLKESGPALVKPTQTLTLTCTFSGFSLSTSGMRVSWIRQPPGKALEWLA 50           60            70        80  abc          90
HUI-77    DIWDDDNKYYNPSLKSRLTISKDTSSNQVFLKITSVDTADTATYYCAR
VHII      RIDWDDDKFYSTSLKTRLTISKDTSKNQVVLTMTNMDPVDTATYYCAR 100cde        110
HUI-77    RANYGNPYYAMDYWGQGTSVTVSS
JH6       RANYYYYYAMDVWGQGTTVTVSS
```

FIGURE 3C

HUI77 VL sequence

```
            1   2   3   4   5   6   7   8   9   10  11  12  13  14  15
HUI77 VL   GAT GTT TTG ATG ACC CAA ACT CCA CTC TCC CTG CCT GTC AGT CTT
DPK13      --- A-- G-- --- --- --G --- --- --- --- --- --C --- -CC -C-

_____CDR1_____
           16  17  18  19  20  21  22  23  24  25  26  27  27a 27b 27c
HUI77 VL   GGA GAT CAA GCC TCC ATC TCT TGC AGA TCT AGT CAG AGC ATT GTA
DPK13      --- --G -CG --- --- --- --C --- --G --- --- --- --- C-C T-G 27d 27e 27f 28  29  30  31  32  33  34  35  36  37  38  39
HUI77 VL   CAT AGT ... AAT GGA AAC ACC TAT TTA GAA TGG TAC CTG CAG AAA
DPK13      G-- --- GAT G-- --- --- --- --- --G --C --- --- --- --- --G

_____CDR2_____
           40  41  42  43  44  45  46  47  48  49  50  51  52  53  54
HUI77 VL   CCA GGC CAG TCT CCA AAG CTC CTG ATC TAC AAA GTT TCC AAC CGA
DPK13      --- --G --- --- --- C-- --- --- --- --T -CG C-- --- T-T --G 55  56  57  58  59  60  61  62  63  64  65  66  67  68  69
HUI77 VL   TTT TCT GGT GTC CCA GAC AGG TTC AGT GGC AGT GGA TCA GGG ACA
DPK13      GCC --- --A --- --- --- --- --- --- --- --- --G --- --C --T 70  71  72  73  74  75  76  77  78  79  80  81  82  83  84
HUI77 VL   GAT TTC ACA CTC AAG ATC AGC AGA GTG GAG GCT GAG GAT CTG GGA
DPK13      --- --- --- --G --A --- --- --G --- --- --- --- --- G-T ---

_____CDR3_____
           85  86  87  88  89  90  91  92  93  94  95  96  97  98  99
HUI77 VL   GTT TAT TAC TGC TTT CAA GGT TCA CAT GTT CCG TGG ACG TTC GGT
DPK13      --- --- --- --- A-G --- --- --- --- --- --- --- --- --- --C 100 101 102 103 104 105 106 107
HUI77 VL   GGA GGC ACC AAG CTG GAA ATC AAA
JK1        CA- --G --- --- G-- --- --- ---
```

FIGURE 3D

HUIV26 LCDR3

IV26-l7.1 CTT GGT CCC CTG GCC AAA AGT GTA CGG ATA ACT ATG ATC ATT MNN ACA GTA ATA AAC TGC CAC ATC
IV26-l7.2 CTT GGT CCC CTG GCC AAA AGT GTA CGG ATA ACT ATG ATC MNN CTG ACA GTA ATA AAC TGC CAC ATC
IV26-l7.3 CTT GGT CCC CTG GCC AAA AGT GTA CGG ATA ACT ATG MNN ATT CTG ACA GTA ATA AAC TGC CAC ATC
IV26-l7.4 CTT GGT CCC CTG GCC AAA AGT GTA CGG ATA ACT MNN ATC ATT CTG ACA GTA ATA AAC TGC CAC ATC
IV26-l7.5 CTT GGT CCC CTG GCC AAA AGT GTA CGG ATA MNN ATG ATC ATT CTG ACA GTA ATA AAC TGC CAC ATC
IV26-l7.6 CTT GGT CCC CTG GCC AAA AGT GTA CGG MNN ACT ATG ATC ATT CTG ACA GTA ATA AAC TGC CAC ATC
IV26-l7.7 CTT GGT CCC CTG GCC AAA AGT GTA MNN ATA ACT ATG ATC ATT CTG ACA GTA ATA AAC TGC CAC ATC
IV26-l7.8 CTT GGT CCC CTG GCC AAA AGT MNN CGG ATA ACT ATG ATC ATT CTG ACA GTA ATA AAC TGC CAC ATC
IV26-l7.9 CTT GGT CCC CTG GCC AAA MNN GTA CGG ATA ACT ATG ATC ATT CTG ACA GTA ATA AAC TGC CAC ATC

HUIV26 HCDR3

IV26-h7.1 CGT GGT TCC TTG CCC CCA GTA GTC CAT AGC ATC GTA GTA ACC ATC AAC MNN TCT CGC ACA GTA ATA CAC
IV26-h7.2 CGT GGT TCC TTG CCC CCA GTA GTC CAT AGC ATC GTA GTA ACC ATC MNN CGG TCT CGC ACA GTA ATA CAC
IV26-h7.3 CGT GGT TCC TTG CCC CCA GTA GTC CAT AGC ATC GTA GTA ACC MNN AAC CGG TCT CGC ACA GTA ATA CAC
IV26-h7.4 CGT GGT TCC TTG CCC CCA GTA GTC CAT AGC ATC GTA GTA MNN ATC AAC CGG TCT CGC ACA GTA ATA CAC
IV26-h7.5 CGT GGT TCC TTG CCC CCA GTA GTC CAT AGC ATC GTA MNN ACC ATC AAC CGG TCT CGC ACA GTA ATA CAC
IV26-h7.6 CGT GGT TCC TTG CCC CCA GTA GTC CAT AGC ATC MNN GTA ACC ATC AAC CGG TCT CGC ACA GTA ATA CAC
IV26-h7.7 CGT GGT TCC TTG CCC CCA GTA GTC CAT AGC MNN GTA GTA ACC ATC AAC CGG TCT CGC ACA GTA ATA CAC
IV26-h7.8 CGT GGT TCC TTG CCC CCA GTA GTC CAT MNN ATC GTA GTA ACC ATC AAC CGG TCT CGC ACA GTA ATA CAC
IV26-h7.9 CGT GGT TCC TTG CCC CCA GTA GTC MNN AGC ATC GTA GTA ACC ATC AAC CGG TCT CGC ACA GTA ATA CAC
IV26-h7.10 CGT GGT TCC TTG CCC CCA GTA MNN CAT AGC ATC GTA GTA ACC ATC AAC CGG TCT CGC ACA GTA ATA CAC
IV26-h7.11 CGT GGT TCC TTG CCC CCA MNN GTC CAT AGC ATC GTA GTA ACC ATC AAC CGG TCT CGC ACA GTA ATA CAC

FIGURE 4A

HUIV26 LCDR1a

| | |
|---|---|
| IV26L1-1 | GTTCTTTTGGTTTCCGCWGTTTAACAGACTCTGGCTGGAMNNGCAGTTGATGGTGGCCCT |
| IV26L1-2 | GTTCTTTTGGTTTCCGCWGTTTAACAGACTCTGGCTMNNCTTGCAGTTGATGGTGGCCCT |
| IV26L1-3 | GTTCTTTTGGTTTCCGCWGTTTAACAGACTCTGMNNGGACTTGCAGTTGATGGTGGCCCT |
| IV26L1-4 | GTTCTTTTGGTTTCCGCWGTTTAACAGACTMNNGCTGGACTTGCAGTTGATGGTGGCCCT |
| IV26L1-5 | GTTCTTTTGGTTTCCGCWGTTTAACAGMNNCTGGCTGGACTTGCAGTTGATGGTGGCCCT |
| IV26L1-6 | GTTCTTTTGGTTTCCGCWGTTTAAMNNACTCTGGCTGGACTTGCAGTTGATGGTGGCCCT |
| IV26L1-7 | GTTCTTTTGGTTTCCGCWGTTMNNCAGACTCTGGCTGGACTTGCAGTTGATGGTGGCCCT |
| IV26L1-8 | GTTCTTTTGGTTTCCGCWMNNTAACAGACTCTGGCTGGACTTGCAGTTGATGGTGGCCCT |

HUIV26 LCDR1b

| | |
|---|---|
| IV26L1-9 | TGGTTTCTGCTGGTACCAAGCTAAGTAGTTCTTTTGGTTTCCMNNGTTTAACAGACTCTGGCT |
| IV26L1-10 | TGGTTTCTGCTGGTACCAAGCTAAGTAGTTCTTTTGGTTMNNGCWGTTTAACAGACTCTGGCT |
| IV26L1-11 | TGGTTTCTGCTGGTACCAAGCTAAGTAGTTCTTTTGMNNTCCGCWGTTTAACAGACTCTGGCT |
| IV26L1-12 | TGGTTTCTGCTGGTACCAAGCTAAGTAGTTCTTMNNGTTTCCGCWGTTTAACAGACTCTGGCT |
| IV26L1-13 | TGGTTTCTGCTGGTACCAAGCTAAGTAGTTMNNTTGGTTTCCGCWGTTTAACAGACTCTGGCT |
| IV26L1-14 | TGGTTTCTGCTGGTACCAAGCTAAGTAMNNCTTTTGGTTTCCGCWGTTTAACAGACTCTGGCT |
| IV26L1-15 | TGGTTTCTGCTGGTACCAAGCTAAMNNGTTCTTTTGGTTTCCGCWGTTTAACAGACTCTGGCT |
| IV26L1-16 | TGGTTTCTGCTGGTACCAAGCMNNGTAGTTCTTTTGGTTTCCGCWGTTTAACAGACTCTGGCT |
| IV26L1-17 | TGGTTTCTGCTGGTACCAMNNTAAGTAGTTCTTTTGGTTTCCGCWGTTTAACAGACTCTGGCT |

HUIV26 LCDR2

| | |
|---|---|
| IV26L2-1 | GAATCGGTCAGGGACCCCGGATTCCCTGGTAGATGCMNNGTAAATGAGCAGCTTAGG |
| IV26L2-2 | GAATCGGTCAGGGACCCCGGATTCCCTGGTAGAMNNCCCGTAAATGAGCAGCTTAGG |
| IV26L2-3 | GAATCGGTCAGGGACCCCGGATTCCCTGGTMNNTGCCCCGTAAATGAGCAGCTTAGG |
| IV26L2-4 | GAATCGGTCAGGGACCCCGGATTCCCTMNNAGATGCCCCGTAAATGAGCAGCTTAGG |
| IV26L2-5 | GAATCGGTCAGGGACCCCGGATTCMNNGGTAGATGCCCCGTAAATGAGCAGCTTAGG |
| IV26L2-6 | GAATCGGTCAGGGACCCCGGAMNNCCTGGTAGATGCCCCGTAAATGAGCAGCTTAGG |
| IV26L2-7 | GAATCGGTCAGGGACCCCMNNTTCCCTGGTAGATGCCCCGTAAATGAGCAGCTTAGG |

HUIV26 HCDR1

| | |
|---|---|
| IV26H1-1 | TGGAGCCTGGCGGACCCAGCTCATCCAATAMNNACTAAAGGTGAATCCAGA |
| IV26H1-2 | TGGAGCCTGGCGGACCCAGCTCATCCAMNNTCTACTAAAGGTGAATCCAGA |
| IV26H1-3 | TGGAGCCTGGCGGACCCAGCTCATMNNATATCTACTAAAGGTGAATCCAGA |
| IV26H1-4 | TGGAGCCTGGCGGACCCAGCTMNNCCAATATCTACTAAAGGTGAATCCAGA |
| IV26H1-5 | TGGAGCCTGGCGGACCCAMNNCATCCAATATCTACTAAAGGTGAATCCAGA |

HUIV26 HCDR2a

| | |
|---|---|
| IV26H2-1 | TAGAGATGGCGTATAGTTTATCGTACTGCTATCTGGATTTATMNNGCCAAYCCACTCCAGCCCTTTC |
| IV26H2-2 | TAGAGATGGCGTATAGTTTATCGTACTGCTATCTGGATTMNNTCGCCAAYCCACTCCAGCCCTTTC |
| IV26H2-3 | TAGAGATGGCGTATAGTTTATCGTACTGCTATCTGGMNNTATTTCGCCAAYCCACTCCAGCCCTTTC |
| IV26H2-4 | TAGAGATGGCGTATAGTTTATCGTACTGCTATCMNNATTTATTTCGCCAAYCCACTCCAGCCCTTTC |
| IV26H2-5 | TAGAGATGGCGTATAGTTTATCGTACTGCTMNNTGGATTTATTTCGCCAAYCCACTCCAGCCCTTTC |
| IV26H2-6 | TAGAGATGGCGTATAGTTTATCGTACTMNNATCTGGATTTATTTCGCCAAYCCACTCCAGCCCTTTC |
| IV26H2-7 | TAGAGATGGCGTATAGTTTATCGTMNNGCTATCTGGATTTATTTCGCCAAYCCACTCCAGCCCTTTC |
| IV26H2-8 | TAGAGATGGCGTATAGTTTATMNNACTGCTATCTGGATTTATTTCGCCAAYCCACTCCAGCCCTTTC |
| IV26H2-9 | TAGAGATGGCGTATAGTTMNNCGTACTGCTATCTGGATTTATTTCGCCAAYCCACTCCAGCCCTTTC |

HUIV26 HCDR2b

| | |
|---|---|
| IV26H2-10 | CGTTGTCTCTGGAGATGRTGAATYTATCCTTTAGAGATGGCGTATAMNNTATCGTACTGCTATCTGG |
| IV26H2-11 | CGTTGTCTCTGGAGATGRTGAATYTATCCTTTAGAGATGGCGTMNNGTTTATCGTACTGCTATCTGG |
| IV26H2-12 | CGTTGTCTCTGGAGATGRTGAATYTATCCTTTAGAGATGGMNNATAGTTTATCGTACTGCTATCTGG |
| IV26H2-13 | CGTTGTCTCTGGAGATGRTGAATYTATCCTTTAGAGAMNNCGTATAGTTTATCGTACTGCTATCTGG |
| IV26H2-14 | CGTTGTCTCTGGAGATGRTGAATYTATCCTTTAGMNNTGGCGTATAGTTTATCGTACTGCTATCTGG |
| IV26H2-15 | CGTTGTCTCTGGAGATGRTGAATYTATCCTTMNNAGATGGCGTATAGTTTATCGTACTGCTATCTGG |
| IV26H2-16 | CGTTGTCTCTGGAGATGRTGAATYTATCMNNTAGAGATGGCGTATAGTTTATCGTACTGCTATCTGG |
| IV26H2-17 | CGTTGTCTCTGGAGATGRTGAATYTMNNCTTTAGAGATGGCGTATAGTTTATCGTACTGCTATCTGG |

FIGURE 4B

Beneficial Mutations for HuIV-26 Antibody

| CDRs | H1 | | | H2 | | | | H3 | | | L1 | | | | | L2 | L3 | |
|---|---|---|---|---|---|---|---|---|---|---|---|---|---|---|---|---|---|---|
| Kabat Number | 31 | 34 | 35 | 57 | 62 | 64 | 65 | 97 | 98 | 102 | 27 | 27d | 27e | 27f | 29 | | 93 | 94 |
| HuIV-26 | R | M | S | I | S | K | D | D | G | Y | Q | N | S | G | Q | | S | Y |
| Mutations | H | I | T | A | Y | Q | S | P | P | P | R | S | Y | Y | K | | Q | N |
| | | | A | S | A | | | G | A | N | S | | W | R | | | G | S |
| | | | G | | H | | | T | H | | | | H | H | | | L | P |
| | | | | | G | | | A | | | | | R | I | | | A | M |
| | | | | | | | | | | | | | | | | | T | |
| | | | | | | | | | | | | | | | | | V | |

FIGURE 4C

HUI77 LCDR3
177-l7.1   CTT GGT GCC CTG GCC GAA CGT CCA CGG AAC ATG TGA ACC TTG MNN GCA GTA ATA AAC TCC AAC ATC
177-l7.2   CTT GGT GCC CTG GCC GAA CGT CCA CGG AAC ATG TGA ACC MNN AAA GCA GTA ATA AAC TCC AAC ATC
177-l7.3   CTT GGT GCC CTG GCC GAA CGT CCA CGG AAC ATG TGA MNN TTG AAA GCA GTA ATA AAC TCC AAC ATC
177-l7.4   CTT GGT GCC CTG GCC GAA CGT CCA CGG AAC ATG MNN ACC TTG AAA GCA GTA ATA AAC TCC AAC ATC
177-l7.5   CTT GGT GCC CTG GCC GAA CGT CCA CGG AAC MNN TGA ACC TTG AAA GCA GTA ATA AAC TCC AAC ATC
177-l7.6   CTT GGT GCC CTG GCC GAA CGT CCA CGG MNN ATG TGA ACC TTG AAA GCA GTA ATA AAC TCC AAC ATC
177-l7.7   CTT GGT GCC CTG GCC GAA CGT CCA MNN AAC ATG TGA ACC TTG AAA GCA GTA ATA AAC TCC AAC ATC
177-l7.8   CTT GGT GCC CTG GCC GAA CGT MNN CGG AAC ATG TGA ACC TTG AAA GCA GTA ATA AAC TCC AAC ATC
177-l7.9   CTT GGT GCC CTG GCC GAA MNN CCA CGG AAC ATG TGA ACC TTG AAA GCA GTA ATA AAC TCC AAC ATC

HUI77 HCDR3
177-h7.1    CGT GGT TCC TTG CCC CCA GTA GTC CAT AGC ATA GTA GGG GTT ACC ATA GTT AGC MNN TCG AGC ACA GTA ATA CGT
177-h7.2    CGT GGT TCC TTG CCC CCA GTA GTC CAT AGC ATA GTA GGG GTT ACC ATA GTT MNN TCT TCG AGC ACA GTA ATA CGT
177-h7.3    CGT GGT TCC TTG CCC CCA GTA GTC CAT AGC ATA GTA GGG GTT ACC ATA MNN AGC TCT TCG AGC ACA GTA ATA CGT
177-h7.4    CGT GGT TCC TTG CCC CCA GTA GTC CAT AGC ATA GTA GGG GTT ACC MNN GTT AGC TCT TCG AGC ACA GTA ATA CGT
177-h7.5    CGT GGT TCC TTG CCC CCA GTA GTC CAT AGC ATA GTA GGG GTT MNN ATA GTT AGC TCT TCG AGC ACA GTA ATA CGT
177-h7.6    CGT GGT TCC TTG CCC CCA GTA GTC CAT AGC ATA GTA GGG MNN ACC ATA GTT AGC TCT TCG AGC ACA GTA ATA CGT
177-h7.7    CGT GGT TCC TTG CCC CCA GTA GTC CAT AGC ATA GTA MNN GTT ACC ATA GTT AGC TCT TCG AGC ACA GTA ATA CGT
177-h7.8    CGT GGT TCC TTG CCC CCA GTA GTC CAT AGC ATA MNN GGG GTT ACC ATA GTT AGC TCT TCG AGC ACA GTA ATA CGT
177-h7.9    CGT GGT TCC TTG CCC CCA GTA GTC CAT AGC MNN GTA GGG GTT ACC ATA GTT AGC TCT TCG AGC ACA GTA ATA CGT
177-h7.10   CGT GGT TCC TTG CCC CCA GTA GTC CAT MNN ATA GTA GGG GTT ACC ATA GTT AGC TCT TCG AGC ACA GTA ATA CGT
177-h7.11   CGT GGT TCC TTG CCC CCA GTA GTC MNN AGC ATA GTA GGG GTT ACC ATA GTT AGC TCT TCG AGC ACA GTA ATA CGT
177-h7.12   CGT GGT TCC TTG CCC CCA GTA MNN CAT AGC ATA GTA GGG GTT ACC ATA GTT AGC TCT TCG AGC ACA GTA ATA CGT
177-h7.13   CGT GGT TCC TTG CCC CCA MNN GTC CAT AGC ATA GTA GGG GTT ACC ATA GTT AGC TCT TCG AGC ACA GTA ATA CGT

FIGURE 5A

HUI77 LCDR1a
```
3000   ATA GGT GTT TCC ATT ACT ATG TAC AAT GCT CTG ACT AGA MNN GCA GGA GAT GGA GGC C
3001   ATA GGT GTT TCC ATT ACT ATG TAC AAT GCT CTG ACT MNN CCT GCA GGA GAT GGA GGC C
3002   ATA GGT GTT TCC ATT ACT ATG TAC AAT GCT CTG MNN AGA CCT GCA GGA GAT GGA GGC C
3003   ATA GGT GTT TCC ATT ACT ATG TAC AAT GCT MNN ACT AGA CCT GCA GGA GAT GGA GGC C
3004   ATA GGT GTT TCC ATT ACT ATG TAC AAT MNN CTG ACT AGA CCT GCA GGA GAT GGA GGC C
3005   ATA GGT GTT TCC ATT ACT ATG TAC MNN GCT CTG ACT AGA CCT GCA GGA GAT GGA GGC C
3006   ATA GGT GTT TCC ATT ACT ATG MNN AAT GCT CTG ACT AGA CCT GCA GGA GAT GGA GGC C
3007   ATA GGT GTT TCC ATT ACT MNN TAC AAT GCT CTG ACT AGA CCT GCA GGA GAT GGA GGC C
```
HUI77 LCDR1b
```
3008   TGG CTT CTG CAG GTA CCA TTC CAA ATA GGT GTT TCC ATT MNN ATG TAC AAT GCT CTG ACT
3009   TGG CTT CTG CAG GTA CCA TTC CAA ATA GGT GTT TCC MNN ACT ATG TAC AAT GCT CTG ACT
3010   TGG CTT CTG CAG GTA CCA TTC CAA ATA GGT GTT MNN ATT ACT ATG TAC AAT GCT CTG ACT
3011   TGG CTT CTG CAG GTA CCA TTC CAA ATA GGT MNN TCC ATT ACT ATG TAC AAT GCT CTG ACT
3012   TGG CTT CTG CAG GTA CCA TTC CAA ATA MNN GTT TCC ATT ACT ATG TAC AAT GCT CTG ACT
3013   TGG CTT CTG CAG GTA CCA TTC CAA MNN GGT GTT TCC ATT ACT ATG TAC AAT GCT CTG ACT
3014   TGG CTT CTG CAG GTA CCA TTC MNN ATA GGT GTT TCC ATT ACT ATG TAC AAT GCT CTG ACT
3015   TGG CTT CTG CAG GTA CCA MNN CAA ATA GGT GTT TCC ATT ACT ATG TAC AAT GCT CTG ACT
```
HUI77 LCDR2
```
3016   GAA CCT GTC TGG GAC TCC AGA AAA CCG GTT GGA AAC MNN ATA GAT CAG GAG CTG TGG
3017   GAA CCT GTC TGG GAC TCC AGA AAA CCG GTT GGA MNN TTT ATA GAT CAG GAG CTG TGG
3018   GAA CCT GTC TGG GAC TCC AGA AAA CCG GTT MNN AAC TTT ATA GAT CAG GAG CTG TGG
3019   GAA CCT GTC TGG GAC TCC AGA AAA CCG MNN GGA AAC TTT ATA GAT CAG GAG CTG TGG
3020   GAA CCT GTC TGG GAC TCC AGA AAA MNN GTT GGA AAC TTT ATA GAT CAG GAG CTG TGG
3021   GAA CCT GTC TGG GAC TCC AGA MNN CCG GTT GGA AAC TTT ATA GAT CAG GAG CTG TGG
3022   GAA CCT GTC TGG GAC TCC MNN AAA CCG GTT GGA AAC TTT ATA GAT CAG GAG CTG TGG
```
HUI77 HCDR1
```
3023   TGG GGG CTG ACG GAT CCA GCC CAC ACC CAT TCC AGA MNN GCT GAG TGA GAA CCC AGA
3024   TGG GGG CTG ACG GAT CCA GCC CAC ACC CAT TCC MNN AGT GCT GAG TGA GAA CCC AGA
3025   TGG GGG CTG ACG GAT CCA GCC CAC ACC CAT MNN AGA AGT GCT GAG TGA GAA CCC AGA
3026   TGG GGG CTG ACG GAT CCA GCC CAC ACC MNN TCC AGA AGT GCT GAG TGA GAA CCC AGA
3027   TGG GGG CTG ACG GAT CCA GCC CAC MNN CAT TCC AGA AGT GCT GAG TGA GAA CCC AGA
3028   TGG GGG CTG ACG GAT CCA GCC MNN ACC CAT TCC AGA AGT GCT GAG TGA GAA CCC AGA
3029   TGG GGG CTG ACG GAT CCA MNN CAC ACC CAT TCC AGA AGT GCT GAG TGA GAA CCC AGA
```
HUI77 HCDR2a
```
3038   CAG AGA TGG GTT GTA GTA TTT ATT GTC ATC CCA CCA AAT MNN TGC AAG CCA CTC CAG GGC
3039   CAG AGA TGG GTT GTA GTA TTT ATT GTC ATC CCA CCA MNN GTC TGC AAG CCA CTC CAG GGC
3040   CAG AGA TGG GTT GTA GTA TTT ATT GTC ATC CCA MNN AAT GTC TGC AAG CCA CTC CAG GGC
3041   CAG AGA TGG GTT GTA GTA TTT ATT GTC ATC MNN CCA AAT GTC TGC AAG CCA CTC CAG GGC
3042   CAG AGA TGG GTT GTA GTA TTT ATT GTC MNN CCA CCA AAT GTC TGC AAG CCA CTC CAG GGC
3043   CAG AGA TGG GTT GTA GTA TTT ATT MNN ATC CCA CCA AAT GTC TGC AAG CCA CTC CAG GGC
3044   CAG AGA TGG GTT GTA GTA TTT MNN GTC ATC CCA CCA AAT GTC TGC AAG CCA CTC CAG GGC
3045   CAG AGA TGG GTT GTA GTA MNN ATT GTC ATC CCA CCA AAT GTC TGC AAG CCA CTC CAG GGC
```
HUI77 HCDR2b
```
3030   CTT GGA GAT GGT GAG CCT GCT CTT CAG AGA TGG GTT GTA MNN TTT ATT GTC ATC CCA CCA
3031   CTT GGA GAT GGT GAG CCT GCT CTT CAG AGA TGG GTT MNN GTA TTT ATT GTC ATC CCA CCA
3032   CTT GGA GAT GGT GAG CCT GCT CTT CAG AGA TGG MNN GTA GTA TTT ATT GTC ATC CCA CCA
3033   CTT GGA GAT GGT GAG CCT GCT CTT CAG AGA MNN GTT GTA GTA TTT ATT GTC ATC CCA CCA
3034   CTT GGA GAT GGT GAG CCT GCT CTT CAG MNN TGG GTT GTA GTA TTT ATT GTC ATC CCA CCA
3035   CTT GGA GAT GGT GAG CCT GCT CTT MNN AGA TGG GTT GTA GTA TTT ATT GTC ATC CCA CCA
3036   CTT GGA GAT GGT GAG CCT GCT MNN CAG AGA TGG GTT GTA GTA TTT ATT GTC ATC CCA CCA
3037   CTT GGA GAT GGT GAG CCT MNN CTT CAG AGA TGG GTT GTA GTA TTT ATT GTC ATC CCA CCA
```

FIGURE 5B

Beneficial Mutations for HuI-77 Antibody

| CDRs | H1 | | H2 | | H3 | | | | L1 | | | | | | L2 | | | | | L3 | | | | | | |
|---|---|---|---|---|---|---|---|---|---|---|---|---|---|---|---|---|---|---|---|---|---|---|---|---|---|---|
| Kabat Number | 32 | 35b | 59 | 64 | 95 | 100 | 100e | 102 | 27c | 27d | 27e | 28 | 30 | 33 | 50 | 51 | 53 | 54 | 56 | 89 | 90 | 91 | 92 | 93 | 94 | 97 |
| HuI-77 | S | G | Y | K | R | N | M | Y | V | H | S | N | N | L | K | V | N | R | S | F | Q | G | S | H | V | T |
| Mutations | P | L | S | P | P | Q | Q | K | P | L | W | Y | Y | F | S | A | S | L | W | V | R | S | W | L | T | A |
|  | W | A | A |  | Q | W | N | T | W | S |  | Y |  | V |  |  | L |  | F | H | W |  | E | T | A | R |
|  |  |  | P |  | L |  | T | M |  |  |  |  |  |  |  |  |  |  |  |  |  |  | T | S |  | H |
|  |  |  |  |  | T |  |  | H |  |  |  |  |  |  |  |  |  |  |  |  |  |  |  | A |  | K |
|  |  |  |  |  | V |  |  |  |  |  |  |  |  |  |  |  |  |  |  |  |  |  |  | Q |  | I |

FIGURE 5C

Beneficial mutations chosen for combinatorial library

| CDRs | H1 | H2 | | H3 | L1 | | | L3 | SPEkon | SPEkoff |
|---|---|---|---|---|---|---|---|---|---|---|
| Kabat Number | 35 | 57 | 62 | 102 | 27d | 27e | 27f | 93 | O.D.560 | O.D.560 |
| wild type | S | I | S | Y | N | S | G | S | | |
| HuIV-26 | S | I | S | Y | N | S | G | S | | |
| Mutations | T | A | Y | P | S | Y | Y | Q | | |
|  | A |  | A |  |  | W | R |  | | |
|  |  |  | H |  |  | H | H |  | | |
|  |  |  |  |  |  | R |  |  | | |

Beneficial mutants

| | H1 | H2 | | H3 | L1 | | | L3 | SPEkon | SPEkoff |
|---|---|---|---|---|---|---|---|---|---|---|
| 4.1-2D4 | S | I | S | P | N | S | G | Q | | |
| L1b-F11 | S | I | S | P | N | S | Y | Q | 0.745 | 0.483 |
| H2a-G8 | S | A | S | P | N | S | G | Q | 0.397 | 0.159 |
| 2D4H1-C3 | A | I | S | P | N | S | G | Q | | |
| DcomA4 | S | A | Y | P | N | Y | Y | Q | 0.981 | 0.769 |
| DcomB1 | A | A | Y | P | N | Y | H | Q | 1.018 | 0.714 |
| DcomE1 | | | | | | | | | 1.031 | 0.758 |
| DcomH2 | | | | | | | | | 1.07 | 0.705 |
| DcomD2 | S | A | S | P | N | R | Y | Q | 1.104 | 0.729 |
| DcomD3 | T | A | Y | P | N | S | Y | Q | 1.035 | 0.736 |
| DcomD6 | S | A | Y | P | N | W | Y | Q | 1.102 | 0.753 |
| DcomA11 | | | | | | | | | 1.003 | 0.786 |
| DcomE3 | T | A | Y | P | N | R | Y | Q | 0.991 | 0.754 |
| DcomG2 | A | A | Y | P | N | R | Y | Q | 1.161 | 0.856 |
| DcomA7 | T | V | S | P | N | Y | Y | Q | 0.986 | 0.77 |
| DcomB8 | T | A | A | P | N | W | Y | Q | 0.998 | 0.807 |
| DcomA2 | | | | | | | | | 1.026 | 0.74 |
| DcomB10 | T | A | H | P | N | W | Y | Q | 0.87 | 0.735 |
| DcomC8 | S | A | A | P | N | W | Y | Q | 0.978 | 0.763 |
| DcomD7 | T | A | Y | P | N | W | Y | Q | 1.083 | 0.794 |
| DhuG5 | | | | | | | | | | |
| DhuH8 | | | | | | | | | | |
| DcomD11 | A | A | A | P | N | W | H | Q | 1.125 | 0.752 |
| DcomE11 | A | A | H | P | N | W | H | Q | 0.973 | 0.732 |

Primers for combinatorial mutation

```
dH5762    TCTCTGGAGATGGTGAATTTACGTACTGCTATCTGGATT
dL27def   CTAAGTAGTTCTTTTGGTTGTTATAACAGACTCTGGCTGGA
H1-35     TGGAGCCTGGCGGACCCAGGHCATCCAATATCTACTAAAGGTGAATCCAGA
H2-5762a  TCTCTGGAGATGGTGAATCTATCCTTTAGGGMTGGCGTATAGTTGGCCGTACTGCTATCTGGATT
H2-5762b  TCTCTGGAGATGGTGAATCTATCCTTTAGGTRTGGCGTATAGTTGGCCGTACTGCTATCTGGATT
L1-27def1 CTAAGTAGTTCTTTTGGTTGTRGTRGYTAACAGACTCTGGCTGGA
L1-27def2 CTAAGTAGTTCTTTTGGTTGCSGTRGYTAACAGACTCTGGCTGGA
L1-27def3 CTAAGTAGTTCTTTTGGTTGTRGCKGYTAACAGACTCTGGCTGGA
L1-27def4 CTAAGTAGTTCTTTTGGTTGCSGCKGYTAACAGACTCTGGCTGGA
L1-27def5 CTAAGTAGTTCTTTTGGTTGTRCCAGYTAACAGACTCTGGCTGGA
L1-27def6 CTAAGTAGTTCTTTTGGTTGCSCCAGYTAACAGACTCTGGCTGGA
```

FIGURE 6

Beneficial mutations chosen for combinatorial library

| CDRs | H1 | | H2 | H3 | L1 | | | L3 | Screen | Screen |
|---|---|---|---|---|---|---|---|---|---|---|
| Kabat Number | 32 | 35b | 59 | 100e | 27d | 28 | 33 | 94 | kon | koff |
| wild type | S | G | Y | M | H | N | L | V | | |
| HuI-77 | S | G | Y | M | H | N | L | V | | |
| Mutations | P | W | S | Q | L | Y | F | | | |
| | | L | A | | S | W | | | | |
| | | A | P | | | | | | | |
| Beneficial combinatonal mutants | | | | | | | | | | |
| Qh2b-B7 | S | G | A | Q | H | N | L | V | | |
| Qh2b-A3 | S | G | S | Q | H | N | L | V | | |
| Qcom1B6 | P | W | S | Q | S | W | L | V | 1.319 | 0.534 |
| Qcom1B8 | P | W | S | Q | S | Y | L | V | 1.266 | 0.497 |
| Qcom1E7 | | | | | | | | | 1.247 | 0.46 |
| Qcom1G10 | | | | | | | | | 1.282 | 0.452 |
| Qcom2G2 | | | | | | | | | 1.304 | 0.402 |
| Qcom1C3 | P | W | A | Q | S | W | L | V | 1.342 | 0.535 |
| Qcom2A2 | | | | | | | | | 1.605 | 0.647 |
| Qcom1G3 | | | | | | | | | 1.274 | 0.464 |
| Qcom1D3 | P | W | T | Q | S | W | L | V | 1.647 | 0.984 |
| QhuD9 | | | | | | | | | | |
| QhuD93 | | | | | | | | | | |
| Qcom1E3 | P | W | A | Q | S | Q | L | V | 1.225 | 0.347 |
| Qcom2F6 | | | | | | | | | 1.311 | 0.321 |
| Qcom1H6 | P | W | S | Q | S | Q | L | V | 1.295 | 0.323 |
| Qcom1H7 | P | W | A | Q | H | Q | F | F | 1.634 | 1.08 |
| Qcom2A4 | P | A | A | Q | S | Y | L | V | 1.304 | 0.265 |
| Qcom2B11 | P | W | A | Q | H | Y | L | V | 1.11 | 0.221 |
| Qcom2C1 | P | W | Y | Q | S | W | F | V | 1.189 | 0.213 |
| Qcom2D9 | P | W | S | Q | H | W | L | V | 1.101 | 0.209 |
| Qcom2E3 | P | W | A | Q | H | W | L | V | 1.117 | 0.248 |

Primers for combinatorial mutation

```
dL27d-33 CTT CTG CAG GTA CCA TTC GTTA TAC AAT GCT CTG ACT AGA
H1-35b1 TGG GGG CTG ACG GAT CCA CMA CAC ACC CAT TCC AGR AGT GCT GAG TGA GAA CCC AGA
H1-35b2 TGG GGG CTG ACG GAT CCA GSC CAC ACC CAT TCC AGR AGT GCT GAG TGA GAA CCC AGA
H2-59 GCT CTT CAG AGA TGG GTT AGV GTA TTT ATT GTC ATC CCA C
L27d1 CTT CTG CAG GTA CCA TTC MAA ATA GGT GTT TCC CCA ACT CRA TAC AAT GCT CTG ACT AGA
L27d2 CTT CTG CAG GTA CCA TTC MAA ATA GGT GTT TCC GTA ACT CRA TAC AAT GCT CTG ACT AGA
L27d3 CTT CTG CAG GTA CCA TTC MAA ATA GGT GTT TCC CTG ACT CRA TAC AAT GCT CTG ACT AGA
L27d4 CTT CTG CAG GTA CCA TTC MAA ATA GGT GTT TCC CCA ACT GTG TAC AAT GCT CTG ACT AGA
L27d5 CTT CTG CAG GTA CCA TTC MAA ATA GGT GTT TCC GTA ACT GTG TAC AAT GCT CTG ACT AGA
L27d6 CTT CTG CAG GTA CCA TTC MAA ATA GGT GTT TCC CTG ACT GTG TAC AAT GCT CTG ACT AGA
```

HUMANIZED COLLAGEN ANTIBODIES AND RELATED METHODS

CROSS-REFERENCE

This application is a divisional application of U.S. application Ser. No. 10/011,250, filed Dec. 6, 2001, entitled "Humanized Collagen Antibodies and Related Methods," now U.S. Pat. No. 7,390,885, which is a continuation-in-part of U.S. application Ser. No. 09/995,529, filed Nov. 26, 2001, entitled "Humanized Collagen Antibodies and Related Methods," now U.S. Pat. No. 7,365,167, each of which is incorporated herein by reference in its entirety.

BACKGROUND OF THE INVENTION

The present invention relates generally to immunology and more specifically to humanized antibodies and uses thereof.

The extracellular matrix (ECM) plays a fundamental role in the regulation of normal and pathological processes. The most abundantly expressed component found in the ECM is collagen. Triple helical collagen is known to be highly resistant to proteolytic cleavage except by members of the matrix metalloproteinase (MMP) family of enzymes.

Angiogenesis and tumor growth depend on cellular interactions with the extracellular matrix. During angiogenesis and tumor invasion, both endothelial cells as well as tumor cells proteolytically remodel their extracellular microenvironment. The invasive cells then interact with this newly remodeled extracellular matrix followed by migration and invasion. To this end, a major component of the basement membrane surrounding blood vessels is collagen-IV. Moreover, collagen-I is the major component of the interestitial matrix.

One of the major detrimental consequences of the progression of cancer is metastasis beyond the site of the primary tumor. Such metastasis often requires more aggressive therapies, and once metastasis has occurred, the prognosis for survival of a cancer patient decreases dramatically.

The growth of all solid tumors requires new blood vessel growth for continued expansion of the tumors, particularly beyond a minimal size. Because angiogenesis is required for tumor growth, inhibiting angiogenesis is one approach to inhibiting tumor growth. It is therefore desirable to identify molecules that can target angiogenic vasculature. Particularly attractive molecules for targeting angiogenic vasculature are antibodies that can bind specifically to angiogenic vasculature. However, since most antibodies are developed in non-human animals such as mice, these antibodies often have undesirable immunogenic activity that limits their effectiveness for human therapy.

One approach to overcoming the detrimental properties of non-human antibodies is to humanize the antibodies by using human antibody framework region sequences spliced together with the binding domains that confer binding specificity. However, grafting of these binding domains, referred to as complementarity determining regions (CDRs), into human frameworks has often resulted in the loss of binding affinity.

Thus, there exists a need to identify antibodies specific for angiogenic vasculature and to humanize and optimize the antibodies for therapeutic purposes. The following invention satisfies this need and provides related advantages as well.

SUMMARY OF THE INVENTION

The invention provides a grafted antibody, or functional fragment thereof, comprising one or more complementarity determining regions (CDRs) having at least one amino acid substitution in one or more CDRs of a heavy chain CDR, where the grafted antibody or functional fragment thereof has specific binding activity for a cryptic collagen epitope. The invention also provides methods of using an antibody having specific binding activity for a cryptic collagen epitope, including methods of inhibiting angiogenesis, tumor growth, and metastasis.

BRIEF DESCRIPTION OF THE DRAWINGS

FIG. 1 shows the sequences of primers used to clone nucleic acids encoding HUIV26 and HUI77 antibodies. FIG. 1A shows a set of 5' primers for the signal peptide of mouse antibody light chain (SEQ ID NOS: 184-192). FIG. 1B shows a set of 5' primers for the signal peptide of mouse antibody heavy chain (SEQ ID NOS: 193-211). FIG. 1C shows a set of primers for the constant region of mouse heavy and light chains. Primer 2650 (SEQ ID NO:212) is the 3' primer for mouse kappa light chain constant region (amino acids 123-115). Primer 2656 (SEQ ID NO:213) is the 3' primer for mouse IgM CH1 region (amino acids 121-114). Primer 2706 (SEQ ID NO:214) is the 3' primer for mouse IgM CH1 region (amino acids 131-124).

FIG. 2 shows the sequence of the variable region of anti-cryptic collagen site antibody HUIV26. FIG. 2A shows the nucleotide sequence of HUIV26 variable region light chain (SEQ ID NO:1). FIG. 2B shows the nucleotide sequence of HUIV26 variable region heavy chain (SEQ ID NO:3). FIG. 2C shows an alignment of the amino acid sequence of HUIV26 light chain ($V_K$) domain of HUIV26 (SEQ ID NO:2) with a human variable region fusion, VKIV/JK2 (SEQ ID NO:6) and an alignment of HUIV26 heavy chain ($V_H$) domain (SEQ ID NO:4) with a human variable region fusion VHIII/JH6 (SEQ ID NO:8), with CDRs underlined. Amino acids in the framework region that differ between the aligned sequences are indicated by lines.

FIG. 3 shows the sequence of the variable region of anti-cryptic collagen site antibody HUI77. FIG. 3A shows the nucleotide sequence of HUI77 variable region light chain (SEQ ID NO:9). FIG. 3B shows the nucleotide sequence of HUI77 variable region heavy chain (SEQ ID NO:11). FIG. 3C shows an alignment of the amino acid sequence of HUI77 light chain ($V_K$) domain of HUI77 (SEQ ID NO: 10) with a human variable region fusion, VKII/JK1 (SEQ ID NO:14) and an alignment of HUI77 heavy chain ($V_H$) domain (SEQ ID NO:12) with a human variable region fusion VHIII/JH6 (SEQ ID NO:16), with CDRs underlined. Amino acids in the framwork region that differ between the aligned sequences are indicated by lines. FIG. 3D shows an alignment of the nucleotide sequence of HUI77 variable region with the sequence of the human framework fusion of DPK13 and JK1 (SEQ ID NO:17).

FIG. 4 shows beneficial CDR mutations for anti-cryptic collagen site antibody HUIV26. FIG. 4A shows a set of primers used to generate random mutations in LCDR3 and HCDR3 of HUIV26 (HUIV26 LCDR3 primers, SEQ ID NOS:224-232; HUIV26 HCDR3 primers, SEQ ID NOS:233-243). FIG. 4B shows a set of primers used to generate random mutations in LCDR1a (SEQ ID NOS:266-273), LCDR1b (SEQ ID NOS:274-282), LCDR2 (SEQ ID NOS:283-289), HCDR1 (SEQ ID NOS:290-294), HCDR2a (SEQ ID NOS: 295-303) and HCDR2b (SEQ ID NOS:304-311) of HUIV26. FIG. 4C shows beneficial CDR mutations of the HUIV26 antibody.

FIG. 5 shows beneficial CDR mutations for anti-cryptic collagen site antibody HUI77. FIG. 5A shows a set of primers used to generate random mutations in LCDR3 and HCDR3 of HUI77. FIG. 5B shows a set of primers used to generate random mutations in LCDR1a (SEQ ID NOS:312-319), LCDR1b (SEQ ID NOS:320-327), LCDR2 (SEQ ID NOS: 328-334), HCDR1 (SEQ ID NOS:335-341), HCDR2a (SEQ ID NOS:342-349) and HCDR2b (SEQ ID NOS:350-357) of HUI77. FIG. 5C shows beneficial CDR mutations of the HUI77 antibody.

FIG. 6 shows mutations in combinatorial variants of the HUIV26 antibody. The position of amino acids are shown, with mutations different than wild type shown in bold. The relative activity of combinatorial variants is shown as "SPEK$_{on}$" and "SPEK$_{off}$" (last column). Primers used to create the combinatorial libraries are also shown (SEQ ID NOS: 163-173).

FIG. 7 shows mutations in combinatorial variants of the HUI77 antibody. The position of amino acids are shown, with mutations different than wild type shown in bold. The relative activity of combinatorial variants is shown as "SPEK$_{on}$" and "SPEK$_{off}$" (last column). Primers used to create the combinatorial libraries are also shown (SEQ ID NOS:174-183).

DETAILED DESCRIPTION OF THE INVENTION

Figure 8:
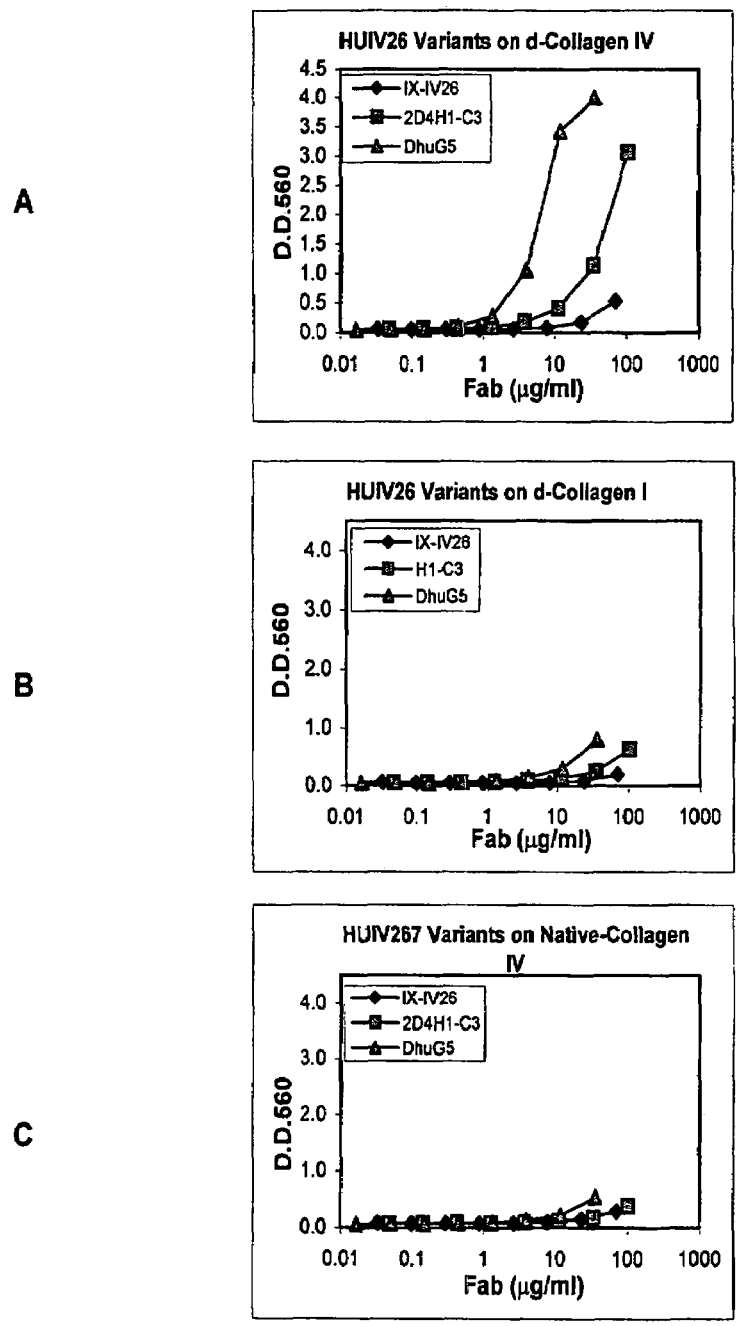
FIG. 8 shows the activity and specificity of HUIV26 variants. The binding of purified Fabs of IX IV26, containing wild type HUIV26 CDRs, and the HUIV26 variants 2D4H1-C3 and DhuG5 is shown for denatured collagen IV (FIG. 8A), denatured collagen I (FIG. 8B) and native collagen IV (FIG. 8C).

The invention provides antibodies specific for a cryptic collagen site, which is exposed during angiogenesis and tumor cell invasion through collagenous tissue and thus serves as an antibody that can target angiogenic vasculature. The antibodies are optimized for binding activity to a cryptic collagen site. The antibodies can be used to target angiogenic vasculature for diagnostic or therapeutic purposes. The antibodies can also be used to inhibit tumor growth.

As used herein, the term "CDR" or "complementarity determining region" is intended to mean the non-contiguous antigen combining sites found within the variable region of both heavy and light chain polypeptides. These particular regions-have been described by Kabat et al., *J. Biol. Chem.* 252:6609-6616 (1977); Kabat et al., U.S. Dept. of Health and Human Services, "Sequences of proteins of immunological interest" (1991); by Chothia et al., *J. Mol. Biol.* 196:901-917 (1987); and MacCallum et al., *J. Mol. Biol.* 262:732-745 (1996), where the definitions include overlapping or subsets of amino, acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally between about 100-120 amino acids in length but is intended to reference only those amino acids outside of the CDRs. As used herein, the term "framework region" is intended to mean each domain of the framework that is separated by the CDRs.

As used herein, the term "donor" is intended to mean a parent antibody molecule or fragment thereof from which a portion is derived from, given to or contributes to another antibody molecule or fragment thereof so as to confer either a structural or functional characteristic of the parent molecule onto the receiving molecule. For the specific example of CDR grafting, the parent molecule from which the grafted CDRs are derived is a donor molecule. The donor CDRs confer the binding affinity of the parent molecule onto the receiving molecule. The donor molecule can be a different species or the same species as the receiving molecule. If the donor and receiving molecules are of the same species, it is understood that it is sufficient that the donor is a separate and distinct molecule from the receiving molecule.

As used herein, the term "acceptor" is intended to mean an antibody molecule or fragment thereof which is to receive the donated portion from the parent or donor antibody molecule or fragment thereof. An acceptor antibody molecule or fragment thereof is therefore imparted with the structural or functional characteristic of the donated portion of the parent molecule. For the specific example of CDR grafting, an acceptor molecule, including framework and/or other antibody fragments, is the receiving molecule into which the CDRs are grafted. The acceptor antibody molecule or fragment is imparted with the binding affinity of the donor CDRs or parent molecule. As with a donor molecule, it is understood that an acceptor molecule can be the same or a different species as the donor.

A "variable region" when used in reference to an antibody or a heavy or light chain thereof is intended to mean the amino terminal portion of an antibody which confers antigen binding onto the molecule and which is not the constant region. The term is intended to include functional fragments thereof which maintain some of all of the binding function of the whole variable region. Therefore, the term "heteromeric variable region binding fragments" is intended to mean at least one heavy chain variable region and at least one light chain variable regions or functional fragments thereof assembled into a heteromeric complex. Heteromeric variable region binding fragments include, for example, functional fragments such as Fab, F(ab)$_2$, Fv, single chain Fv (scFv) and the like.

Such functional fragments are well known to those skilled in the art. Accordingly, the use of these terms in describing functional fragments of a heteromeric variable region is intended to correspond to the definitions well known to those skilled in the art. Such terms are described in, for example, Harlow and Lane, *Antibodies: A Laboratory Manual*, Cold Spring Harbor Laboratory, New York (1989); *Molec. Biology and Biotechnology: A Comprehensive Desk Reference* (Myers, R. A. (ed.), New York: VCH Publisher, Inc.); Huston et al., *Cell Biophysics*, 22:189-224 (1993); Plückthun and Skerra, *Meth. Enzymol.*, 178:497-515 (1989); and in Day, E. D., *Advanced Immunochemistry*, Second Ed., Wiley-Liss, Inc., New York, N.Y. (1990).

As used herein, the term "population" is intended to refer to a group of two or more different molecules. A population can be as large as the number of individual molecules currently available to the user or able to be made by one skilled in the art. Populations can be as small as 2-4 molecules or as large as 1013 molecules. Generally, a population will contain two or more, three or more, five or more, nine or more, ten or more, twelve or more, fifteen or more, or twenty or more different molecules. A population can also contain tens or hundreds of different molecules or even thousands of different molecules. For example, a population can contain about 20 to about 100,000 different molecules or more, for example about 25 or more, 30 or more, 40 or more, 50 or more, 75 or more, 100 or more, 150 or more, 200 or more, 300 or more, 500 or more, or 1000 or more different molecules, and can contain 10,000, 100,000 or even $1 \times 10^6$ or more different molecules. Those skilled in the art will know what size and diversity of a population is suitable for a particular application.

As used herein, the term "altered" when used in reference to an antibody variable region is intended to mean a heavy or light chain variable region that contains one or more amino acid changes in a framework region, a CDR or both compared to the parent amino acid sequence at the same position. Where an altered variable region is derived from or composed of donor and acceptor regions, the changed amino acid residues within the altered species are to be compared to their respective amino acid positions within the parent donor and acceptor regions.

As used herein, the term "nucleic acid" or "nucleic acids" is intended to mean a single- or double-stranded DNA or RNA molecule. A nucleic acid molecule of the invention can be of linear, circular or branched configuration, and can represent either the sense or antisense strand, or both, of a nucleic acid molecule. The term also is intended to include nucleic acid molecules of both synthetic and natural origin. A nucleic acid molecule of natural origin can be derived from any animal, such as a human, non-human primate, mouse, rat, rabbit, bovine, porcine, ovine, canine, feline, or amphibian, or from a lower eukaryote, such as *Drosophila, C. elegans*, yeast, and the like. A synthetic nucleic acid includes, for example, chemical and enzymatic synthesis. The term "nucleic acid" or "nucleic acids" is similarly intended to include analogues of natural nucleotides which have similar functional properties as the referenced nucleic acid and which can be utilized in a manner similar to naturally occurring nucleotides and nucleosides.

As used herein, the term "antibody" is used in its broadest sense to include polyclonal and monoclonal antibodies, as well as antigen binding fragments of such antibodies. An antibody useful in the invention, or antigen binding fragment of such an antibody, is characterized by having specific binding activity for a polypeptide or a peptide portion thereof of at least about $1 \times 10^5 M^{-1}$. Thus, Fab, F(ab')$_2$, Fd, Fv, single chain Fv (scFv) fragments of an antibody and the like, which retain specific binding activity for a polypeptide, are included within the definition of an antibody. Specific binding activity of an antibody for a polypeptide can be readily determined by one skilled in the art, for example, by comparing the binding activity of an antibody to a particular polypeptide versus a control polypeptide that is not the particular polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making functional antibodies are well known to those skilled in the art (Winter and Harris, *Immunol. Today* 14:243-246 (1993); Ward et al., *Nature* 341: 544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

As used herein, specific binding means binding that is measurably different from a non specific interaction. Specific binding can be measured, for example, by determining binding of a molecule compared to binding of a control molecule, which generally is a molecule of similar structure that does not have binding activity, for example, an antibody that binds a distinct epitope or antigen. Specificity of binding also can be determined, for example, by competition with a control molecule, for example, competition with an excess of the same molecule. In this case, specific binding is indicated if the binding of a molecule is competitively inhibited by itself. Thus, specific binding between an antibody and antigen is measurably different from a non specific interaction and occurs via the antigen binding site of the antibody.

As used herein, selective binding refers to a binding interaction that is both specific and discriminating between molecules, for example, an antibody that binds to a single molecule or closely related molecules. For example, an antibody can exhibit specificity for an antigen that can be both specific and selective for the antigen if the epitope is unique to a molecule. Thus, a molecule having selective binding can differentiate between molecules, as exemplified by an antibody having specificity for an epitope unique to one molecule or closely related molecules. Alternatively, an antibody can have specificity for an epitope that is common to many molecules, for example, a carbohydrate that is expressed on a number of molecules. Such an antibody has specific binding but is not selective for one molecule or closely related molecules.

As used herein the term "binding affinity" is intended to mean the strength of a binding interaction and includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction. For example, a bivalent heteromeric variable region binding fragment can exhibit altered or optimized binding affinity due to its valency.

As used herein, the term "substantially the same" when used in reference to binding affinity is intended to mean similar or identical binding affinities where one molecule has a binding affinity that is similar to another molecule within the experimental variability of the affinity measurement. The experimental variability of the binding affinity measurement is dependent upon the specific assay used and is known to those skilled in the art.

As used herein, the term "optimizing" when used in reference to a variable region or a functional fragment thereof is intended to mean that the functional activity of the variable region has been modified compared to the activity of a parent variable region or a donor variable region, resulting in a desirable change in activity. A variable region or functional fragment thereof exhibiting optimized activity can exhibit, for example, higher affinity or lower affinity binding, or increased or decreased association or dissociation rates compared to an unaltered variable region. A variable region or functional fragment thereof exhibiting optimized activity also can exhibit increased stability such as increased half-life in a particular organism. For example, an antibody activity can be optimized to increase stability by decreasing susceptibility to proteolysis. An antibody exhibiting optimized activity also can exhibit lower affinity binding, including decreased association rates or increased dissociation rates, if desired. An optimized variable region exhibiting lower affinity binding is useful, for example, for penetrating a solid tumor. In contrast to a higher affinity variable region, which would bind to the peripheral regions of the tumor but would be unable to penetrate to the inner regions of the tumor due to its high affinity, a lower affinity variable region would be advantageous for penetrating the inner regions of the tumor. As with optimization of binding affinities above, optimization of a catalytic variable region can be, for example, increased or decreased catalytic rates, disassociation constants or association constants.

As used herein, a "cryptic collagen site" or "cryptic collagen epitope" refers to an epitope of a collagen molecule that is less accessible to binding of an antibody, or functional fragment thereof, in native collagen than in denatured collagen. An antibody having binding activity for a cryptic collagen epitope preferentially recognizes denatured collagen over native collagen, that is, has a higher binding affinity for denatured over native collagen. For example, such an antibody can have at least about a 2-fold or greater preference, that is, at least about 2 fold higher binding activity, for denatured collage over native collagen, and can exhibit about a 3 fold or greater preference, about a 5 fold or greater preference, about a 10-fold or greater preference, about a 15-fold or greater preference, about a 20-fold or greater preference, about a 25-fold or greater preference, about a 50-fold or greater preference, about a 100-fold or greater preference, or even a higher preference for denatured over native collagen.

Native collagen herein refers to a molecule where three alpha-chains are organized in a triple helical molecule. Native collagen can be of different stages of post-translational processing such as pro collagen and any intermediates in the generation of a mature tissue form of collagen, or collagen molecules isolated by limited proteolysis of tissues under conditions where the triple-helical structure of collagen is not disrupted. Thus, native collagen can be an intact collagen molecule or can contain non-triple-helical sequences flanking triple-helical regions, so long as the triple-helical is not disrupted. Denatured collagen herein refers to collagen where the triple helix is completely or partially disrupted such that a cryptic epitope is made accessible. Denaturation of collagen can occur in situ by the action of proteinases, for example, matrix metalloproteinases, that cleave collagen within triple helical regions, rendering the resulting fragments of the triple helix unstable. Denaturation of collagen can be induced in vitro by thermal or chemical denaturation of native collagen. Denatured collagen can also be prepared in vitro by treatment of native collagen with proteinases capable of cleaving a triple helical region(s), which are commonly referred to as collagenolytic enzymes, at temperatures where the resulting fragments of the triple helix are thermally unstable. Denatured collagen can be obtained by denaturation of native collagens of different stages of post-translational processing or denaturation of native collagen isolated from tissues by limited proteolysis. One skilled in the art will know a variety of methods for isolation of native collagens and a variety of methods to denature a triple helix that contains a cryptic collagen epitope.

An antibody of the invention can have binding activity for a cryptic collagen epitope that is the same as the respective parental mouse antibody. For example, an antibody of the invention having CDRs derived from HUIV26 can have essentially the same binding specificity as the mouse HUIV26 antibody described by Xu et al., *Hybridoma* 19:375-385 (2000); Xu et al., *J. Cell Biol.* 154:1069-1079 (2001); and WO 00/40597, each of which is incorporated herein by reference. Similarly, an antibody of the invention having CDRs derived from HUI77 can have essentially the same binding specificity as the mouse HUI77 antibody described by Xu et al., supra, 2000; Xu et al., supra, 2001; and WO 00/40597. Such binding specificity can be tested by the methods disclosed herein, for example, by comparing the activity of an antibody of the invention to the corresponding parental mouse antibody. For example, an antibody of the invention derived from HUIV26 can be compared to a corresponding mouse antibody having the variable region amino acid sequence shown in FIG. 2C (SEQ ID NOS:2 and 4). Similarly, an antibody of the invention derived from HUI77 can be compared to a corresponding mouse antibody having the variable region amino acid sequence shown in FIG. 3C (SEQ ID NOS:10 and 12). Similar binding specificity can be determined, for example, by competitive binding with the corresponding parental antibody. It is understood that an antibody of the invention can have essentially the same specificity as the corresponding parental antibody or can have altered specificity so long as the antibody has binding activity for a cryptic collagen epitope.

The invention provides antibodies having specific binding activity for a cryptic collagen epitope. The antibodies contain at least one CDR having at least one amino acid substitution in a CDR of the antibodies HUIV26 and HUI77, which are antibodies that bind to a cryptic collagen site. The invention also provides nucleic acids encoding these antibodies. The invention further provides methods using the antibodies.

Highly specific monoclonal antibodies have been developed that recognize a cryptic domain of human collagen, designated HUIV26 and HUI77 (see Xu et al., *Hybridoma* 19:375-385 (2000); Xu et al., *J. Cell Biol.* 154:1069-1079 (2001); WO 00/40597, each of which is incorporated herein by reference). Monoclonal antibody HUIV26 recognizes a cryptic domain of human collagen-IV, and HUI77 recognizes a cryptic domain of human collagen-I and IV that is also common to collagens II, III and V. This cryptic domain(s) is less accessible under most normal physiological conditions but becomes accessible following proteolytic remodeling of the collagen triple helix in vivo. Thus, cryptic collagen epitope(s) can become more accessible during invasive cellular processes. Importantly, the cryptic domain(s) defined by these antibodies was shown to be exposed within the basement membrane of tumor associated angiogenic blood vessels from human tumors including, breast, bladder and melanoma tumors. However, this cryptic domain was less exposed within the vessels or normal tissues tested. Therefore, the antibodies HUIV26 and HUI77 represent important and specific markers of angiogenic blood vessels. These cryptic domain(s) plays an important role in regulating angiogenesis and tumor growth since the monoclonal antibodies HUIV26 and HUI77 potently inhibit angiogensis and human tumor growth in the chick embryo, rat and mouse models following systemic administration (Xu et al., supra, 2001). Thus, these monoclonal antibodies and the antibodies of the invention having specific binding activity for these cryptic collagen site(s) represent a highly potent and effective new therapeutic reagent for the treatment for diseases characterized by aberrant neovascularization.

A nucleic acid sequence of the invention can include a sequence that is the same or substantially the same as a specifically recited SEQ ID NO. Similarly, an amino acid sequence of the invention can include a sequence that is the same or substantially the same as a specifically recited SEQ ID NO. As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence, for example, the sequence of a parent antibody. Such a considerable degree, amount or extent of sequence identity is further considered to be significant and meaningful and therefore exhibit characteristics which are definitively recognizable or known. Thus, a nucleotide sequence which is substantially the same nucleotide sequence as a heavy or light chain of an antibody of the invention, including fragments thereof, refers to a sequence which exhibits characteristics that are definitively known or recognizable as encoding or as being the amino acid sequence as the parent antibody sequence. Minor modifications thereof are included so long as they are recognizable as a parent antibody sequence. Similarly, an amino acid sequence which is substantially the same amino acid sequence as a heavy or light chain of an antibody of the invention, or functional fragment thereof, refers to a sequence which exhibits characteristics that are definitively known or recognizable as representing the amino acid sequence of parent antibody and minor modifications thereof. When determining whether a nucleotide or amino acid sequence is substantially the same as a parent antibody, consideration is given to the number of changes relative to the parent antibody together with whether the function is maintained, for example, whether the function of binding to a cryptic collagen site is maintained for antibodies of the invention.

Minor modification of these nucleotide sequences and/or amino acids are intended to be included as heavy and light chain encoding nucleic acids and their functional fragments. Such minor modifications include, for example, those which do not change the encoded amino acid sequence due to the degeneracy of the genetic code as well as those which result in only a conservative substitution of the encoded amino acid sequence. Conservative substitutions of encoded amino acids include, for example, amino acids which belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within the nucleic acids encoding heavy and light chain polypeptides of the invention so long as the nucleic acid or encoded polypeptides retain some or all of their function as described herein.

To generate antibodies of the invention having specific binding activity for a cryptic collagen epitope, the heavy and light chain variable regions of the antibodies HUIV26 and HUI77 were cloned and sequenced (see Example I and FIGS. 2 and 3). CDRs of the heavy and light chain variable regions were identified. Exemplary heavy and light chain CDRs, as determined by the numbering of Kabat, are shown in FIGS. 2C and 3C (underlined). Exemplary heavy and light chain CDRs of HUIV26 include, for example, $V_L$ CDR1, KSSQSLLNSGNQKNYLA (SEQ ID NO:20); $V_L$ CDR2, GASTRES (SEQ ID NO:22); $V_L$ CDR3, QNDHSYPYT (SEQ ID NO:24); $V_H$ CDR1, GFDFSRYWMS (SEQ ID NO:26); $V_H$ CDR2, EINPDSSTINYTPSLKD (SEQ ID NO:28); and $V_H$ CDR3, PVDGYYDAMDY (SEQ ID NO:30). Exemplary heavy and light chain CDRs of HUI77 include, for example, $V_L$ CDR1, RSSQSIVHSNGNTYLE (SEQ ID NO:32); $V_L$ CDR2, KVSNRFS (SEQ ID NO:34); $V_L$ CDR3, FQGSHVPWT (SEQ ID NO:36); $V_H$ CDR1, GFSLSTSGMGVG (SEQ ID NO:38); $V_H$ CDR2, DIWWDDNKYYNPSLKS (SEQ ID NO:40); and $V_H$ CDR3, RANYGNPYYAMDY (SEQ ID NO:42).

Libraries of CDR variants containing single amino acid substitutions were generated (Example II). The libraries were screened for binding to a cryptic collagen site, and single amino acid mutations having beneficial activity were identified. Combinatorial mutants, in which two or more variant CDRs containing at least one amino acid substitution relative to parental HUIV26 or HUI77 CDRs were combined and screened for activity (Example III). A number of combinatorial mutants having optimized activity for binding to a cryptic collagen site were identified.

The antibodies of the invention having binding activity for a cryptic collagen epitope. As disclosed herein, the collagen can be denatured by any of a variety of methods so long as an antigenic determinant is exposed that was less accessible in native collagen. Such methods include, for example, proteolytic digestion, heat or thermal denaturation, chemical denaturation, and the like. One skilled in the art will know a variety of methods suitable for denaturing a collagen molecule to reveal a cryptic collagen site or epitope. Furthermore, the method of denaturation can be a combination of two or more denaturation methods, for example, proteolytic digestion combined with chemical and/or thermal denaturation. For example, proteolytic digestion can be used to cleave collagen, resulting in a collagen molecule that is more susceptible to thermal or chemical denaturation. An exemplary protease that can be used to denature collagen is matrix metalloproteinase, which can be used in vitro and can function in vivo to cleave collagen within triple helical regions and at body temperature in a mammal.

The invention provides grafted antibodies of the HUIV26 and HUI77 antibodies. In one embodiment, the invention provides a grafted antibody of HUIV26. The grafted antibody, or functional fragment thereof, comprises one or more complementarity determining regions (CDRs) having at least one amino acid substitution in one or more CDRs of a heavy chain CDR selected from the group consisting of SEQ ID NOS:26, 28 and 30 or a light chain CDR selected from the group consisting of SEQ ID NOS:20, 22 and 24, the grafted antibody or functional fragment thereof having specific binding activity for a cryptic collagen epitope.

In another embodiment, the invention provides a grafted antibody of HUI77. The grafted antibody, or functional fragment thereof, comprises one or more complementarity determining regions (CDRs) having at least one amino acid substitution in one or more CDRs of a heavy chain CDR selected from the group consisting of SEQ ID NOS:38, 40 and 42 or a light chain CDR selected from the group consisting of SEQ ID NOS:32, 34 and 36, the grafted antibody or functional fragment thereof having specific binding activity for a cryptic collagen epitope.

The invention additionally provides antibodies, or functional fragments thereof, containing specifically recited CDRs, where the antibody or functional fragment thereof has specific binding activity for a cryptic collagen epitope. Such antibodies include those having at least a single amino acid substitution and which retain binding activity for a cryptic collagen epitope. Included among such CDR variants are those described in FIGS. 4 and 5.

Exemplary CDRs of the invention having a single amino acid substitution in a CDR of HUIV26 include, for example, those described below, in which the position of the amino acid mutation in the numbering of Kabat is indicated along with the amino acid substitution from wild type to mutant (wild type→mutant). Such exemplary CDRs include HuIV26 $V_H$ CDR1 31R→H (SEQ ID NO:43); HuIV26 $V_H$ CDR1 34M→I (SEQ ID NO:44); HuIV26 $V_H$ CDR1 35S→T (SEQ ID NO:45); HuIV26 $V_H$ CDR1 35S→A (SEQ ID NO:46); HuIV26 $V_H$ CDR1 35S→G (SEQ ID NO:47); HuIV26 $V_H$ CDR2 57I→A (SEQ ID NO:48); HuIV26 $V_H$ CDR2 57I→S (SEQ ID NO:49); HuIV26 $V_H$ CDR2 62S→Y (SEQ ID NO:50); HuIV26 $V_H$ CDR2 62S→A (SEQ ID NO:51); HuIV26 $V_H$ CDR2 62S→H (SEQ ID NO:52); HuIV26 $V_H$ CDR2 62S→G (SEQ ID NO:53); HuIV26 $V_H$ CDR2 64K→Q (SEQ ID NO:54); HuIV26 $V_H$ CDR2 65D→S (SEQ ID NO:55); HuIV26 $V_H$ CDR3 97D→P (SEQ ID NO:56); HuIV26 $V_H$ CDR3 97D→G (SEQ ID NO:57); HuIV26 $V_H$ CDR3 97D→T (SEQ ID NO:58); HuIV26 $V_H$ CDR3 97D→A (SEQ ID NO:59); HuIV26 $V_H$ CDR3 98G→P (SEQ ID NO:60); HuIV26 $V_H$ CDR3 98G→A (SEQ ID NO:61); HuIV26 $V_H$ CDR3 98G→H (SEQ ID NO:62); HuIV26 $V_H$ CDR3 102Y→P (SEQ ID NO:63); HuIV26 $V_H$ CDR3 102Y→N (SEQ ID NO:64); HuIV26 $V_L$ CDR1 27Q→R (SEQ ID NO:65); HuIV26 $V_L$ CDR1 27Q→S (SEQ ID NO:66); HuIV26 $V_L$ CDR1 27dN→S (SEQ ID NO:67); HuIV26 $V_L$ CDR1 27eS→Y (SEQ ID NO:68); HuIV26 $V_L$ CDR1 27eS→W (SEQ ID NO:69); HuIV26 $V_L$ CDR1 27eS→H (SEQ ID NO:70); HuIV26 $V_L$ CDR1 27eS→R (SEQ ID NO:71); HuIV26 $V_L$ CDR1 27fG→Y (SEQ ID NO:72); HuIV26 $V_L$ CDR1 27fG→R (SEQ ID NO:73); HuIV26 $V_L$ CDR1 27fG→H (SEQ ID NO:74); HuIV26 $V_L$ CDR1 27fG→I (SEQ ID NO:75); HuIV26 $V_L$ CDR1 29Q→K (SEQ ID NO:76); HuIV26 $V_L$ CDR3 93S→Q (SEQ ID NO:77); HuIV26 $V_L$ CDR3 93S→G (SEQ ID NO:78); HuIV26 $V_L$ CDR3 93S→L (SEQ ID NO:79); HuIV26 $V_L$ CDR3 93S→A (SEQ ID NO:80); HuIV26 $V_L$ CDR3 93S→T (SEQ ID NO:81); HuIV26 $V_L$ CDR3 93S→V (SEQ ID NO:82); HuIV26 $V_L$ CDR3 94Y→N (SEQ ID NO:83); HuIV26 $V_L$ CDR3 94Y→S (SEQ ID NO:84); HuIV26 $V_L$ CDR3 94Y→P (SEQ ID NO:85); HuIV26 $V_L$ CDR3 94Y→M (SEQ ID NO:86); and HuIV26 $V_L$ CDR2 57I→V (SEQ ID NO:162).

Exemplary CDRs of the invention having a single amino acid substitution in a CDR of HUI77 include, for example, those described below, in which the position of the amino acid mutation in the numbering of Kabat is indicated along with the amino acid substitution from wild type to mutant (wild type→mutant). Such exemplary CDRs include HUI77 $V_H$ CDR1 32S→P (SEQ ID NO:87); HUI77 $V_H$ CDR1 32S→W (SEQ ID NO:88); HUI77 $V_H$ CDR1 35bG→W (SEQ ID NO:89); HUI77 $V_H$ CDR1 35bG→L (SEQ ID NO:90); HUI77 $V_H$ CDR1 35bG→A (SEQ ID NO:91); HUI77 $V_H$ CDR2 59Y→S (SEQ ID NO:92); HUI77 $V_H$ CDR2 59Y→A (SEQ ID NO:93); HUI77 $V_H$ CDR2 59Y→P (SEQ ID NO:94); HUI77 $V_H$ CDR2 64K→P (SEQ ID NO:95); HUI77 $V_H$ CDR3 95R→P (SEQ ID NO:96); HUI77 $V_H$ CDR3 95R→Q (SEQ ID NO:97); HUI77 $V_H$ CDR3 95R→L (SEQ ID NO:98); HUI77 $V_H$ CDR3 95R→T (SEQ ID NO:99); HUI77 $V_H$ CDR3 95R→V (SEQ ID NO:100); HUI77 $V_H$ CDR3 100N→V (SEQ ID NO:101); HUI77 $V_H$ CDR3 100N→W (SEQ ID NO:102); HUI77 $V_H$ CDR3 100eM→Q (SEQ ID NO:103); HUI77 $V_H$ CDR3 100eM→N (SEQ ID NO:104); HUI77 $V_H$ CDR3 100eM→T (SEQ ID NO:105); HUI77 $V_H$ CDR3 102Y→K (SEQ ID NO:106); HUI77 $V_H$ CDR3 102Y→T (SEQ ID NO:107); HUI77 $V_H$ CDR3 102Y→M (SEQ ID NO:108); HUI77 $V_H$ CDR3 102Y→H (SEQ ID NO:109); HUI77 $V_L$ CDR1 27cV→P (SEQ ID NO:110); HUI77 $V_L$ CDR1 27cV→W (SEQ ID NO:111); HUI77 $V_L$ CDR1 27dH→L (SEQ ID NO:112); HUI77 $V_L$ CDR1 27dH→S (SEQ ID NO:113); HUI77 $V_L$ CDR1 27eS→W (SEQ ID NO:114); HUI77 $V_L$ CDR1 28N→Y (SEQ ID NO:115); HUI77 $V_L$ CDR1 28N→W (SEQ ID NO:116); HUI77 $V_L$ CDR1 30N→Y (SEQ ID NO:117); HUI77 $V_L$ CDR1 33L→F (SEQ ID NO:118); HUI77 $V_L$ CDR1 33L→V (SEQ ID NO:119); HUI77 $V_L$ CDR2 50K→S (SEQ ID NO:120); HUI77 $V_L$ CDR2 51V→A (SEQ ID NO:121); HUI77 $V_L$ CDR2 53N→S (SEQ ID NO:122); HUI77 $V_L$ CDR2 54R→L (SEQ ID NO:123); HUI77 $V_L$ CDR2 56S→W (SEQ ID NO:124); HUI77 $V_L$ CDR2 56S→F (SEQ ID NO:125); HUI77 $V_L$ CDR3 89F→V (SEQ ID NO:126); HUI77 $V_L$ CDR3 89F→H (SEQ ID NO:127); HUI77 $V_L$ CDR3 90Q→R (SEQ ID NO:128); HUI77 $V_L$ CDR3 90Q→W (SEQ ID NO:129); HUI77 $V_L$ CDR3 91G→S (SEQ ID NO:130); HUI77 $V_L$ CDR3 92S→W (SEQ ID NO:131); HUI77 $V_L$ CDR3 92S→E (SEQ ID NO:132); HUI77 $V_L$ CDR3 93H→L (SEQ ID NO:133); HUI77 $V_L$ CDR3 93H→T (SEQ ID NO:134); HUI77 $V_L$ CDR3 93H→S (SEQ ID NO:135); HUI77 $V_L$ CDR3 93H→A (SEQ ID NO:136); HUI77 $V_L$ CDR3 93H→Q (SEQ ID NO:137); HUI77 $V_L$ CDR3 94V→T (SEQ ID NO:138); HUI77 $V_L$ CDR3 97T→A (SEQ ID NO:139); HUI77 $V_L$ CDR3 97T→R (SEQ ID NO:140); HUI77 $V_L$ CDR3 97T→H (SEQ ID NO:141); HUI77 $V_L$ CDR3 97T→K (SEQ ID NO:142); HUI77 $V_L$ CDR3 97T→I (SEQ ID NO:143); HUI77 $V_H$ CDR2 59Y→T (SEQ ID NO:144); HUI77 $V_L$ CDR3 94V→F (SEQ ID NO:145); and HUI77 $V_L$ CDR1 28N→Q (SEQ ID NO:146).

In addition to CDRs having single amino acid substitutions, the invention additionally provides HUIV26 and HUI77 CDRs having two or more amino acid substitutions. Exemplary CDRs having two or more amino acid substitutions in HUIV26 include, for example, HUIV26 $V_H$ CDR2 57I→A/62S→A (SEQ ID NO:154); HUIV26 $V_H$ CDR2 57I→A/62S→Y (SEQ ID NO:155); HUIV26 $V_H$ CDR2 57I→A/62S→H (SEQ ID NO:156); HUIV26 $V_L$ CDR1 27eS→W/27fG→Y (SEQ ID NO:157); HUIV26 $V_L$ CDR1 27eS→Y/27fG→Y (SEQ ID NO:158); HUIV26 $V_L$ CDR1 27eS→Y/27fG→H (SEQ ID NO:159); HUIV26 $V_L$ CDR1 27eS→R/27fG→Y (SEQ ID NO:160); and HUIV26 $V_L$ CDR1 27eS→W/27fG→H (SEQ ID NO:161) (see FIG. 6). Exemplary CDRs having two or more amino acid substitutions in HUI77 include, for example, HUI77 $V_H$ CDR1 32S→P/35bG→W (SEQ ID NO:147); HUI77 CDR1 32S→P/35bG→A (SEQ ID NO:148); HUI77 $V_L$ CDR1 27dH→S/28N→W (SEQ ID NO:149); HUI77 $V_L$ CDR1 27dH→S/28N→Y (SEQ ID NO:150); HUI77 $V_L$ CDR1 27dH→S/28N→Q (SEQ ID NO:151); HUI77 $V_L$ CDR1 28N→Q/33L→F (SEQ ID NO:152); and HUI77 $V_L$ CDR1 27H→S/28N→W/33L→F (SEQ ID NO:153) (see FIG. 7).

The invention provides an antibody having at least one of the above variant CDR sequences. It is understood that any combination of HUIV26 CDRs can be combined with mutant and/or wild type CDRs to generate an HUIV26 grafted antibody, so long as binding activity to a cryptic collagen site is maintained. Similarly, any combination of HUI77 CDRs can be combined with mutant and/or wild type CDRs to generate a HUI77 grafted antibody so long as binding activity to a cryptic collagen site is maintained. Thus, any combination of single amino acid substitutions can be combined with other CDR mutants to generate an antibody having at least two variant CDRs. Furthermore, any single mutation at different positions within the same CDR can be combined to generate a CDR having 2 or more amino acid substitutions at two or more positions. Any of the single or multiple mutations can be combined so long as binding activity to a cryptic collagen site is maintained.

Thus, the invention provides an antibody, or functional fragment thereof, comprising one or more CDRs selected from the group consisting of CDRs referenced as SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78; SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:154, SEQ ID NO:155, SEQ ID NO:156, SEQ ID NO:157, SEQ ID NO:158, SEQ ID NO:159, SEQ ID NO:160, SEQ ID NO:161, and SEQ ID NO:162, the antibody or functional fragment thereof having specific binding activity for a cryptic collagen epitope.

The invention additionally provides an antibody, or functional fragment thereof, comprising one or more CDRs selected from the group consisting of CDRs referenced as SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, and SEQ ID NO:153, the antibody or functional fragment thereof having specific binding activity for a cryptic collagen epitope.

The invention further provides an antibody, or functional fragment thereof, comprising a heavy chain polypeptide comprising one or more CDRs having at least one amino acid substitution in one or more heavy chain CDRs, the heavy chain CDRs selected from the group consisting of a heavy chain CDR1 selected from the group consisting of CDRs referenced as SEQ ID NOS:26, 43, 44, 45, 46, and 47; a heavy chain CDR2 selected from the group consisting of CDRs referenced as SEQ ID NOS:28, 48, 49, 50, 51, 52, 53, 54, and 55; and a heavy chain CDR3 selected from the group consisting of CDRs referenced as SEQ ID NOS:30, 56, 57, 58, 59, 60, 61, 62, 63, and 64, the antibody or functional fragment thereof having specific binding activity for a cryptic collagen epitope.

The invention also provides an antibody, or functional fragment thereof, comprising a light chain polypeptide comprising one or more CDRs having at least one amino acid substitution in one or more light chain CDRs, the light chain CDRs selected from the group consisting of a light chain CDR1 selected from the group consisting of CDRs referenced as SEQ ID NOS:20, 65, 66, 67, 68, 69, 70, 71, 72, 73, 74, 75, and 76; a light chain CDR2 referenced as SEQ ID NO:22:; and a light chain CDR3 selected from the group consisting of CDRs referenced as SEQ ID NOS:24, 77, 78, 79, 80, 81, 82, 83, 84, 85, and 86, the antibody or functional fragment thereof having specific binding activity for a cryptic collagen epitope.

The invention further provides an antibody, or functional fragment thereof, comprising a heavy chain polypeptide comprising one or more CDRs having at least one amino acid substitution in one or more heavy chain CDRs, the heavy chain CDRs selected from the group consisting of a heavy chain CDR1 selected from the group consisting of CDRs referenced as SEQ ID NOS:38, 87, 88, 89, 90, 91, 147 and 148; a heavy chain CDR2 selected from the group consisting of CDRs referenced as SEQ ID NOS:40, 92, 93, 94, 95 and 144; and a heavy chain CDR3 selected from the group consisting of CDRs referenced as SEQ ID NOS:42, 96, 97, 98, 99, 100, 101, 102, 103, 104, 105, 106, 107, 108 and 109, the antibody or functional fragment thereof having specific binding activity for a cryptic collagen epitope.

Additionally provided is an antibody, or functional fragment thereof, comprising a light chain polypeptide comprising one or more CDRs having at least one amino acid substitution in one or more light chain CDRs, the light chain CDRs selected from the group consisting of a light chain CDR1 selected from the group consisting of CDRs referenced as SEQ ID NOS:32, 110, 111, 112, 113, 114, 115, 116, 117, 118, 119, 146, 149, 150, 151, 152 and 153; a light chain CDR2 referenced as SEQ ID NOS:34, 120, 121, 122, 123, 124 and 125; and a light chain CDR3 selected from the group consisting of CDRs referenced as SEQ ID NOS:36, 126, 127, 128, 129, 130, 131, 132, 133, 134, 135, 136, 137, 138, 139, 140, 141, 142, 143, and 145, the antibody or functional fragment thereof having specific binding activity for a cryptic collagen epitope.

As described above, an antibody of the invention can be generated from any combination of the variant and/or wild type CDRs, so long as binding activity to a cryptic collagen site is maintained. As disclosed herein, a variety of combinatorial antibodies containing multiple CDRs having at least a single amino acid substitution were identified having binding activity for a cryptic collagen site. In addition to antibodies containing any combination of the respective CDRs disclosed herein, the following specific combinations of CDRs are also provided by the invention.

Exemplary HUIV26 variants include, for example, the following antibodies:

An antibody comprising a heavy chain CDR1 referenced as SEQ ID NO:26; a heavy chain CDR2 referenced as SEQ ID NO:28; a heavy chain CDR3 referenced as SEQ ID NO:63; a light chain CDR1 referenced as SEQ ID NO:20; a light chain CDR2 referenced as SEQ ID NO:22; and a light chain CDR3 referenced as SEQ ID NO:77 (4.1-2D4).

An antibody comprises a heavy chain CDR1 referenced as SEQ ID NO:26; a heavy chain CDR2 referenced as SEQ ID NO:28; a heavy chain CDR3 referenced as SEQ ID NO:63; a light chain CDR1 referenced as SEQ ID NO:72; a light chain CDR2 referenced as SEQ ID NO:22; and a light chain CDR3 referenced as SEQ ID NO:77 (L1b-F11).

An antibody comprising a heavy chain CDR1 referenced as SEQ ID NO:26; a heavy chain CDR2 referenced as SEQ ID NO:48; a heavy chain CDR3 referenced as SEQ ID NO:63; a light chain CDR1 referenced as SEQ ID NO:20; a light chain CDR2 referenced as SEQ ID NO:22; and a light chain CDR3 referenced as SEQ ID NO:77 (H2a-G8).

An antibody comprising a heavy chain CDR1 referenced as SEQ ID NO:45; a heavy chain CDR2 referenced as SEQ ID NO:154; a heavy chain CDR3 referenced as SEQ ID NO:63; a light chain CDR1 referenced as SEQ ID NO:157; a light chain CDR2 referenced as SEQ ID NO:22; and a light chain CDR3 referenced as SEQ ID NO:77 (DcomA2).

An antibody comprising a heavy chain CDR1 referenced as SEQ ID NO:26; a heavy chain CDR2 referenced as SEQ ID NO:155; a heavy chain CDR3 referenced as SEQ ID NO:63; a light chain CDR1 referenced as SEQ ID NO:158; a light chain CDR2 referenced as SEQ ID NO:22; and a light chain CDR3 referenced as SEQ ID NO:77 (DcomA4).

An antibody comprising a heavy chain CDR1 referenced as SEQ ID NO:46; a heavy chain CDR2 referenced as SEQ ID NO:155; a heavy chain CDR3 referenced as SEQ ID NO:63; a light chain CDR1 referenced as SEQ ID NO:159; a light chain CDR2 referenced as SEQ ID NO:22; and a light chain CDR3 referenced as SEQ ID NO:77 (DcomB1).

An antibody comprising a heavy chain CDR1 referenced as SEQ ID NO:26; a heavy chain CDR2 referenced as SEQ ID NO:48; a heavy chain CDR3 referenced as SEQ ID NO:63; a light chain CDR1 referenced as SEQ ID NO:160; a light chain CDR2 referenced as SEQ ID NO:22; and a light chain CDR3 referenced as SEQ ID NO:77 (DcomD2).

An antibody comprising a heavy chain CDR1 referenced as SEQ ID NO:45; a heavy chain CDR2 referenced as SEQ ID NO:155; a heavy chain CDR3 referenced as SEQ ID NO:63; a light chain CDR1 referenced as SEQ ID NO:72; a light chain CDR2 referenced as SEQ ID NO:22; and a light chain CDR3 referenced as SEQ ID NO:77 (DcomD3).

An antibody comprising a heavy chain CDR1 referenced as SEQ ID NO:26; a heavy chain CDR2 referenced as SEQ ID NO:155; a heavy chain CDR3 referenced as SEQ ID NO:63; a light chain CDR1 referenced as SEQ ID NO:157; a light chain CDR2 referenced as SEQ ID NO:22; and a light chain CDR3 referenced as SEQ ID NO:77 (DcomD6).

An antibody comprising a heavy chain CDR1 referenced as SEQ ID NO:45; a heavy chain CDR2 referenced as SEQ ID NO:155; a heavy chain CDR3 referenced as SEQ ID NO:63; a light chain CDR1 referenced as SEQ ID NO:160; a light chain CDR2 referenced as SEQ ID NO:22; and a light chain CDR3 referenced as SEQ ID NO:77 (DcomE3).

An antibody comprising a heavy chain CDR1 referenced as SEQ ID NO:46; a heavy chain CDR2 referenced as SEQ ID NO:155; a heavy chain CDR3 referenced as SEQ ID NO:63; a light chain CDR1 referenced as SEQ ID NO:160; a light chain CDR2 referenced as SEQ ID NO:22; and a light chain CDR3 referenced as SEQ ID NO:77 (DcomG2).

An antibody comprising a heavy chain CDR1 referenced as SEQ ID NO:45; a heavy chain CDR2 referenced as SEQ ID NO:162; a heavy chain CDR3 referenced as SEQ ID NO:63; a light chain CDR1 referenced as SEQ ID NO:158; a light chain CDR2 referenced as SEQ ID NO:22; and a light chain CDR3 referenced as SEQ ID NO:77 (DcomA7).

An antibody comprising a heavy chain CDR1 referenced as SEQ ID NO:45; a heavy chain CDR2 referenced as SEQ ID NO:156; a heavy chain CDR3 referenced as SEQ ID NO:63; a light chain CDR1 referenced as SEQ ID NO:157; a light chain CDR2 referenced as SEQ ID NO:22; and a light chain CDR3 referenced as SEQ ID NO:77 (DcomB10).

An antibody comprising a heavy chain CDR1 referenced as SEQ ID NO:26; a heavy chain CDR2 referenced as SEQ ID NO:154; a heavy chain CDR3 referenced as SEQ ID NO:63; a light chain CDR1 referenced as SEQ ID NO:157; a light chain CDR2 referenced as SEQ ID NO:22; and a light chain CDR3 referenced as SEQ ID NO:77 (DcomC8).

An antibody comprising a heavy chain CDR1 referenced as SEQ ID NO:45; a heavy chain CDR2 referenced as SEQ ID NO:155; a heavy chain CDR3 referenced as SEQ ID NO:63; a light chain CDR1 referenced as SEQ ID NO:157; a light chain CDR2 referenced as SEQ ID NO:22; and a light chain CDR3 referenced as SEQ ID NO:77 (DcomD7).

An antibody comprising a heavy chain CDR1 referenced as SEQ ID NO:46; a heavy chain CDR2 referenced as SEQ ID NO:154; a heavy chain CDR3 referenced as SEQ ID NO:63; a light chain CDR1 referenced as SEQ ID NO:161; a light chain CDR2 referenced as SEQ ID NO:22; and a light chain CDR3 referenced as SEQ ID NO:77 (DcomD11).

An antibody comprising a heavy chain CDR1 referenced as SEQ ID NO:46; a heavy chain CDR2 referenced as SEQ ID NO:156; a heavy chain CDR3 referenced as SEQ ID NO:63; a light chain CDR1 referenced as SEQ ID NO:161; a light chain CDR2 referenced as SEQ ID NO:22; and a light chain CDR3 referenced as SEQ ID NO:77 (DcomE11).

An antibody comprising a heavy chain CDR1 referenced as SEQ ID NO:46; a heavy chain CDR2 referenced as SEQ ID NO:28; a heavy chain CDR3 referenced as SEQ ID NO:63; a light chain CDR1 referenced as SEQ ID NO:20; a light chain CDR2 referenced as SEQ ID NO:22; and a light chain CDR3 referenced as SEQ ID NO:77 (2D4H1-C3).

Exemplary HUI77 variants include, for example, the following antibodies:

An antibody comprising a heavy chain CDR1 referenced as SEQ ID NO:38; a heavy chain CDR2 referenced as SEQ ID NO:40; a heavy chain CDR3 referenced as SEQ ID NO:103; a light chain CDR1 referenced as SEQ ID NO:32; a light chain CDR2 referenced as SEQ ID NO:34; and a light chain CDR3 referenced as SEQ ID NO:36 (12F10Q).

An antibody comprising a heavy chain CDR1 referenced as SEQ ID NO:38; a heavy chain CDR2 referenced as SEQ ID NO:92; a heavy chain CDR3 referenced as SEQ ID NO:103; a light chain CDR1 referenced as SEQ ID NO:32; a light chain CDR2 referenced as SEQ ID NO:34; and a light chain CDR3 referenced as SEQ ID NO:36 (QH2b-A3).

An antibody comprising a heavy chain CDR1 referenced as SEQ ID NO:147; a heavy chain CDR2 referenced as SEQ ID NO:92; a heavy chain CDR3 referenced as SEQ ID NO:103; a light chain CDR1 referenced as SEQ ID NO:149; a light chain CDR2 referenced as SEQ ID NO:34; and a light chain CDR3 referenced as SEQ ID NO:36 (Qcom1B6).

An antibody comprising a heavy chain CDR1 referenced as SEQ ID NO:147; a heavy chain CDR2 referenced as SEQ ID NO:92; a heavy chain CDR3 referenced as SEQ ID NO:103; a light chain CDR1 referenced as SEQ ID NO:150; a light chain CDR2 referenced as SEQ ID NO:34; and a light chain CDR3 referenced as SEQ ID NO:36 (Qcom1B8).

An antibody comprising a heavy chain CDR1 referenced as SEQ ID NO:147; a heavy chain CDR2 referenced as SEQ ID NO:93; a heavy chain CDR3 referenced as SEQ ID NO:103; a light chain CDR1 referenced as SEQ ID NO:149; a light chain CDR2 referenced as SEQ ID NO:34; and a light chain CDR3 referenced as SEQ ID NO:36 (Qcom1C3).

An antibody comprising a heavy chain CDR1 referenced as SEQ ID NO:147; a heavy chain CDR2 referenced as SEQ ID NO:144; a heavy chain CDR3 referenced as SEQ ID NO:103; a light chain CDR1 referenced as SEQ ID NO:149; a light chain CDR2 referenced as SEQ ID NO:34; and a light chain CDR3 referenced as SEQ ID NO:36 (Qcom1D3).

An antibody comprising a heavy chain CDR1 referenced as SEQ ID NO:147; a heavy chain CDR2 referenced as SEQ ID NO:93; a heavy chain CDR3 referenced as SEQ ID NO:103; a light chain CDR1 referenced as SEQ ID NO:151; a light chain CDR2 referenced as SEQ ID NO:34; and a light chain CDR3 referenced as SEQ ID NO:36 (Qcom1E3).

An antibody comprising a heavy chain CDR1 referenced as SEQ ID NO:147; a heavy chain CDR2 referenced as SEQ ID NO:92; a heavy chain CDR3 referenced as SEQ ID NO:103; a light chain CDR1 referenced as SEQ ID NO:151; a light chain CDR2 referenced as SEQ ID NO:34; and a light chain CDR3 referenced as SEQ ID NO:36 (Qcom1H6).

An antibody comprising a heavy chain CDR1 referenced as SEQ ID NO:147; a heavy chain CDR2 referenced as SEQ ID NO:93; a heavy chain CDR3 referenced as SEQ ID NO:103; a light chain CDR1 referenced as SEQ ID NO:152; a light chain CDR2 referenced as SEQ ID NO:34; and a light chain CDR3 referenced as SEQ ID NO:145 (Qcom1H7).

An antibody comprising a heavy chain CDR1 referenced as SEQ ID NO:148; a heavy chain CDR2 referenced as SEQ ID NO:93; a heavy chain CDR3 referenced as SEQ ID NO:103; a light chain CDR1 referenced as SEQ ID NO:150; a light chain CDR2 referenced as SEQ ID NO:34; and a light chain CDR3 referenced as SEQ ID NO:36 (Qcom2A4).

An antibody comprising a heavy chain CDR1 referenced as SEQ ID NO:147; a heavy chain CDR2 referenced as SEQ ID NO:93; a heavy chain CDR3 referenced as SEQ ID NO:103; a light chain CDR1 referenced as SEQ ID NO:115; a light chain CDR2 referenced as SEQ ID NO:34; and a light chain CDR3 referenced as SEQ ID NO:36 (Qcom2B11).

An antibody comprising a heavy chain CDR1 referenced as SEQ ID NO:147; a heavy chain CDR2 referenced as SEQ ID NO:40; a heavy chain CDR3 referenced as SEQ ID NO:103; a light chain CDR1 referenced as SEQ ID NO:153; a light chain CDR2 referenced as SEQ ID NO:34; and a light chain CDR3 referenced as SEQ ID NO:36 (Qcom2C1).

An antibody comprising a heavy chain CDR1 referenced as SEQ ID NO:147; a heavy chain CDR2 referenced as SEQ ID NO:92; a heavy chain CDR3 referenced as SEQ ID NO:103; a light chain CDR1 referenced as SEQ ID NO:116; a light chain CDR2 referenced as SEQ ID NO:34; and a light chain CDR3 referenced as SEQ ID NO:36 (Qcom2D9).

An antibody comprising a heavy chain CDR1 referenced as SEQ ID NO:147; a heavy chain CDR2 referenced as SEQ ID NO:93; a heavy chain CDR3 referenced as SEQ ID NO:103; a light chain CDR1 referenced as SEQ ID NO:116; a light chain CDR2 referenced as SEQ ID NO:34; and a light chain CDR3 referenced as SEQ ID NO:36 (Qcom2E3).

An antibody comprising a heavy chain CDR1 referenced as SEQ ID NO:38; a heavy chain CDR2 referenced as SEQ ID NO:93; a heavy chain CDR3 referenced as SEQ ID NO:103; a light chain CDR1 referenced as SEQ ID NO:32; a light chain CDR2 referenced as SEQ ID NO:34; and a light chain CDR3 referenced as SEQ ID NO:36 (Qh2b-B7).

The invention also provides grafted antibodies containing CDRs derived from HUIV26 and HUI77, respectively. Such grafted CDRs include humanized antibodies, in which CDRs from HUIV26 or HUI77 have been grafted or in which a CDR containing one or more amino acid substitutions is grafted. The CDRs can be grafted directly into a human framework, as disclosed herein. If desired, framework changes can also be incorporated by generating framework libraries. The optimization of CDRs and/or framework sequences can be performed independently and sequentially combined or can be performed simultaneously, as described in more detail below.

Thus, the invention additionally provides a grafted antibody in which HUIV26 CDRs (SEQ ID NOS:20, 22, 24, 26, 28 and 30) are grafted into a human framework sequence. Also provided is a grafted antibody in which HUI77 CDRs (SEQ ID NOS:32, 34, 36, 38, 40 and 42) are grafted into a human framework.

To generate grafted antibodies, donor CDRs of collagen-specific antibodies are grafted onto an antibody acceptor variable region framework. Methods for grafting antibodies and generating CDR variants to optimize activity have been described previously (WO 98/33919; WO 00/78815; WO 01/27160). The procedure can be performed to achieve grafting of donor CDRs and affinity reacquisition in a simultaneous process. The methods similarly can be used, either alone or in combination with CDR grafting, to modify or optimize the binding affinity of a variable region. The methods for conferring donor CDR binding affinity onto an acceptor variable region are applicable to both heavy and light chain variable regions and as such can be used to simultaneously graft and optimize the binding affinity of an antibody variable region.

The donor CDRs can be altered to contain a plurality of different amino acid residue changes at all or selected positions within the donor CDRs. For example, random or biased incorporation of the twenty naturally occurring amino acid residues, or preselected subsets, can be introduced into the donor CDRs to produce a diverse population of CDR species. Inclusion of CDR variant species into the diverse population of variable regions allows for the generation of variant species that exhibit optimized binding affinity for a predetermined antigen.

A range of possible changes can be made in the donor CDR positions. Some or all of the possible changes that can be selected for change can be introduced into the population of grafted donor CDRs. A single position in a CDR can be selected to introduce changes or a variety of positions having altered amino acids can be combined and screened for activity.

One approach is to change all amino acid positions along a CDR by replacement at each position with, for example, all twenty naturally occurring amino acids. The replacement of each position can occur in the context of other donor CDR amino acid positions so that a significant portion of the CDR maintains the authentic donor CDR sequence, and therefore, the binding affinity of the donor CDR. For example, an acceptor variable region framework, either a native or altered framework, can be grafted with a population of CDRs containing single position replacements at each position within the CDRs. Similarly, an acceptor variable region framework can be targeted for grafting with a population of CDRs containing more than one position changed to incorporate all twenty amino acid residues, or a subset of amino acids. One or more amino acid positions within a CDR, or within a group of CDRs to be grafted, can be altered and grafted into an acceptor variable region framework to generate a population of grafted antibodies. It is understood that a CDR having one or more altered positions can be combined with one or more other CDRs having one or more altered positions, if desired.

A population of CDR variant species having one or more altered positions can be combined with any or all of the CDRs which constitute the binding pocket of a variable region. Therefore, an acceptor variable region framework can be targeted for the simultaneous incorporation of donor CDR variant populations at one, two or all three recipient CDR locations in a heavy or light chain. The choice of which CDR or the number of CDRs to target with amino acid position changes will depend on, for example, if a full CDR grafting into an acceptor is desired or whether the method is being performed for optimization of binding affinity.

Another approach for selecting donor CDR amino acids to change for conferring donor CDR binding affinity onto an antibody acceptor variable region framework is to select known or readily identifiable CDR positions that are highly variable. For example, the variable region CDR3 is generally highly variable. This region therefore can be selectively targeted for amino acid position changes during grafting procedures to ensure binding affinity reacquisition or augmentation, either alone or together with relevant acceptor variable framework changes, as described herein.

If desired, CDR variant populations having one or more altered amino acid positions can be advantageously combined with a framework variant population having one or more altered amino acid positions. Such a combination can result in beneficial combinations of changes, which are identified by screening for an optimized activity.

The resultant population of CDR grafted variable regions therefore contain a species corresponding to the authentic parent amino acid residue at each position as well as a diverse number of different species which correspond to the possible combinations and permutations of the authentic parent amino acid residues together with the variant residues at each of the selected CDR positions. Such a diverse population of CDR grafted variable regions are screened for an altered variable region species which retains donor CDR binding activity, or which has optimized binding activity.

An acceptor can be selected so that it is closely similar to the variable region amino acid sequence harboring the donor CDRs. In addition, a variety of acceptors less closely related to the donor antibody can be used. Alternatively, a library of all possible or relevant changes in the acceptor framework can be made and then screened for those variable regions, or heteromeric binding fragments thereof, that maintain or exhibit increased binding affinity compared to the donor molecule. The donor CDRs can be grafted into a variety of naturally occurring acceptor frameworks or altered frameworks having one or more changes or even a library containing changes at one or more positions. Therefore, the applicability is not preconditioned on the availability or search for an acceptor framework variable region similar to that of the donor.

The methods for conferring donor CDR binding affinity onto a variable region can involve identifying the relevant amino acid positions in the acceptor framework that are known or predicted to influence a CDR conformation, or that are known or predicted to influence the spacial context of amino acid side chains within the CDR that participate in binding, and then generating a population of altered variable region species that incorporate a plurality of different amino acid residues at those positions. For example, the different amino acid residues at those positions can be incorporated either randomly or with a predetermined bias and can include all of the twenty naturally occurring amino acid residues at each of the relevant positions. Subsets, including less than all of the naturally occurring amino acids can additionally be chosen for incorporation at the relevant framework positions. Including a plurality of different amino acid residues at each of the relevant framework positions ensures that there will be at least one species within the population that will have framework changes which allows the CDRs to reacquire their donor binding affinity in the context of the acceptor framework variable region.

For humanizing an antibody, any of a variety of human frameworks can be selected for CDR grafting. For example, CDRs of HUIV26 or HUI77 can be cloned into a variety of human framework sequences. The frameworks can be generated using human germline genes encoding heavy and light chain variable regions as well as J regions to obtain human framework sequences for CDR grafting. Exemplary human framework nucleotide sequences include, for example, the framework sequences of DPK24 (VKIV) (SEQ ID NO:5), DP-54 (VHIII) (SEQ ID NO:7), DPK13 (VKII) (SEQ ID NO:13), DP-28 (VHII) (SEQ ID NO:15), as well as J regions JK1 (SEQ ID NO:217), JK2 (SEQ ID NO:218) and JH6 (SEQ ID NO:219). It is understood that framework regions from any available germline sequence can be combined with any available J sequence, as desired, to generate a human framework for grafting CDRs. For example, an alignment of mouse variable regions of HUIV26 and HUI77 with an exemplary human framework is shown in FIGS. 2C and 3C, respectively. A fusion of VKIV/JK2 light chain variable region and VHIII/JH6 heavy chain variable region are aligned with HUIV26 (FIG. 2C). A fusion of VKII/JK1 light chain variable region and VHIII/JH6 heavy chain variable region are aligned with HUI77 (FIG. 3C). An exemplary fusion of a germline and J region is shown in FIG. 3D, which is aligned with the HUI77 light chain. It is understood that any available human framework can be selected for CDR grafting and, if desired, optimized by the methods disclosed herein. As disclosed herein, CDRs having beneficial mutations can be grafted into a variety of frameworks and have retained or improved activity (see Example III).

Selection of the relevant framework amino acid positions to alter depends on a variety of criteria well known to those skilled it the art. One criteria for selecting relevant framework amino acids to change can be the relative differences in amino acid framework residues between the donor and acceptor molecules. Selection of relevant framework positions to alter using this approach is simple and has the advantage of avoiding any subjective bias in residue determination or any bias in CDR binding affinity contribution by the residue.

Another criteria that can be used for determining the relevant amino acid positions to change can be, for example, selection of framework residues that are known to be important or to contribute to CDR conformation. For example, canonical framework residues are important for CDR conformation or structure. Targeting of a canonical framework residue as a relevant position to change can identify a more compatible amino acid residue in context with its associated donor CDR sequence.

The frequency of an amino acid residue at a particular framework position is another criteria which can be used for selecting relevant framework amino acid positions to change. For example, comparison of the selected framework with other framework sequences within its subfamily can reveal residues that occur at minor frequencies at a particular position or positions. Such positions harboring less abundant residues are similarly applicable for selection as a position to alter in the acceptor variable region framework.

The relevant amino acid positions to change also can be selected, for example, based on proximity to a CDR. In certain contexts, such residues can participate in CDR conformation or antigen binding. Moreover, this criteria can similarly be used to prioritize relevant positions selected by other criteria described herein. Therefore, differentiating between residues proximal and distal to one or more CDRs is an efficient way to reduce the number of relevant positions to change.

Other criteria for selecting relevant amino acid framework positions to alter include, for example, residues that are known or predicted to reside in three dimensional space near the antigen-CDR interface or predicted to modulate CDR activity. Similarly, framework residues that are known or predicted to form contacts between the heavy ($V_H$) and light ($V_L$) chain variable region interface can be selected. Such framework positions can affect the conformation or affinity of a CDR by modulating the CDR binding pocket, antigen interaction or the $V_H$ and $V_L$ interaction. Therefore, selection of these amino acid positions for constructing a diverse population for screening of binding activity can be used to identify framework changes which replace residues having detrimental effects on CDR conformation or compensate for detrimental effects of residues occurring elsewhere in the framework.

Other framework residues that can be selected for alteration include amino acid positions that are inaccessible to solvent. Such residues are generally buried in the variable region and are therefore capable of influencing the conformation of the CDR or $V_H$ and $V_L$ interactions. Solvent accessibility can be predicted, for example, from the relative hydrophobicity of the environment created by the amino acid side chains of the polypeptide or by known three-dimensional structural data.

Following selection of relevant amino acid positions in the donor CDRs, as well as any relevant amino acid positions in the framework regions desired to be varied, amino acid changes at some or all of the selected positions can be incorporated into encoding nucleic acids for the acceptor variable region framework and donor CDRs. Altered framework or CDR sequences can be individually made and tested, or can be simultaneously combined and tested, if desired.

The variability at any or all of the altered positions can range from a few to a plurality of different amino acid residues, including all twenty naturally occurring amino acids or functional equivalents and analogues thereof.

Selection of the number and location of the amino acid positions to vary is flexible and can depend on the intended use and desired efficiency for identification of the altered variable region having a desirable activity such as substantially the same or greater binding affinity compared to the donor variable region. In this regard, the greater the number of changes that are incorporated into a altered variable region population, the more efficient it is to identify at least one species that exhibits a desirable activity, for example, substantially the same or greater binding affinity as the donor. Alternatively, where the user has empirical or actual data to the affect that certain amino acid residues or positions contribute disproportionally to binding affinity, then it can be desirable to produce a limited population of altered variable regions which focuses on changes within or around those identified residues or positions.

For example, if CDR grafted variable regions are desired, a large, diverse population of altered variable regions can include all the non-identical framework region positions between the donor and acceptor framework and all single CDR amino acid position changes. Alternatively, a population of intermediate diversity can include subsets, for example, of only the proximal non-identical framework positions to be incorporated together with all single CDR amino acid position changes. The diversity of the above populations can be further increased by, for example, additionally including all pairwise CDR amino acid position changes. In contrast, populations focusing on predetermined residues or positions which incorporate variant residues at as few as one framework and/or one CDR amino acid position can similarly be constructed for screening and identification of an altered antibody variable region of the invention. As with the above populations, the diversity of such focused populations can be further increased by additionally expanding the positions selected for change to include other relevant positions in either or both of the framework and CDR regions. There are numerous other combinations ranging from few changes to many changes in either or both of the framework regions and CDRs that can additionally be employed, all of which will result in a population of altered variable regions that can be screened for the identification of at least one CDR grafted altered variable region having desired activity, for example, binding activity to a cryptic collagen site. Those skilled in the art will know, or can determine, which selected residue positions in the framework or donor CDRs, or subsets thereof, can be varied to produce a population for screening and identification of an altered antibody of the invention given the teachings and guidance provided herein.

Simultaneous incorporation of all of the CDR encoding nucleic acids and all of the selected amino acid position changes can be accomplished by a variety of methods known to those skilled in the art, including for example, recombinant and chemical synthesis. For example, simultaneous incorporation can be accomplished by, for example, chemically synthesizing the nucleotide sequence for the acceptor variable region, fused together with the donor CDR encoding nucleic acids, and incorporating at the positions selected for harboring variable amino acid residues a plurality of corresponding amino acid codons.

One such method well known in the art for rapidly and efficiently producing a large number of alterations in a known amino acid sequence or for generating a diverse population of variable or random sequences is known as codon-based synthesis or mutagenesis. This method is the subject matter of U.S. Pat. Nos. 5,264,563 and 5,523,388 and is also described in Glaser et al. *J. Immunology* 149:3903 (1992). Briefly, coupling reactions for the randomization of, for example, all twenty codons which specify the amino acids of the genetic code are performed in separate reaction vessels and randomization for a particular codon position occurs by mixing the products of each of the reaction vessels. Following mixing, the randomized reaction products corresponding to codons encoding an equal mixture of all twenty amino acids are then divided into separate reaction vessels for the synthesis of each randomized codon at the next position. For the synthesis of equal frequencies of all twenty amino acids, up to two codons can be synthesized in each reaction vessel.

Variations to these synthesis methods also exist and include for example, the synthesis of predetermined codons at desired positions and the biased synthesis of a predetermined sequence at one or more codon positions. Biased synthesis involves the use of two reaction vessels where the predetermined or parent codon is synthesized in one vessel and the random codon sequence is synthesized in the second vessel. The second vessel can be divided into multiple reaction vessels such as that described above for the synthesis of codons specifying totally random amino acids at a particular position. Alternatively, a population of degenerate codons can be synthesized in the second reaction vessel such as through the coupling of NNG/T nucleotides where N is a mixture of all four nucleotides. Following synthesis of the predetermined and random codons, the reaction products in each of the two reaction vessels are mixed and then redivided into an additional two vessels for synthesis at the next codon position.

A modification to the above-described codon based synthesis for producing a diverse number of variant sequences can similarly be employed for the production of the variant populations described herein. This modification is based on the two vessel method described above, which biases synthesis toward the parent sequence and allows the user to separate the variants into populations containing a specified number of codon positions that have random codon changes.

Briefly, this synthesis is performed by continuing to divide the reaction vessels after the synthesis of each codon position into two new vessels. After the division, the reaction products from each consecutive pair of reaction vessels, starting with the second vessel, is mixed. This mixing brings together the reaction products having the same number of codon positions with random changes. Synthesis proceeds by then dividing the products of the first and last vessel and the newly mixed products from each consecutive pair of reaction vessels and redividing into two new vessels. In one of the new vessels, the parent codon is synthesized and in the second vessel, the random codon is synthesized. For example, synthesis at the first codon position entails synthesis of the parent codon in one reaction vessel and synthesis of a random codon in the second reaction vessel. For synthesis at the second codon position, each of the first two reaction vessels is divided into two vessels yielding two pairs of vessels. For each pair, a parent codon is synthesized in one of the vessels and a random codon is synthesized in the second vessel. When arranged linearly, the reaction-products in the second and third vessels are mixed to bring together those products having random codon sequences at single codon positions. This mixing also reduces the product populations to three, which are the starting populations for the next round of synthesis. Similarly, for the third, fourth and each remaining position, each reaction product population for the preceding position are divided and a parent and random codon synthesized.

Following the above modification of codon-based synthesis, populations containing random codon changes at one, two, three and four positions as well as others can be conveniently separated out and used based on the need of the individual. Moreover, this synthesis scheme also allows enrichment of the populations for the randomized sequences over the parent sequence since the vessel containing only the parent sequence synthesis is similarly separated out from the random codon synthesis.

Other methods well known in the art for producing a large number of alterations in a known amino acid sequence or for generating a diverse population of variable or random sequences include, for example, degenerate or partially degenerate oligonucleotide synthesis. Codons specifying equal mixtures of all four nucleotide monomers, represented as NNN, results in degenerate synthesis. Whereas partially degenerate synthesis can be accomplished using, for example, the NNG/T codon described previously. Other methods well known in the art can alternatively be used such as the use of statistically predetermined, or varigated, codon synthesis, which is the subject matter of U.S. Pat. Nos. 5,223, 409 and 5,403,484.

Once the populations of altered variable region encoding nucleic acids have been constructed as described above, they can be expressed to generate a population of altered variable region polypeptides that can be screened for binding affinity. For example, the altered variable region encoding nucleic acids can be cloned into an appropriate vector for propagation, manipulation and expression. Such vectors are known or can be constructed by those skilled in the art and should contain all expression elements sufficient for the transcription, translation, regulation, and if desired, sorting and secretion of the altered variable region polypeptides. The vectors can be suitable for expression in either procaryotic or eukaryotic host systems so long as the expression and regulatory elements function in the respective host system. The expression vectors can additionally include regulatory elements for inducible or cell type-specific expression. One skilled in the art will know which host systems are compatible with a particular vector and which regulatory or functional elements are sufficient to achieve expression of the polypeptides in soluble, secreted or cell surface forms.

Appropriate host cells, include for example, bacteria and corresponding bacteriophage expression systems, yeast, avian, insect and mammalian cells. Methods for recombinant expression, screening and purification of populations of altered variable regions or altered variable region polypeptides within such populations in various host systems are well known in the art and are described, for example, in Sambrook et al., *Molecular Cloning: A Laboratory Manual*, Cold Spring Harbor Laboratory, New York (1992) and in Ausubel et al., *Current Protocols in Molecular Biology*, (Supplement 54), John Wiley & Sons, New York (2001). The choice of a particular vector and host system for expression and screening of altered variable regions are known to those skilled in the art and will depend on the preference of the user. Moreover, expression of diverse populations of hetereomeric receptors in either soluble or cell surface form using filamentous bacteriophage vector/host systems is well known in the art and is the subject matter of U.S. Pat. No. 5,871,974.

The expressed population of altered variable region polypeptides can be screened for the identification of one or more altered variable region species exhibiting optimized binding activity, for example, binding affinity substantially the same or greater than the donor CDR variable region. Screening can be accomplished using various methods well known in the art for determining the binding affinity of a polypeptide or compound. Additionally, methods based on determining the relative affinity of binding molecules to their partner by comparing the amount of binding between the altered variable region polypeptides and the donor CDR variable region can similarly be used for the identification of species exhibiting binding affinity substantially the same or greater than the donor CDR variable region. All of such methods can be performed, for example, in solution or in solid phase. Moreover, various formats of binding assays are well known in the art and include, for example, immobilization to filters such as nylon or nitrocellulose; two-dimensional arrays, enzyme linked immunosorbant assay (ELISA), radioimmunoassay (RIA), panning and plasmon resonance. Such methods can be found described in, for example, Harlow and Lane, supra, 1988.

For the screening of populations of polypeptides such as the altered variable region populations produced by the methods of the invention, immobilization of the populations of altered variable regions to filters or other solid substrate can be advantageous because large numbers of different species can be efficiently screened for antigen binding. Such filter lifts allow for the identification of altered variable regions that exhibit substantially the same or greater binding affinity compared to the donor CDR variable region. Alternatively, if the populations of altered variable regions are expressed on the surface of a cell or bacteriophage, panning on immobilized antigen can be used to efficiently screen for variants having antigen binding activity or to determine the relative binding affinity of species within the population.

Another affinity method for screening populations of altered variable regions polypeptides is a capture lift assay that is useful for identifying a binding molecule having selective affinity for a ligand (Watkins et. al., (1997); WO 99/06834). This method employs the selective immobilization of altered variable regions to a solid support and then screening of the selectively immobilized altered variable regions for selective binding interactions against the cognate antigen or binding partner. Selective immobilization functions to increase the sensitivity of the binding interaction being measured since initial immobilization of a population of altered variable regions onto a solid support reduces non specific binding interactions with irrelevant molecules or contaminants which can be present in the reaction.

Another method for screening populations or for measuring the affinity of individual altered variable region polypeptides is through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates ($k_{on}$) and disassociation rates ($k_{off}$).

Measurements of $k_{on}$ and $k_{off}$ values can be used identify altered variable regions or optimized variable regions that are therapeutically more efficacious. For example, an altered variable region, or heteromeric binding fragment thereof, can be more efficacious because it has, for example, a higher $k_{on}$ valued compared to variable regions and heteromeric binding fragments that exhibit similar binding affinity. Increased efficacy is conferred because molecules with higher $k_{on}$ values can specifically bind and inhibit their target at a faster rate. Similarly, a molecule of the invention can be more efficacious because it exhibits a lower $k_{off}$ value compared to molecules having similar binding affinity. Increased efficacy observed with molecules having lower $k_{off}$ rates can be observed because, once bound, the molecules are slower to dissociate from their target. Although described with reference to the altered variable regions and optimized variable regions of the invention, the methods described above for measuring association and dissociation rates are applicable to essentially any antibody or fragment thereof for identifying more effective binders for therapeutic or diagnostic purposes.

Methods for measuring the affinity, including association and dissociation rates using surface plasmon resonance are well known in the art and can be found described in, for example, Jönsson and Malmquist, *Advances in Biosensors*, 2:291-336 (1992) and Wu et al. *Proc. Natl. Acad. Sci. USA*, 95:6037-6042 (1998). Moreover, one apparatus well known in the art for measuring binding interactions is a BIAcore 2000 instrument which is commercially available through Pharmacia Biosensor, (Uppsala, Sweden).

Using any of the above described screening methods, as well as others well known in the art, an altered variable region having optimized binding activity, for example, binding affinity substantially the same or greater than the donor CDR variable region is identified by detecting the binding of at least one altered variable region within the population to its antigen or cognate ligand. In addition to optimizing for antigen binding activity, catalytic activity can also be included in an invention antibody and optimized using the methods disclosed herein for binding affinity optimization. Accordingly, the above methods can be modified to include the addition of substrate and reactants to screen for optimized catalytic activity. Comparison, either independently or simultaneously in the same screen, with the donor variable region will identify those binders that have substantially the same or greater binding affinity as the donor. Those skilled in the art will know, or can determine using the donor variable region, binding conditions which are sufficient to identify selective interactions over non-specific binding.

Detection methods for identification of binding species within the population of altered variable regions can be direct or indirect and can include, for example, the measurement of light emission, radioisotopes, calorimetric dyes and fluorochromes. Direct detection includes methods that function without intermediates or secondary measuring procedures to assess the amount of bound antigen or ligand. Such methods generally employ ligands that are themselves labeled with a detectable moiety, for example, a radioactive, light emitting, fluorescent, colorimetric or enzyme moiety. In contrast, indirect detection includes methods that function through an intermediate or secondary measuring procedure. These methods generally employ molecules that specifically react with the antigen or ligand and can themselves be directly labeled with a detectable moiety or detected by a secondary reagent. For example, an antibody specific for a ligand can be detected using a secondary antibody capable of interacting with the first antibody specific for the ligand, again using the detection methods described above for direct detection. Moreover, for the specific example of screening for catalytic antibodies, the disappearance of a substrate or the appearance of a product can be used as an indirect measure of binding affinity or catalytic activity.

Isolated variable regions exhibit binding affinity as single chains, in the absence of assembly into a heteromeric structure with their respective $V_H$ or $V_L$ subunits. As such, populations of $V_H$ and $V_L$ altered variable regions polypeptides can be expressed alone and screened for binding activity, for example, optimized activity having substantially the same or greater binding affinity compared to the CDR donor $V_H$ or $V_L$ variable region. Alternatively, populations of $V_H$ and $V_L$ altered variable regions polypeptides can be coexpressed so that they self-assemble into heteromeric altered variable region binding fragments. The heteromeric binding fragment population can then be screened for species exhibiting binding affinity substantially the same or greater than the CDR donor variable region binding fragment.

Employing the methods for simultaneously grafting and optimizing, or for optimizing, it is possible to generate heteromeric variable region binding fragments having increases in affinities of greater than about 2-fold, 3-fold, 4-fold, 5-fold, 8-fold or 10-fold. In particular, heteromeric variable region binding fragments can be generated having increases in affinities of greater than 12-fold, 15-fold, 20-fold, and 25-fold as well as affinities greater than 50-fold, 100-fold, 200-fold, 500-fold or 1000-fold compared to the donor or parent molecule.

Additionally, the methods described herein for optimizing are also are applicable for producing catalytic heteromeric variable region fragments or for optimizing their catalytic activity. Catalytic activity can be optimized by changing, for example, the on or off rate of substrate binding, the substrate binding affinity, the transition state binding affinity, the turn-over rate (kcat) or the Km. Methods for measuring these characteristics are well known in the art (see, for example Segel, *Enzyme Kinetics*, John Wiley & Sons, New York (1975)). Such methods can be employed in the screening steps of the methods described above when used for optimizing the catalytic activity of a heteromeric variable region binding fragment.

Additionally, the methods for conferring donor CDR binding affinity onto an antibody acceptor variable region framework are applicable for grafting CDRs as described by Kabat et al., supra, Chothia et al., supra or MacCallum et al., supra. The methods similarly can be used for grafting into an acceptor framework overlapping regions or combinations of CDRs as described in Kabat et al., supra, Chothia et al., supra or MacCallum et al., supra. Generally, variable region CDRs are grafted by identifying the boundries described by one of the CDR definitions known in the art and set forth herein. However, because the methods are directed to constructing and screening populations of CDR grafted altered variable regions, which can incorporate relevant amino acid position changes in both the framework and CDR regions, and such variations can, for example, compensate or augment amino acid changes elsewhere in the variable region, the exact boundry of a particular CDR or set of variable region CDRs can be varied. Therefore, the exact CDR region to graft, whether it is the region described by Kabat et al., Chothia et al. or MacCallum et al., or any combination thereof, will essentially depend on the preference of the user.

Similarly, the methods described previously for optimizing the binding affinity of an antibody also are applicable for use with essentially any variable region for which an encoding nucleic acid is, or can be made, available. As with the methods for conferring donor CDR binding affinity, many applications of the methods for optimizing binding affinity will be for modifying the binding affinity of CDR grafted variable regions having human frameworks. Again, such molecules are significantly less antigenic in human patients and therefore therapeutically valuable in the treatment of human diseases. However, the methods of the invention for optimizing the binding affinity of a variable region are applicable to all species of variable regions. Therefore, the invention includes binding affinity optimization of variable regions derived from human, mouse, rat, rabbit, goat and chicken, or any other desired species.

The methods of the invention have been described with reference to variable regions and heteromeric variable region binding fragments. Those skilled in the art will understand that all of such methods are applicable to whole antibodies and functional fragments thereof as well as to regions and functional domains other than the antigen binding variable region of antibodies, if desired.

An association rate can be determined in any non-equilibrium mixture including, for example, one formed by rapidly contacting a binding polypeptide and ligand or by rapidly changing temperature. A non-equilibrium mixture can be a pre-equilibrium mixture. A pre-equilibrium mixture can be formed, for example, by contacting a soluble binding polypeptide and soluble ligand in a condition where the amount of total ligand and total binding polypeptide in the detection chamber are constant. Measurements of association rates in pre-equilibrium mixtures can be made in formats providing rapid mixing of binding polypeptide with ligand and rapid detection of changing properties of the binding polypeptide or ligand on a timescale of milliseconds or faster. Stopped flow and rapid quench flow instruments such as those described below provide a convenient means to measure non-equilibrium kinetics. The association rate can also be measured in non-equilibrium mixtures including, for example, solutions containing insoluble species of binding polypeptide, ligand or binding polypeptide bound to ligand, or solutions containing variable concentrations of total ligand or total binding polypeptide. Measurement of an association rate in a non-equilibrium mixture can be made in formats providing attachment of a ligand to a surface and continuous flow of a solution containing the binding polypeptide over the surface, or vice-versa, combined with rapid detection of changing properties of the binding polypeptide, ligand or surface such that measurements are made on a timescale of milliseconds or faster. Examples of formats providing non-equilibrium measurement of association rates include surface plasmon resonance instruments and evanescent wave instruments.

Association rate measurements can be made by detecting the change in a property of the binding polypeptide or ligand that exists between the bound and unbound state or by detecting a change in the surrounding environment when binding polypeptide and ligand associate. Properties of the binding polypeptide or ligand that can change upon association and that can be used to measure association rates include, for example, absorption and emission of heat, absorption and emission of electromagnetic radiation, affinity for a receptor, molecular weight, density, mass, electric charge, conductivity, magnetic moment of nuclei, spin state of electrons, polarity, molecular shape, or molecular size. Properties of the surrounding environment that can change when binding polypeptide associates with ligand include, for example, temperature and refractive index of surrounding solvent.

Formats for measuring association rates in pre-equilibrium mixtures include, for example, stopped flow kinetic instruments and rapid quench flow instruments. A stopped flow instrument can be used to push solutions containing a binding polypeptide and ligand from separate reservoirs into a mixing chamber just prior to passage into a detection cell. The instrument can then detect a change in one or more of the above described properties to monitor progress of the binding event. A rapid quench flow instrument can be used to rapidly mix a solution containing a binding polypeptide with a solution containing a ligand followed by quenching the binding reaction after a finite amount of time. A change in one or more of the above described properties can then be detected for quenched mixtures produced by quenching at different times following mixing. Quenching can be performed for example by freezing or addition of a chemical quenching agent so long as the quenching step does not inhibit detection of the property relied upon for measurement of binding rate. Thus, a rapid quench instrument can be useful, for example, in situations where spectroscopic detection is not convenient. A variety of instruments are commercially available from vendors such as KinTek Corp. (State College, Pa.) and Hi-Tech Scientific (Salisbury, UK).

Formats for measuring association rates in non-equilibrium mixtures include, for example, surface plasmon resonance and evanescent wave instruments. Surface plasmon resonance and evanescent wave technology utilize a ligand or binding polypeptide attached to a biosensor surface and a solution containing either the binding polypeptide or ligand respectively that is passed over the biosensor surface. The change in refractive index of the solution that occurs at the surface of a chip when binding polypeptide associates with ligand can be measured in a time dependent fashion. For example, surface plasmon resonance is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates ($k_{on}$) and disassociation rates ($k_{off}$). Surface plasmon resonance instruments are available in the art including, for example, the BIAcore instrument, IBIS system, SPR-CELLIA system, Spreeta, and Plasmon SPR and evanescent wave technology is available in the lasys system as described, for example, in Rich and Myszka, *Curr. Opin. Biotech.* 11:54-61 (2000).

Another method for measuring binding affinity includes comparative ELISA. As disclosed herein, an approximation of changes in affinity based on shifts in half-maximal binding was used to identify $k_{on}$ and $k_{off}$ values relative to wild type (Example III). Such a method is particularly useful for screening large numbers of variants, whereas the above-described methods can be used for detailed analysis of binding activity.

The association rate can be determined by measuring a change in a property of a ligand or binding polypeptide at one or more discreet time intervals during the binding event using, for example, the methods described above. Measurements determined at discreet time intervals during the binding event can be used to determine a quantitative measure of association rate or a relative measure of association rate. Quantitative measures of association rate can include, for example, an association rate value or $k_{on}$ value. Quantitative values of association rate or $k_{on}$ can be determined from a mathematical or graphical analysis of a time dependent measurement. Such analyses are well known in the art and include algorithms for fitting data to a sum of exponential or linear terms or algorithms for computer simulation to fit data to a binding model as described for example in Johnson, *Cur. Opin. Biotech.* 9:87-89 (1998), which is incorporated herein by reference.

Association rates can be determined from mixtures containing insoluble species or variable concentrations of total ligand or total binding polypeptide using mathematical and graphical analyses such as those described above if effects of mass transport are accounted for in the reaction. One skilled in the art can account for mass transport by comparing association rates under conditions having similar limitations with respect to mass transport or by adjusting the calculated association rate according to models available in the art including, for example those described in Myszka et al., *Biophys. J.* 75:583-594 (1998), which is incorporated herein by reference.

A higher value of either the association rate or $k_{on}$ is generally indicative of improved therapeutic potency. Thus, quantitative determinations provide an advantage by allowing comparison between an association rate of a binding polypeptide and a therapeutic control determined by different methods so long as the methods used are understood by one skilled in the art to yield consistent results.

A relative measure of association rate can include, for example, comparison of association rate for two or more binding polypeptides binding to ligand under similar conditions or comparison of association rate for a binding polypeptide binding to ligand with a predefined rate. Comparison of association rate for two or more binding polypeptides can include a standard of known association rate or a molecule of known therapeutic effect. A predefined rate used for comparison can be determined by calibrating the measurement relative to a previously measured rate including, for example, one available in the scientific literature or in a database. An example of a comparison with a predefined rate is selection of the species of binding polypeptide bound to ligand at a discreet time interval defined by the predefined rate by using a time actuated selection device.

For purposes of comparison, the association rate of a binding polypeptide and ligand can be determined relative to association rate for a therapeutic control and the same ligand. A comparison can also be made according to a quantitative association rate for binding polypeptide and ligand compared to a quantitative association rate for a therapeutic control and ligand. Relative or quantitative association rates can be determined by the methods described above. Determination of association rates for a binding polypeptide associating with a ligand can be performed simultaneously with a binding polypeptide and therapeutic control or at separate times, provided conditions are sufficiently similar in each assay to allow valid comparison. Thus, association rate determined for a binding polypeptide can be compared to a previously measured association rate for a therapeutic control.

A binding polypeptide having improved therapeutic potency can be distinguished from a binding polypeptide that has an increased $K_a$ for a ligand but not improved therapeutic potency. Methods for identifying a therapeutic binding polypeptide based on $K_a$ rely on an equilibrium measurement which, absent time dependent measurements made in non-equilibrium conditions, are inaccurate for identifying a binding polypeptide having increased association rate and therefore improved therapeutic potency. According to the relationship $K_a = k_{on}/k_{off}$, an increased $K_a$ for association of a binding polypeptide and ligand can be due to changes in $k_{on}$ or $k_{off}$. For example, a binding polypeptide having improved therapeutic potency can have a reduced $K_a$ if a reduction in $k_{off}$ occurs that over compensates for an increase in $k_{on}$. Thus, changes in $K_a$, being influenced by changes in $k_{off}$ do not unambiguously correlate with changes in therapeutic potency since binding polypeptides having improved therapeutic potency can display either reduced or increased $K_a$.

For optimization of binding activity of an antibody of the invention, the fold increase in association rate can be indicated by an increase in $k_{on}$. Therefore, $k_{on}$ can be about 2-fold, 3-fold, 4-fold, 5-fold, 6-fold, 7-fold, 8-fold, 9-fold, or 10 fold or more using methods described herein. The $k_{on}$ can be at least about $1 \times 10^2$ $M^{-1}s^{-1}$, $2 \times 10^2$ $M^{-1}s^{-1}$, $5 \times 10^2$ $M^{-1}s^{-1}$, $1 \times 10^3$ $M^{-1}s^{-1}$, $2 \times 10^3$ $M^{-1}s^{-1}$, $5 \times 10^3$ $M^{-1}s^{-1}$, $1 \times 10^4$ $M^{-1}s^{-1}$, $2 \times 10^4$ $M^{-1}s^{-1}$, $5 \times 10^4$ $M^{-1}s^{-1}$, $1 \times 10^5$ $M^{-1}s^{-1}$, $2 \times 10^5$ $M^{-1}s^{-1}$, or $3 \times 10^5$ $M^{-1}s^{-1}$. The $k_{on}$ can also be increased to at least about $5 \times 10^5$ $M^{-1}s^{-1}$, $7 \times 10^5$ $M^{-1}s^{-1}$, $9 \times 10^5$ $M^{-1}s^{-1}$, $1 \times 10^6$ $M^{-1}s^{-1}$, $3 \times 10^6$ $M^{-1}s^{-1}$, $5 \times 10^6$ $M^{-1}s^{-1}$, $7 \times 10^6$ $M^{-1}s^{-1}$, $9 \times 10^6$ $M^{-1}s^{-1}$ or $1 \times 10^7$ $M^{-1}s^{-1}$ or more. Furthermore, the increase in $k_{on}$ resulting in improved therapeutic potency can be independent of an effect of a change in $K_a$ for the binding polypeptide. The binding polypeptide having an increase in $k_{on}$ can have a $K_a$ value similar to $K_a$ for its parent polypeptide or a $K_a$ value lower than $K_a$ for its parent polypeptide.

The invention also provides nucleic acids encoding the antibodies and CDRs of the invention. The invention further provides nucleic acids encoding the mouse antibodies HUIV26 (SEQ ID NOS:1 and 3) and HUI77 (SEQ ID NOS:5 and 7) (see FIGS. 2 and 3). Further provided are nucleic acids encoding HUIV26 CDRs (SEQ ID NOS:20, 22, 24, 26, 28 and 30) and encoding HUI77 CDRs (SEQ ID NOS:32, 34, 36, 38, 40 and 42). Such nucleic acids include nucleic acids having degenerate codons encoding any or all of the amino acids in the CDRs. For example, the invention provides nucleic acids encoding HUIV26 CDRs: $V_L$ CDR1, SEQ ID NOS:19; $V_L$ CDR2, SEQ ID NO:21; $V_L$ CDR3, SEQ ID NO:23; $V_H$ CDR1, SEQ ID NO:25; $V_H$ CDR2, SEQ ID NO:27; and $V_H$ CDR3, SEQ ID NO:29. The invention also provides nucleic acids encoding HUI77 CDRs: $V_L$ CDR1, SEQ ID NOS:31; $V_L$ CDR2, SEQ ID NO:33; $V_L$ CDR3, SEQ ID NO:35; $V_H$ CDR1, SEQ ID NO:37; $V_H$ CDR2, SEQ ID NO:39; and $V_H$ CDR3, SEQ ID NO:41. Also included are degenerate versions of such nucleic acids such that they encode the amino acid sequences referenced as SEQ ID NOS: 20, 22, 24, 26, 28 and 30 for HUIV26 and SEQ ID NOS:32, 34, 36, 38, 40 and 42 for HUI77.

Further provided are nucleic acids encoding a HUIV26 or HUI77 CDR containing one or more amino acid subsitutions. For example, the invention provides nucleic acids encoding the CDRs of HUIV26 and HUI77 having single or multiple amino acid substitutions, as disclosed herein. If a nucleic acid encoding a CDR having one or more amino acid substitution is derived, for example, from one of SEQ ID NOS: 19, 21, 23, 25, 27 or 29 for HUIV26 or SEQ ID NOS:31, 33, 35, 37, 39 or 41 for HUI77, the amino acid substitutions can be encoded by any of the corresponding degenerate codons for that amino acid. Nucleic acids encoding such CDR variants can also include degenerate codons at any or all of the wild type amino acid positions.

Throughout the application, various nucleic acids and oligonucleotide primers, in addition to the naturally occurring nucleotides A, C, G, T or U, refer to standard abbreviations: R=G or A; Y=T/U or C; M=A or C; K=G or T/U; S=G or C; W=A or T/U; B=G, C or T/U; D=A, G or T/U; H=A, C or T/U; V=A, G or C; N=any nucleotide.

The antibodies of the invention have binding activity for a cryptic collagen epitope. The HUIV26 and HUI77 antibodies have been shown to target to angiogenic vasculature (see Xu et al., supra, 2001; WO 00/40597). Accordingly, the grafted HUIV26 and HUI77 antibodies of the invention, which specifically bind to a cryptic collagen epitope, similarly can target to angiogenic vasculature. One of the most significant and important aspects of the monoclonal antibodies HUIV26 and HUI77, and the grafted forms thereof disclosed herein, is that of their specificity. It is expected that systemic administration of antibodies of the invention will have minimal if any toxic side effects since the cryptic epitope(s) that is recognized by the HUIV26 and HUI77 antibodies is/are not exposed in mature native triple helical collagen but is only exposed upon denaturaion, for example, heat denaturation or proteolytic denaturation. Thus, little, if any, binding under normal physiological conditions is expected.

Moreover, the cryptic collagen domain(s) to which HUIV26 and HUI77 bind represents a novel therapeutic target for the treatment of numerous neovascular diseases including tumor growth and metastasis, diabetic retinopathy and other related ocular diseases such as macular degeneration, psoriasis, and rheumatoid arthritis. Other exemplary diseases associated with angiogenesis include, but are not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and the like cancers which require neovascularization to support tumor growth. Other exemplary tumors include melanoma, carcinoma, sarcoma, fibrosarcoma, glioma and astrocytoma, and the like.

Thus, the methods of the invention can be used to treat an individual having a disease associated with angiogenesis, including those described above. The methods can be used to ameliorate a sign or symptom associated with a disease. For example, in the case of cancer treatment, the methods can be used to inhibit tumor growth. One skilled in the art will know or can readily determine an appropriate sign or symptom associated with a disease suitable for determining the effectiveness of a therapeutic application using an antibody of the invention.

The antibodies of the invention can also be used as an important diagnostic and imaging reagent for the early detection of aberrant neovascularization associated with invasive tumor growth and metastasis. The antibodies of the invention can also be used in staging and grading of tumors since invasive tumor in contrast to benign lesions are likely to be associated with degradation of the surrounding basement membrane.

Thus, the invention provides a method of targeting angiogenic vasculature, comprising administering an antibody, or functional fragment thereof, the antibody or functional fragment thereof having specific binding activity for a cryptic collagen epitope, wherein the antibody or functional fragment is an antibody of the invention. For example, the antibodies can comprise one or more CDRs, including wild type CDRs or variants thereof, of the HUIV26 and HUI77 antibodies, as disclosed herein. The methods of targeting angiogenic vasculature can be used for therapeutic and/or diagnostic purposes.

For therapeutic purposes, the antibody, or functional fragment thereof, can be administered as a therapeutic agent itself or can further comprise a therapeutic moiety. In the case of a therapeutic moiety, the moiety can be a drug such as a chemotherapeutic agent, cytotoxic agent, toxin, or anti angiogenic agent, which refers to a molecule that reduces or inhibits angiogenesis. For example, a cytotoxic agent can be a radionuclide or chemical compound. Exemplary radionuclides useful as therapeutic agents include, for example, X-ray or γ-ray emitters. In addition, a moiety can be a drug delivery vehicle such as a chambered microdevice, a cell, a liposome or a virus, which can contain an agent such as a drug or a nucleic acid.

Exemplary therapeutic agents include, for example, the anthracyclin, doxorubicin, which has been linked to antibodies and the antibody/doxorubicin conjugates have been therapeutically effective in treating tumors (Sivam et al., *Cancer Res.* 55:2352-2356 (1995); Lau et al., *Bioorg. Med. Chem.* 3:1299-1304 (1995); Shih et al., *Cancer Immunol. Immunother.* 38:92-98 (1994)). Similarly, other anthracyclins, including idarubicin and daunorubicin, have been chemically conjugated to antibodies, which have delivered effective doses of the agents to tumors (Rowland et al., *Cancer Immunol. Immunother.* 37:195-202 (1993); Aboud-Pirak et al., *Biochem. Pharmacol.* 38:641-648 (1989)).

In addition to the anthracyclins, alkylating agents such as melphalan and chlorambucil have been linked to antibodies to produce therapeutically effective conjugates (Rowland et al., *Cancer Immunol. Immunother.* 37:195-202 (1993); Smyth et al., *Immunol. Cell Biol.* 65:315-321 (1987)), as have vinca alkaloids such as vindesine and vinblastine (Aboud-Pirak et al., supra, 1989; Starling et al., *Bioconj. Chem.* 3:315-322 (1992)). Similarly, conjugates of antibodies and antimetabolites such as 5-fluorouracil, 5 fluorouridine and derivatives thereof have been effective in treating tumors (Krauer et al., *Cancer Res.* 52:132-137 (1992); Henn et al., *J. Med. Chem.* 36:1570-1579 (1993)). Other chemotherapeutic agents, including cis-platinum (Schechter et al., *Int. J. Cancer* 48:167-172 (1991)), methotrexate (Shawler et al., *J. Biol. Resp. Mod.* 7:608 618 (1988); Fitzpatrick and Garnett, *Anticancer Drug Des.* 10:11-24 (1995)) and mitomycin-C (Dillman et al., *Mol. Biother.* 1:250-255 (1989)) also are therapeutically effective when administered as conjugates with various different antibodies. A therapeutic agent can also be a toxin such as ricin.

A therapeutic agent can also be a physical, chemical or biological material such as a liposome, microcapsule, micropump or other chambered microdevice, which can be used, for example, as a drug delivery system. Generally, such microdevices, should be nontoxic and, if desired, biodegradable. Various moieties, including microcapsules, which can contain an agent, and methods for linking a moiety, including a chambered microdevice, to an antibody of the invention are well known in the art and commercially available (see, for example, "Remington's Pharmaceutical Sciences" 18th ed. (Mack Publishing Co. 1990), chapters 89-91; Harlow and Lane, *Antibodies: A laboratory manual* (Cold Spring Harbor Laboratory Press 1988)).

For diagnostic purposes the antibody, or functional fragment thereof, can further comprise a detectable moiety. A detectable moiety can be, for example, a radionuclide, fluorescent, magnetic, colorimetric moeity, and the like. For in vivo diagnostic purposes, a moiety such as a gamma ray emitting radionuclide, for example, indium-111 or technitium 99, can be linked to an antibody of the invention and, following administration to a subject, can be detected using a solid scintillation detector. Similarly, a positron emitting radionuclide such as carbon-11 or a paramagnetic spin label such as carbon-13 can be linked to the molecule and, following administration to a subject, the localization of the moiety can be detected using positron emission transaxial tomography or magnetic resonance imaging, respectively. Such methods can identify a primary tumor as well as a metastatic lesion.

For diagnostic purposes, the antibodies of the invention can be used to determine the levels of denatured collagen in a tissue or in a bodily fluid. The level of denatured collagen can be determined in a tissue sample obtained from an individual, for example, by tissue biopsy. Exemplary bodily fluids include, but are not limited to, serum, plasma, urine, synovial fluid, and the like.

The invention also provides a method of inhibiting angiogenesis by administering an antibody, or functional fragment thereof, where the antibody or functional fragment thereof has specific binding activity for a cryptic collagen epitope, where the antibody comprises one or more CDRs of the invention. For example, an antibody of the invention can be administered so that angiogenesis is inhibited in a tissue of an individual. The invention further provides a method of targeting a tumor by administering an invention antibody. The invention also provides a method of inhibiting tumor growth by administering an antibody, or functional fragment thereof, of the invention.

The antibodies of the invention can also be used for in vivo or in vitro diagnostic applications. Thus, the invention provides a method of detecting angiogenic vasculature by contacting angiogenic vasculature with an antibody, or functional fragment thereof, of the invention. Angiogenic vasculature can be imaged in vivo by administering an antibody of the invention, either alone or attached to a detectable moiety, to an individual. The angiogenic vasculature can thus be detected in vivo. Alternatively, the antibody can be administered to a tissue obtained from an individual, for example, a tissue biopsy, such that an antibody of the invention can be used in vitro for diagnostic purposes to detect angiogenic vasculature.

A therapeutic or detectable moiety can be coupled to an antibody of the invention, or functional fragment thereof, by any of a number of well known methods for coupling or conjugating moieties. It is understood that such coupling methods allow the attachment of a therapeutic or detectable moiety without interfering or inhibiting the binding activity of the antibody, that is, the ability to bind a cryptic collagen site. Methods for conjugating moieties to an antibody of the invention, or functional fragment thereof, are well known to those skilled in the art (see, for example, Hermanson, *Bioconjugate Techniques*, Academic Press, San Diego (1996)).

When administered to a subject, the antibody of the invention is administered as a pharmaceutical composition containing, for example, the antibody and a pharmaceutically acceptable carrier. As disclosed herein, the antibody can be coupled to a therapeutic or detectable moiety. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art will know that the choice of a pharmaceutically acceptable carrier, including a physiologically acceptable compound, depends, for example, on the route of administration of the composition. The pharmaceutical composition also can contain an agent such as a cancer therapeutic agent.

One skilled in the art will know that a pharmaceutical composition containing an antibody of the invention can be administered to a subject by various routes including, for example, orally or parenterally, such as intravenously. The composition can be administered by injection or by intubation. The pharmaceutical composition also can be an antibody linked to liposomes or other polymer matrices, which can have incorporated therein, for example, a drug such as a chemotherapeutic agent (Gregoriadis, *Liposome Technology*, Vols. I to III, 2nd ed. (CRC Press, Boca Raton Fla. (1993), which is incorporated herein by reference). Liposomes, for example, which consist of phospholipids or other lipids, are nontoxic, physiologically acceptable and metabolizable carriers that are relatively simple to make and administer.

For diagnostic or therapeutic methods disclosed herein, an effective amount of the antibody and therapeutic moiety is administered to the subject. As used herein, the term "effective amount" means the amount of the pharmaceutical composition that produces the desired effect. An effective amount often will depend on whether the antibody itself is administered or whether the antibody is linked to a moiety and the type of moiety. Thus, a lesser amount of a radiolabeled molecule can be required for imaging as compared to the amount of a radioactive drug/antibody conjugate administered for therapeutic purposes. An effective amount of a particular antibody/moiety for a specific purpose can be determined using methods well known to those in the art. One skilled in the art can readily determine an appropriate dose of an antibody of the invention for an effective amount for therapeutic or diagnostic purposes.

For therapeutic or in vivo diagnostic purposes, it is understood that any of a variety of methods of administration can be used so long as the administration is effective for a desired purpose. Such methods of administration include, for example, intravenous, transdermal, intrasynovial, intramuscular, intratumoral, intraocular, intranasal, intrathecal, topical, oral, or the like. One skilled in the art can readily determine an appropriate mode of administration depending on the desired therapeutic effect or desired diagnostic purpose.

Furthermore, it is understood that for therapeutic or diagnostic applications, an antibody of the invention in general is administered to a mammal, for example, a human. Applications of an antibody of the invention for domestic animals or agricultural purposes include other mammals, for example, a non-human primate, pig, cow, horse, goat, sheep, mule, donkey, dog, cat, rabbit, mouse, rat, and the like.

It is understood that any of the therapeutic methods disclosed herein using an antibody of the invention can be used in combination with other therapeutic methods. For example, an antibody of the invention, either the antibody itself or an antibody attached to a therapeutic agent, can be administered simultaneously or sequentially with other therapeutic treatment regimens. For example, an antibody of the invention can be administered alone or in combination with another therapeutic treatment, including any of the therapeutic drugs disclosed herein as well as other drugs well known to those skilled in the art for treating a particular disease. For example, in the case of treating a cancer, an antibody of the invention can be administered simultaneously or sequentially with another chemotherapeutic agent such as a drug or radionuclide. Similarly, an antibody of the invention can be combined with other treatment regimens such as surgery by administering the antibody before, during or after surgery. One skilled in the art will know or can readily determine a desirable therapeutic treatment to be used in combination with an antibody of the invention, as desired. Thus, an antibody of the invention can be administered in conjunction with other therapeutic regimens, including but not limited to chemotherapy, radiation therapy, surgery, and the like.

The invention additionally provides a method of inhibiting metastasis using an antibody of the invention. The method can include the step of administering an antibody, or functional fragment thereof, having binding activity for a cryptic collagen epitope. The antibody can be, for example, an antibody comprising one or more CDRs having a least one amino acid substitution in one or more heavy or light chain CDRs of antibodies HUIV26 and HUI77. As used herein, inhibiting metastasis refers to decreasing the number and/or size of metastatic sites remote from a primary tumor site. The method of inhibiting metastasis can involve using an antibody of the invention that blocks adhesion of tumor cells to a cryptic collagen epitope that is exposed after remodeling of tissues by the action of collagen-degrading enzymes secreted by tumor cells.

As disclosed herein, a variant of HUI77 having one or more amino acid substitutions in one or more CDRs inhibited proliferation of melanoma cells in vitro (see Example VI). An antibody of the invention can block access to or inhibit binding of a survival or proliferative signal delivered to a tumor cell. Thus, the invention also provides a method of targeting a tumor cell by administration of an antibody of the invention having binding activity for a cryptic collagen epitope that blocks access to a survival or proliferative signal delivered to the tumor cell by a cryptic collagen site.

For methods of inhibiting angiogenesis, the angiogenic vasculature can be associated with a tumor. The methods of the invention can also be used to inhibit tumor growth directly, alone or in combination with inhibiting angiogenic vasculature of the tumor. The methods of the invention can additionally be used to inhibit metastasis, alone or in combination with inhibiting tumor angiogenic vasculature and/or tumor growth. Exemplary tumors include, but are not limited to, those disclosed herein, including melanoma, carcinoma, sarcoma, fibrosacroma, glioma, astrocytoma, and the like. Methods for testing the effect a HUIV26 or HUI77 variant for inhibition of angiogenesis or inhibition of tumor growth can be performed as described previously using, for example, assays such as the rat corneal micrdpocket angiogenesis assay, chick embryo tumor growth assay, or SCID mouse tumor growth assay, as described in Xu et al., supra, 2001, or any other well known assays for measuring inhibition of angiogenesis, inhibition of tumor growth, or inhibition of metastasis.

The methods of the invention can also be applied to inhibiting nontumor angiogenic vasculature. Such applications to non-tumor angiogenic vasculature can include tissue that is inflamed and in which angiogenesis is occurring. Exemplary non-tumor diseases associated with angiogenic vasculature suitable for treatment with an antibody of the invention include, but are not limited to, those disclosed herein, including arthritis, ocular disease, retinal disease, hemangioma, and the like. The antibodies of the invention can also be used to inhibit psoriasis, macular degeneration, restenosis, and the like, or any tumor or non-tumor disease associated with increased accessibility of a cryptic collagen epitope for which an antibody of the invention has binding activity.

It is understood that modifications which do not substantially affect the activity of the various embodiments of this invention are also provided within the definition of the invention provided herein. Accordingly, the following examples are intended to illustrate but not limit the present invention.

EXAMPLE I

Cloning of Heavy and Light Chain Variable Regions of HUIV26 and HUI77 Antibodies This example describes the cloning of HUIV26 and HUI77 antibody variable regions.

The variable regions of the HUIV26 and HUI77 antibodies were cloned from hybridomas expressing these mouse monoclonal antibodies and sequenced. Briefly, total mRNA was isolated from the respective mouse hybridoma cells using Oligotex® Direct mRNA Micro kit (Qiagen; Valencia Calif.). First strand cDNA was synthesized from the mRNA using SuperScript Preamplification System (GibcoBRL/Invitrogen; Carlsbad Calif.). Antibody variable region sequences were amplified by PCR using a set of 5' primers designed for signal sequences of mouse light chains or heavy chains to pair with single 3' primer to mouse kappa chain constant region for $V_L$ or IgM CH1 region for $V_H$ sequences. The sequences of the 5' primers for the signal peptide of mouse antibody heavy and light chain as well as constant region primers are shown in FIG. 1. The 3' primer for mouse kappa light chain constant region (primer 2650; SEQ ID NO:212) corresponds to amino acids 115-123. The 3' primer for mouse IgM CH1 region (primer 2656; SEQ ID NO:213) corresponds to amino acids 121-114. The 3' primer for mouse IgM CH1 region (primer 2706; SEQ ID NO:214) corresponds to amino acids 131-124.

The DNA fragments were isolated from PCR reactions, with a main product of about 400 bp in length. The DNA fragments were cloned into the pCR2.1 vector. The inserted DNA fragments were sequenced with both forward and reversed M13 primers. The DNA sequences were compared with an antibody sequence database. The N-terminal amino acid sequence of the HUIV26 and HUI77 antibodies were determined, and the sequences of the DNA fragments were also compared to the N-terminal amino acid sequences of the corresponding antibody.

The HUIV26 $V_L$ encoding nucleic acid was cloned with 5' primer mK2 (primer 2664; SEQ ID NO:185) and 3' primer 2650 (SES ID NO:212). A partial sequence of HUIV25 $V_L$ is ATCTTCTTGCTGTTCTGGGTATCTGGAACCTGTGG (SEQ ID NO:215), with the MK2 primer underlined and the partial sequence coding for mouse signal peptide in italics. The HUIV26 $V_H$ encoding nucleic acid was cloned with 5' primer MH12 (primer 2731; SEQ ID NO:203) and 3' primer 2706 (SEQ ID NO:214).

The HUI77 $V_L$ encoding nucleic acid was cloned with 5' primer mK1 (primer 2663; SEQ ID NO:184) and primer 2650 (SEQ ID NO:212). A partial sequence of HUI77 $V_L$ is TTGGTGCTGATGTTCTGGATTCCTGCTTCCAGCAGT (SEQ ID NO:216), with the mK1 primer underlined and the partial sequence coding for mouse signal peptide in italics. The HUI77 encoding nucleic acid was cloned with 5' primers MH15 (primer 2734; SEQ ID NO:206) or MH16 (primer 2735; SEQ ID NO:207) and 3∝primer 2656 (SEQ ID NO:213).

The sequences of the heavy and light chain nucleotide and amino acid sequences for HUIV26 and HUI77 are shown in FIGS. 2 and 3, respectively. Using the numbering system of Kabat, supra, the CDRs of the heavy and light chains were identified for each of the HUIV26 and HUI77 antibodies (underlined in FIGS. 2C and 3C).

An alignment of the HUI77 $V_L$ nucleotide sequence (SEQ ID NO:9) with the nucleotide sequence of the human framework fusion DPK13/JK1 (SEQ ID NO:17) is shown in FIG. 3D. The corresponding light chain amino acid sequences are referenced as SEQ ID NO:10 and SEQ ID NO:18 for HUI77 and DPK13/JK1, respectively.

This example describes the cloning and the sequence of mouse antibodies HUIV26 and HUI77.

EXAMPLE II

Generation of CDR Variant Libraries of HUIV26 and HUI77 Antibodies

This example describes the generation of CDR variant libraries of HUIV26 and HUI77 antibodies for CDR optimization.

The CDR3 regions of antibodies HUIV26 and HUI77 were optimized by generating a library of CDR variants. Primers for light chain CDR3 and heavy chain CDR3 were used to generate a library of CDR3 variants, where the primer was synthesized to encode more than one amino acid one or more positions in CDR3. Following synthesis of primers encoding CDR3 variants, the variant CDR3 regions were assembled into light chain ($V_L$) and heavy chain ($V_H$) regions.

Briefly, humanized $V_L$ and $V_H$ genes of HUI77 and HUIV26 antibodies were assembled with the primers shown in FIGS. 4A and 5A, respectively, using PCR or primer-elongation-ligation. Variable region genes containing CDR3 mutations were assembled by replacing the wild type CDR3 primer (IV26-17, IV26-h7, 177-17 or 177-h7) with the group of mutant primers corresponding to that CDR. The assembled variable regions were then amplified and asymmetrically biotinylated on plus strand by PCR using primers B-pelB and 224 for $V_L$ and B-phA and 1200a for HV genes. The primers for amplification of humanized $V_L$ and $V_H$ sequences and the isolation of minus strand DNA were: B-pelB, Biotin-TTA CTC GCT GCC CAA CCA GCC ATG GCC (SEQ ID NO:220); 224, GAC AGA TGG TGC AGC CAC AGT (SEQ ID NO:221); B-phoA, Biotin-TTA CTG TTT ACC CCT GTG ACA AAA GCC (SEQ ID NO:222); and 1200a, GAA GAC CGA TGG GCC CTT GGT (SEQ ID NO:223).

The assembled $V_L$ and $V_H$ regions were introduced into a Fab expression vector by mutagenesis. Briefly, the non-biotinylated minus strands were isolated after binding the PCR products to NeutrAvidin-conjugated magnetic beads and introduced into the Fab expression vector IX-104CSA by hybridization mutagenesis (Kristensson et al., *Vaccines 95*, pp. 39-43, Cold Spring Harbor Laboratory, Cold Spring Harbor (1995); Kunkel, *Proc. Natl. Acad. Sci. USA* 82:488-492 (1985); Wu et al., *J. Mol. Bio.* 294:151-162 (1999)).

Three humanization-CDR3-mutation libraries were constructed for each the HUI77 and HUIV26 antibodies. The three libraries introduced random mutations but differed in CDR3 mutations. One library had mutations only in LCDR3, the second library had mutations only in HCDR3, and the third library had mutations in both LCDR3 and HCDR3.

Methods essentially the same as those described above for CDR3 mutagenesis were also performed on CDR1 and CDR2 of the HUIV26 and HUI77 antibodies. After assembling into a Fab expression vector, the Fabs containing HUIV26 and HUI77 variant CDRs were expressed in bacteria and tested for binding to denatured collagen. The mutant libraries were screened with filter lift screening and ELISA. The assays were performed essentially as described previously (Huse et al., *J. Immunol.* 149:3914-3920 (1992); Watkins et al., *Anal. Biochem.* 253:37-45 (1997)). Briefly, nitrocellulose membranes were pre-coated with heat-denatured human collagen I or IV and used to lift *E. coli*-expressed variant FABs from phage plates. The membranes were then incubated with antibodies, either anti-human kappa chain or anti-hemaglutinin (HA) tag conjugated to alkaline phosphatase to detect bound variant Fabs. Positive clones were screened again by single point ELISA (Watkins et al., supra, 1997) for binding to denatured-biotinylated human collagen I and IV, correspondingly. Beneficial variants were characterized for binding to both collagens in native and heat-denatured forms by ELISA. Beneficial mutations were determined as those having higher affinity binding to denatured collagen relative to the corresponding wild type Fab, as demonstrated by ELISA.

Shown in FIGS. 4B and 5B is a summary of beneficial CDR mutations in the HUIV26 and HUI77 antibodies, respectively. FIG. 4B summarizes beneficial single amino acid mutations in heavy chain CDR1, CDR2, and CDR3 and light chain CDR1 and CDR3 of HUIV26. An exemplary HUIV26 variant having a single amino acid substitution is the 12F10Q variant, which exhibited $k_{on}$ of 0.055 and $k_{off}$ of 0.049 as estimated by the fold improvement based on shifts in half-maximal binding obtained from ELISA titrations.

FIG. 5B summarizes beneficial single amino acid mutations in heavy chain CDR1, CDR2 and CDR3 and light chain CDR1, CDR2 and CDR3 of HUI77. As can be seen, numerous single amino acid mutations in various CDRs were found to maintain or enhance binding to a cryptic collagen site.

This example describes CDR variants of HUIV26 and HUI77 having beneficial mutations.

EXAMPLE III

Identification of Combinatorial Variants of HUIV26 and HUI77 Antibodies Having Enhanced Activity This example describes the generation and identification of combinatorial variants incorporating various beneficial CDR mutations in HUIV26 and HUI77.

To further optimize HUIV26 and HUI77 antibody CDR variants, combinatorial variants, which incorporate at least two CDRs containing one or more mutations, were generated and tested for binding to a cryptic collagen site. Combinatorial variants were synthesized using primers with one or more positions encoding variant amino acids as described in Example II. The primers used are shown in FIGS. 6 and 7.

Shown in FIGS. 6 and 7 is a summary of the beneficial combinatorial variants of HUIV26 and HUI77 antibodies, respectively. The $k_{on}$ and $k_{off}$ values shown in FIGS. 6 and 7 ("SPEKon" and "SPEKoff") were estimated as the fold improvement of variants based on shifts in half-maximal binding obtained from ELISA titrations. Also shown are several variants having the same beneficial CDR mutations but having different framework sequences. These results show that beneficial CDR mutations can be grafted into a variety of frameworks and can retain or have improved binding activity.

This example shows the generation of combinatorial CDR variants of HUIV26 and HUI77. A number of variants were identified having increased affinity relative to wild type forms of the respective antibodies.

EXAMPLE IV

Binding Activity and Specificity of HUIV26 and HUI77 Variants

This example describes the binding activity and specificity of HUIV26 and HUI77 antibodies on native and denatured collagen.

The activity and specificity of wild type and selected exemplary HUIV26 and HUI77 variants were determined. As shown in FIG. 8, the activity and specificity of IX-IV26, a Fab containing wild type HUIV26 CDRs, and the HUIV26 variants 2D4H1-C3 and DhuG5 were determined. The antibodies were tested for binding to denatured collagen IV (FIG. 8A), denatured collagen I (FIG. 8B), and native collagen IV (FIG. 8C). None of the antibodies had significant binding activity for native collagen IV (FIG. 8C). All three antbodies exhibited binding activity for denatured collagen IV (FIG. 8A). However, the 2D4H1-C3 and DhuG5 variants exhibited significantly increased binding activity relative to IX-IV26 (FIG. 8A). IX-IV26 did not exhibit significant binding activity to denatured collagen I, and 2D4H1-C3 and DhuG5 exhibited low binding activity at the highest measured concentration of antibody (FIG. 8B). These results indicate that the HUIV26 variants have similar binding activity and specificity as that of wild type HUIV26 and maintain activity and specificity for a cryptic collagen epitope. These results further show that variants having mutated CDRs can have maintained or increased binding affinity relative to wild type.

Figure 9:
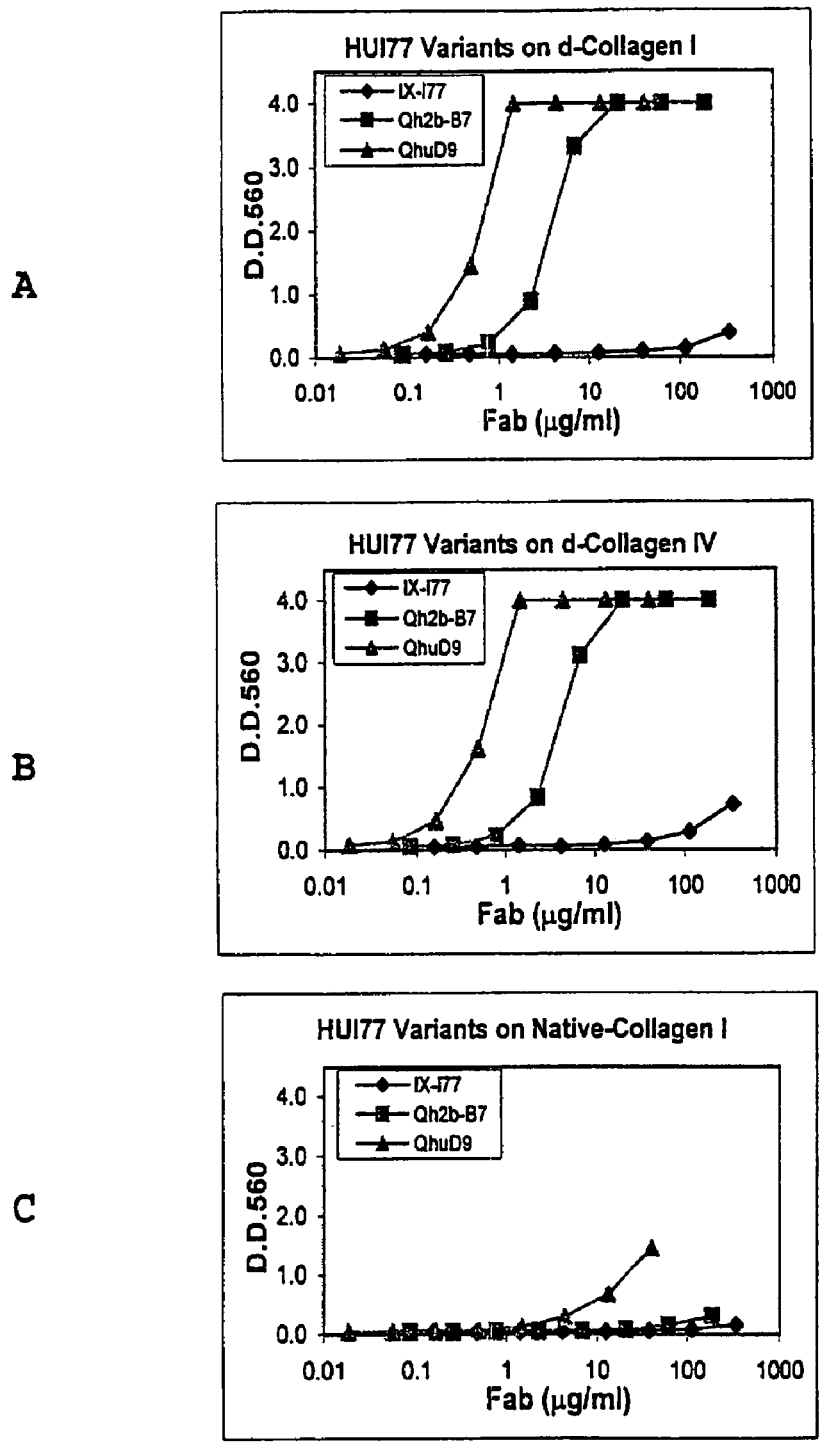
FIG. 9 shows the activity and specificity of HUI77 variants. The binding of purified Fabs of IX-I77, containing wild type HUI77 CDRs, and HUI77 variants Qh2b-B7 and QhuD9 is shown for denatured collagen I (FIG. 9A), denatured collagen IV (FIG. 9B) and native collagen I (FIG. 9C).

As shown in FIG. 9, the activity and specificity of IX-177, a Fab containing wild type HUI77 CDRs, and the HUI77 variants Qh2b-B7 and QhuD9 were determined. The antibodies were tested for binding to denatured collagen I (FIG. 9A), denatured collagen IV (FIG. 9B) and native collagen I (FIG. 9C), and the results indicate that these variants exhibited similar binding specificities as wild type. Neither IX-I77 nor Qhu2b-B7 exhibited significant binding activity for native collagen I, although the variant QhuD9 exhibited modest binding activity to native collagen at higher concentrations of antibody. The antibodies all exhibited binding activity for denatured collagen I (FIG. 9A) and denatured collagen IV (FIG. 9B). However, the Qhu2b-B7 and QhuD9 variants exhibited significantly increased binding activity relative to IX-I77 on both denatured collagen I and IV. These results indicate that variants having mutated CDRs can have maintained or increased binding affinity relative to wild type.

Figure 10:
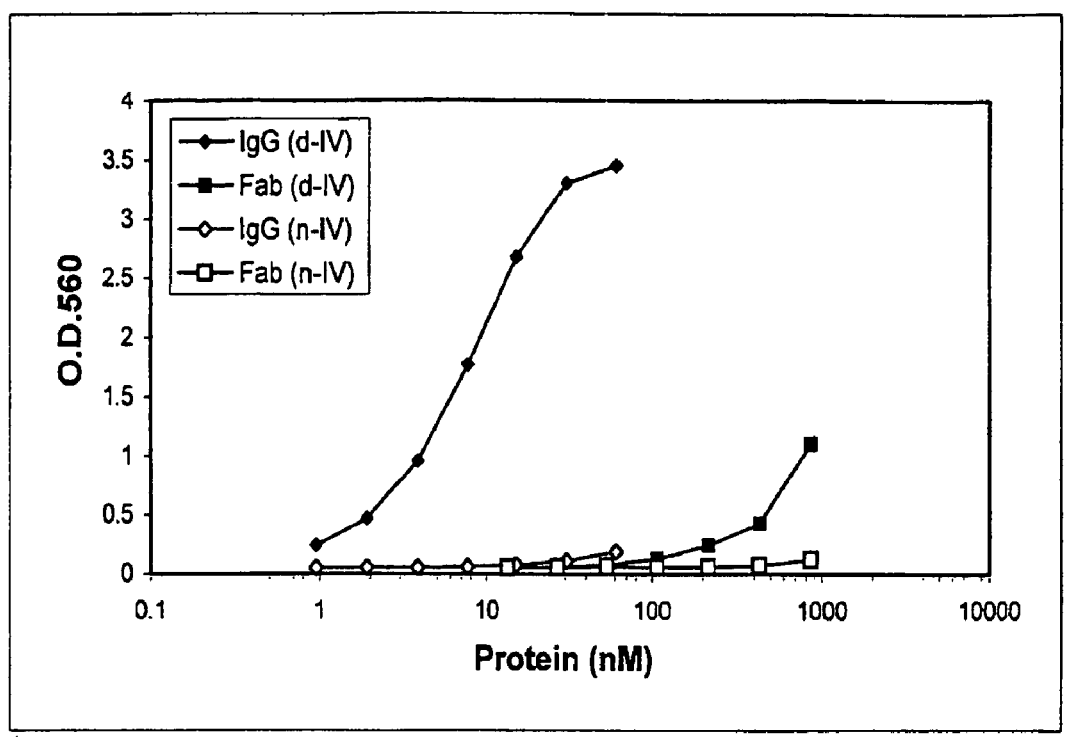
FIG. 10 shows the binding activity of the HUIV26 variant DhuH8. The binding activity of the Fab form and the IgG form of the antibody to denatured (d-IV) and native (n-IV) human collagen IV is shown.

To further examine the effect of CDR mutations on binding activity, the HUIV26 variant DhuH8 was selected and expressed in two forms, as a Fab and immunoglobulin (IgG). The binding activity of these two forms was determined for native (n-IV) and denatured (d IV) human collagen IV. As shown in FIG. 10, neither the Fab nor IgG form of the Dhu8 variant exhibited significant binding to native collagen IV. The Fab form exhibited binding activity for denatured collagen IV, and the binding affinity was significantly increased for the IgG form. These results indicate that a HUIV26 variant having one or more CDR amino acid substitutions relative to wild type can exhibit binding to a cryptic collagen epitope and that the binding affinity can be significantly increased in the IgG form relative to the Fab form of the antibody variant.

These results indicate that HUIV26 and HUI77 variants having one or more CDR amino acid substitutions can exhibit similar binding specificity and increased binding affinity relative to wild type.

EXAMPLE V

Generation of Grafted HUIV26 and HUI77 Antibodies Having Optimized CDRs

This example describes the generation of humanized HUIV26 and HUI77 antibodies incorporating beneficial CDR mutations.

A CDR variant have a beneficial mutation is identified as described in Examples II and III. Once a beneficial CDR variant is identified, the CDR variant is grafted into a human framework sequence. In addition to the CDR variant having a beneficial mutation, other. CDRs can be a wild type sequence of the respective antibody or one or more variant CDRs. At least one of the CDRs will be a variant containing a beneficial mutation. For example, if the grafted antibody contains a heavy and light chain, at least one of the heavy or light chain CDRs will have at least one amino acid mutation relative to the corresponding wild type CDR.

A human framework sequence is selected as the recipient for grafting. The human framework can be closely related to the donor antibody framework sequence or can be relatively divergent from the parental donor antibody. Once a human framework is selected for grafting, overlapping oligonucleotides are synthesized encoding the selected human framework and the appropriate donor CDRs, including at least one variant CDR containing at least one beneficial mutation. The overlapping oligonucleotides are used to assemble a nucleic acid encoding a variable region including the selected human framework, the CDR variant, and appropriate other CDRs to generate an antibody or fragment having binding activity for a cryptic collagen site.

The assembled variable region is cloned into an expression vector, for example, a Fab expression vector such as described in Example II, and binding activity to denatured collagen is tested, as described in Examples II and III.

This example describes the generation of humanized antibodies containing beneficial CDR mutations of HUIV26 and HUI77 antibodies.

EXAMPLE VI

Inhibition of B16 Melanoma Cell Proliferation by a Variant HUI77 Antibody

This example describes the effect of the HUI77 variant QH2b on B16 melanoma cell proliferation.

The humanized Fab designated QH2b, which is the QH2b-B7 variant of the HUI77 antibody, was engineered into a full length IgG1 antibody (QH2b-IgG1). The QH2b-IgG1 antibody was expressed in mammalian cell culture in NSO cells and purified.

Figure 11:
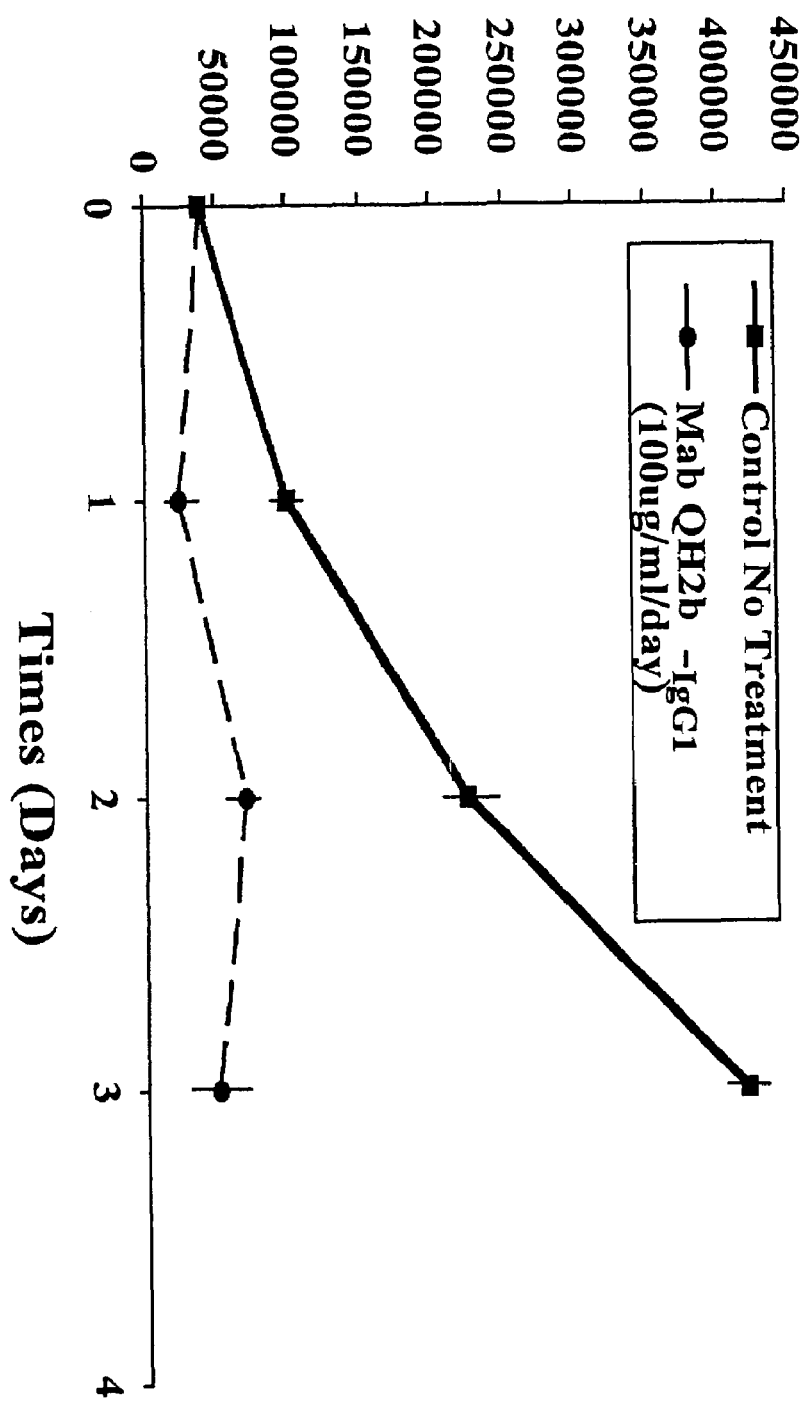
FIG. 11 shows the effect of the HUI77 variant QH2b on B16 melanoma cell proliferation. B16 melanoma cells grown in culture were not treated (control; squares) or treated with the IgG form of the QH2b variant (circles).

The purified QH2b-IgG1 antibody was used in a cell proliferation assay in vitro. B16 melanoma cells were plated on denatured human Type I collagen. QH2b IgG1(100 µg/ml/day) was added to one set of culture dishes and cell numbers were determined at the indicated times (FIG. 11). As a control, the cells were not treated with antibody.

As shown in FIG. 11, B16 melanoma cells proliferated on denatured collagen type-I, as indicated by the increase in cell numbers over 3 days. The B16 melanoma cell cultures treated with QH2b-IgG1 exhibited essentially no cell growth over a period of 3 days, indicating that the melanoma cells did not proliferate in the presence of the HUI77 variant QH2b-IgG1.

These results indicate that a HUI77 variant having one or more CDR amino acid substitutions can inhibit cell proliferation of B16 melanoma cells.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated antibody or antigen-binding fragment thereof, which has higher binding affinity for denatured collagen type I or type IV over native collagen type I or type IV, wherein said antibody or antigen-binding fragment thereof, comprises:
  a heavy chain CDR1 referenced as SEQ ID NO:147;
  a heavy chain CDR2 referenced as SEQ ID NO:144;
  a heavy chain CDR3 referenced as SEQ ID NO:103;
  a light chain CDR1 referenced as SEQ ID NO:149;
  a light chain CDR2 referenced as SEQ ID NO:34; and
  a light chain CDR3 referenced as SEQ ID NO:36.

2. The antigen-binding fragment of claim 1, wherein said antigen-binding fragment is selected from among a Fv, a Fd, a Fab, a F(ab')$_2$ and a scFv.

3. The antibody, or antigen-binding fragment thereof, of claim 1, further comprising a therapeutic moiety.

4. The antibody, or antigen-binding fragment thereof, of claim 1, further comprising a detectable moiety.

5. The antibody, or antigen-binding fragment thereof, of claim 1, wherein said antibody or antigen-binding fragment thereof has a specific binding activity for a cryptic collagen epitope.

6. The antibody, or antigen-binding fragment thereof, of claim 1, wherein said antibody or antigen-binding fragment thereof has at least a two-fold higher binding activity for denatured collagen over native collagen.

7. A grafted antibody, or antigen-binding fragment thereof, comprising the antibody, or antigen-binding fragment thereof, of claim 1, wherein the heavy chain CDRs are grafted into a VHIII/JH6 heavy chain variable region framework referenced as SEQ ID NO: 8.

8. The antigen-binding fragment of claim 7, wherein said antigen-binding fragment is selected from among a Fv, a Fd, a Fab, a F(ab')$_2$ and a scFv.

9. The grafted antibody, or antigen-binding fragment thereof, of claim 7, further comprising a therapeutic moiety.

10. The grafted antibody, or antigen-binding fragment thereof, of claim 7, further comprising a detectable moiety.

11. The grafted antibody, or antigen-binding fragment thereof, of claim 7, wherein said grafted antibody or antigen-binding fragment thereof that has higher binding affinity for denatured collagen type I or type IV over native collagen type I or type IV.

* * * * *

SEQUENCE LISTING

```
<160> NUMBER OF SEQ ID NOS: 358

<210> SEQ ID NO 1
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 1 gac att gtg atg aca cag tct cca tct ttg ttg agt gtg tca gca gga        48
Asp Ile Val Met Thr Gln Ser Pro Ser Leu Leu Ser Val Ser Ala Gly
1               5                   10                  15 gag aag gtc act atg agc tgc aag tcc agt cag agt ctg tta aac agt        96
Glu Lys Val Thr Met Ser Cys Lys Ser Ser Gln Ser Leu Leu Asn Ser
            20                  25                  30 gga aat caa aag aac tac ttg gcc tgg tac cag cag aaa cca ggg cag       144
Gly Asn Gln Lys Asn Tyr Leu Ala Trp Tyr Gln Gln Lys Pro Gly Gln
        35                  40                  45 cct cct aaa ctg ttg atc tat ggg gca tcc act agg gaa tct ggg gtc       192
Pro Pro Lys Leu Leu Ile Tyr Gly Ala Ser Thr Arg Glu Ser Gly Val
    50                  55                  60 cct gat cgc ttc aca ggc agt gga tct gga acc gat ttc act ctt atc       240
Pro Asp Arg Phe Thr Gly Ser Gly Ser Gly Thr Asp Phe Thr Leu Ile
65                  70                  75                  80 atc agc agt gtg cag gct gaa gac ctg gca gtt tat tac tgt cag aat       288
Ile Ser Ser Val Gln Ala Glu Asp Leu Ala Val Tyr Tyr Cys Gln Asn
                85                  90                  95 gat cat agt tat ccg tac acg ttc gga ggg ggg acc aag ctg gaa ata       336
Asp His Ser Tyr Pro Tyr Thr Phe Gly Gly Gly Thr Lys Leu Glu Ile
            100                 105                 110 aaa                                                                    339
Lys

<210> SEQ ID NO 2
<211> LENGTH: 113
<212> TYPE: PRT
<213> ORGANISM: Mus musculus

<400> SEQUENCE: 2

Asp Ile Val Met Thr Gln Ser Pro Ser Leu Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45
```

```
Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Ile
65                  70                  75                  80

Ile Ser Ser Val Gln Ala Glu Asp Leu Ala Val Tyr Tyr Cys Gln Asn
                85                  90                  95

Asp His Ser Tyr Pro Tyr Thr Phe Gly Gly Gly Thr Lys Leu Glu Ile
            100                 105                 110

Lys

<210> SEQ ID NO 3
<211> LENGTH: 360
<212> TYPE: DNA
<213> ORGANISM: Mus musculus
<220> FEATURE:
<221> NAME/KEY: CDS
<222> LOCATION: (1)..(360)

<400> SEQUENCE: 3 gag gtg aag ctt ctc gag tct gga ggt ggc ctg gtg cag cct gga gga       48
Glu Val Lys Leu Leu Glu Ser Gly Gly Gly Leu Val Gln Pro Gly Gly
1               5                   10                  15 tcc ctg aaa ctc tcc tgt gca gcc tca gga ttc gat ttt agt aga tac       96
Ser Leu Lys Leu Ser Cys Ala Ala Ser Gly Phe Asp Phe Ser Arg Tyr
            20                  25                  30 tgg atg agt tgg gtc cgg cag gct cca ggg aaa ggg cta gaa tgg att      144
Trp Met Ser Trp Val Arg Gln Ala Pro Gly Lys Gly Leu Glu Trp Ile
        35                  40                  45 gga gaa att aat cca gat agc agt acg ata aac tat acg cca tct cta      192
Gly Glu Ile Asn Pro Asp Ser Ser Thr Ile Asn Tyr Thr Pro Ser Leu
    50                  55                  60 aag gat aaa ttc atc atc tcc aga gac aac gcc aaa aat acg ctg tac      240
Lys Asp Lys Phe Ile Ile Ser Arg Asp Asn Ala Lys Asn Thr Leu Tyr
65                  70                  75                  80 ctg caa atg agc aaa gtg aga tct gag gac aca gcc ctt tat tac tgt      288
Leu Gln Met Ser Lys Val Arg Ser Glu Asp Thr Ala Leu Tyr Tyr Cys
                85                  90                  95 gca aga ccg gtt gat ggt tac tac gat gct atg gac tac tgg ggt caa      336
Ala Arg Pro Val Asp Gly Tyr Tyr Asp Ala Met Asp Tyr Trp Gly Gln
            100                 105                 110 gga acc tca gtc acc gtc tcc tca                                      360
Gly Thr Ser Val Thr Val Ser Ser
        115                 120

<210> SEQ ID NO 4
<211> LENGTH: 120
<212> TYPE: PRT
<213> ORGANISM: Mus musculus

<400> SEQUENCE: 4

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80
```

Leu Gln Met Ser Lys Val Arg Ser Glu Asp Thr Ala Leu Tyr Tyr Cys
                85                  90                  95

Ala Arg Pro Val Asp Gly Tyr Tyr Asp Ala Met Asp Tyr Trp Gly Gln
            100                 105                 110

Gly Thr Ser Val Thr Val Ser Ser
        115                 120

<210> SEQ ID NO 5
<211> LENGTH: 305
<212> TYPE: DNA
<213> ORGANISM: Homo sapiens

<400> SEQUENCE: 5
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctcc                                                               305

<210> SEQ ID NO 6
<211> LENGTH: 113
<212> TYPE: PRT
<213> ORGANISM: Homo sapiens

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp His Ser Tyr Pro Tyr Thr Phe Gly Gln Gly Thr Lys Leu Glu Ile
            100                 105                 110

Lys

<210> SEQ ID NO 7
<211> LENGTH: 294
<212> TYPE: DNA
<213> ORGANISM: Homo sapiens

<400> SEQUENCE: 7
gaggtgcagc tggtggagtc tgggggaggc ttggtccagc ctggggggtc cctgagactc    60
tcctgtgcag cctctggatt cacctttagt agctattgga tgagctgggt ccgccaggct   120
ccagggaagg ggctggagtg ggtggccaac ataaagcaag atggaagtga gaaatactat   180
gtggactctg tgaagggccg attcaccatc tccagagaca cgccaagaa ctcactgtat   240 ctgcaaatga acagcctgag agccgaggac acggctgtgt attactgtgc gaga         294

<210> SEQ ID NO 8
<211> LENGTH: 120
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Tyr Tyr Tyr Tyr Gly Met Asp Val Trp Gly Gln
            100                 105                 110

Gly Thr Thr Val Thr Val Ser Ser
        115                 120

<210> SEQ ID NO 9
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 9 gat gtt ttg atg acc caa act cca ctc tcc ctg cct gtc agt ctt gga       48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt       96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct      144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggt gtc cca      192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt      288
Ser Arg Val Glu Ala Glu Asp Leu Gly Val Tyr Tyr Cys Phe Gln Gly
                85                  90                  95 tca cat gtt ccg tgg acg ttc ggt gga ggc acc aag ctg gaa atc aaa      336
Ser His Val Pro Trp Thr Phe Gly Gly Gly Thr Lys Leu Glu Ile Lys
            100                 105                 110

<210> SEQ ID NO 10
<211> LENGTH: 112
<212> TYPE: PRT
<213> ORGANISM: Mus musculus

```
<400> SEQUENCE: 10

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 11
<211> LENGTH: 369
<212> TYPE: DNA
<213> ORGANISM: Mus musculus
<220> FEATURE:
<221> NAME/KEY: CDS
<222> LOCATION: (1)..(369)

<400> SEQUENCE: 11 cag gtt act ctg aaa gag act ggc cct ggg ata ttg cag ccc tcc cag      48
Gln Val Thr Leu Lys Glu Thr Gly Pro Gly Ile Leu Gln Pro Ser Gln
1               5                   10                  15 acc ctc agt ctg act tgt tct ttc tct ggg ttt tca ctg agc act tct      96
Thr Leu Ser Leu Thr Cys Ser Phe Ser Gly Phe Ser Leu Ser Thr Ser
            20                  25                  30 ggt atg ggt gta ggc tgg att cgt cag cct tca gga gag ggt cta gag     144
Gly Met Gly Val Gly Trp Ile Arg Gln Pro Ser Gly Glu Gly Leu Glu
        35                  40                  45 tgg ctg gca gac att tgg tgg gat gac aat aag tac tat aac cca tcc     192
Trp Leu Ala Asp Ile Trp Trp Asp Asp Asn Lys Tyr Tyr Asn Pro Ser
    50                  55                  60 ctg aag agc cgg ctc aca atc tcc aag gat acc tcc agc aac cag gta     240
Leu Lys Ser Arg Leu Thr Ile Ser Lys Asp Thr Ser Ser Asn Gln Val
65                  70                  75                  80 ttc ctc aag atc acc agt gtg gac act gca gat act gcc act tac tac     288
Phe Leu Lys Ile Thr Ser Val Asp Thr Ala Asp Thr Ala Thr Tyr Tyr
                85                  90                  95 tgt gct cga aga gct aac tat ggt aac ccc tac tat gct atg gac tac     336
Cys Ala Arg Arg Ala Asn Tyr Gly Asn Pro Tyr Tyr Ala Met Asp Tyr
            100                 105                 110 tgg ggt caa gga acc tca gtc acc gtc tcc tca                          369
Trp Gly Gln Gly Thr Ser Val Thr Val Ser Ser
        115                 120

<210> SEQ ID NO 12
<211> LENGTH: 123
<212> TYPE: PRT
<213> ORGANISM: Mus musculus

<400> SEQUENCE: 12

Gln Val Thr Leu Lys Glu Thr Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30
```

-continued

Gly Met Gly Val Gly Trp Ile Arg Gln Pro Ser Gly Glu Gly Leu Glu
            35                  40                  45

Trp Leu Ala Asp Ile Trp Trp Asp Asp Asn Lys Tyr Tyr Asn Pro Ser
 50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Asn Tyr Gly Asn Pro Tyr Tyr Ala Met Asp Tyr
            100                 105                 110

Trp Gly Gln Gly Thr Ser Val Thr Val Ser Ser
            115                 120

<210> SEQ ID NO 13
<211> LENGTH: 305
<212> TYPE: DNA
<213> ORGANISM: Homo sapiens

<400> SEQUENCE: 13
gatattgtga tgacccagac tccactctcc ctgcccgtca cccctggaga gccggcctcc      60
atctcctgca ggtctagtca gagcctcttg atagtgatg atggaaacac ctatttggac      120
tggtacctgc agaagccagg gcagtctcca cagctcctga tctatacgct ttcctatcgg     180
gcctctggag tcccagacag gttcagtggc agtgggtcag gcactgattt cacactgaaa     240
atcagcaggg tggaggctga ggatgttgga gtttattact gcatgcaacg tatagagttt     300
ccttc                                                                 305

<210> SEQ ID NO 14
<211> LENGTH: 111
<212> TYPE: PRT
<213> ORGANISM: Homo sapiens

<400> SEQUENCE: 14

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Gly Asn Thr Tyr Leu Asp Trp Tyr Leu Gln Lys Pro Gly Gln Ser
            35                  40                  45

Pro Gln Leu Leu Ile Tyr Thr Leu Ser Tyr Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

His Val Pro Trp Thr Phe Gly Gln Gly Thr Lys Val Glu Ile Lys
            100                 105                 110

<210> SEQ ID NO 15
<211> LENGTH: 288
<212> TYPE: DNA
<213> ORGANISM: Homo sapiens

<400> SEQUENCE: 15
caggtcacct tgaaggagtc tggtcctgcg ctggtgaaac ccacacagac cctcacactg      60
acctgcacct tctctgggtt ctcactcagc actagtggaa tgcgtgtgag ctggatccgt     120

```
cagcccccag ggaaggccct ggagtggctt gcacgcattg attgggatga tgataaattc    180
tacagcacat ctctgaagac caggctcacc atctccaagg acacctccaa aaaccaggtg    240
gtccttacaa tgaccaacat ggaccctgtg acacagcca cgtattac                  288
```

```
<210> SEQ ID NO 16
<211> LENGTH: 123
<212> TYPE: PRT
<213> ORGANISM: Homo sapiens

<400> SEQUENCE: 16
```

| Gln | Val | Thr | Leu | Lys | Glu | Ser | Gly | Pro | Ala | Leu | Val | Lys | Pro | Thr | Gln |
|---|---|---|---|---|---|---|---|---|---|---|---|---|---|---|---|
| 1 |  |  |  | 5 |  |  |  |  | 10 |  |  |  |  | 15 |  |

| Thr | Leu | Thr | Leu | Thr | Cys | Thr | Phe | Ser | Gly | Phe | Ser | Leu | Ser | Thr | Ser |
|---|---|---|---|---|---|---|---|---|---|---|---|---|---|---|---|
|  |  |  | 20 |  |  |  |  | 25 |  |  |  |  | 30 |  |  |

| Gly | Met | Arg | Val | Ser | Trp | Ile | Arg | Gln | Pro | Pro | Gly | Lys | Ala | Leu | Glu |
|---|---|---|---|---|---|---|---|---|---|---|---|---|---|---|---|
|  |  | 35 |  |  |  |  | 40 |  |  |  |  | 45 |  |  |  |

| Trp | Leu | Ala | Arg | Ile | Asp | Trp | Asp | Asp | Lys | Phe | Tyr | Ser | Thr | Ser |
|---|---|---|---|---|---|---|---|---|---|---|---|---|---|---|
| 50 |  |  |  |  | 55 |  |  |  |  | 60 |  |  |  |  |

| Leu | Lys | Thr | Arg | Leu | Thr | Ile | Ser | Lys | Asp | Thr | Ser | Lys | Asn | Gln | Val |
|---|---|---|---|---|---|---|---|---|---|---|---|---|---|---|---|
| 65 |  |  |  |  | 70 |  |  |  |  | 75 |  |  |  |  | 80 |

| Val | Leu | Thr | Met | Thr | Asn | Met | Asp | Pro | Val | Asp | Thr | Ala | Thr | Tyr | Tyr |
|---|---|---|---|---|---|---|---|---|---|---|---|---|---|---|---|
|  |  |  |  | 85 |  |  |  |  | 90 |  |  |  |  | 95 |  |

| Cys | Ala | Arg | Arg | Ala | Asn | Tyr | Tyr | Tyr | Tyr | Tyr | Ala | Met | Asp | Val |
|---|---|---|---|---|---|---|---|---|---|---|---|---|---|---|
|  |  |  | 100 |  |  |  |  | 105 |  |  |  |  | 110 |  |

| Trp | Gly | Gln | Gly | Thr | Thr | Val | Thr | Val | Ser | Ser |
|---|---|---|---|---|---|---|---|---|---|---|
|  |  | 115 |  |  |  |  | 120 |  |  |  |

```
<210> SEQ ID NO 17
<211> LENGTH: 340
<212> TYPE: DNA
<213> ORGANISM: Homo sapiens
<220> FEATURE:
<221> NAME/KEY: CDS
<222> LOCATION: (1)..(339)

<400> SEQUENCE: 17
```

```
gat att gtg atg acc cag act cca ctc tcc ctg ccc gtc acc cct gga      48
Asp Ile Val Met Thr Gln Thr Pro Leu Ser Leu Pro Val Thr Pro Gly
1               5                   10                  15 gag ccg gcc tcc atc tcc tgc agg tct agt cag agc ctc ttg gat agt      96
Glu Pro Ala Ser Ile Ser Cys Arg Ser Ser Gln Ser Leu Leu Asp Ser
            20                  25                  30 gat gat gga aac acc tat ttg gac tgg tac ctg cag aag cca ggg cag     144
Asp Asp Gly Asn Thr Tyr Leu Asp Trp Tyr Leu Gln Lys Pro Gly Gln
        35                  40                  45 tct cca cag ctc ctg atc tat acg ctt tcc tat cgg gcc tct gga gtc     192
Ser Pro Gln Leu Leu Ile Tyr Thr Leu Ser Tyr Arg Ala Ser Gly Val
    50                  55                  60 cca gac agg ttc agt ggc agt ggg tca ggc act gat ttc aca ctg aaa     240
Pro Asp Arg Phe Ser Gly Ser Gly Ser Gly Thr Asp Phe Thr Leu Lys
65                  70                  75                  80 atc agc agg gtg gag gct gag gat gtt gga gtt tat tac tgc atg caa     288
Ile Ser Arg Val Glu Ala Glu Asp Val Gly Val Tyr Tyr Cys Met Gln
                85                  90                  95 cgg ttc aca tgt tcc gtg gac gtt cgg cca agg gac caa ggt gga aat     336
Arg Phe Thr Cys Ser Val Asp Val Arg Pro Arg Asp Gln Gly Gly Asn
            100                 105                 110 caa a                                                                340
Gln
```

<210> SEQ ID NO 18
<211> LENGTH: 113
<212> TYPE: PRT
<213> ORGANISM: Homo sapiens

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Phe Thr Cys Ser Val Asp Val Arg Pro Arg Asp Gln Gly Gly Asn
            100                 105                 110

Gln

<210> SEQ ID NO 19
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 19 aag tcc agt cag agt ctg tta aac agt gga aat caa aag aac tac ttg      48
Lys Ser Ser Gln Ser Leu Leu Asn Ser Gly Asn Gln Lys Asn Tyr Leu
1               5                   10                  15 gcc                                                                   51
Ala

<210> SEQ ID NO 20
<211> LENGTH: 17
<212> TYPE: PRT
<213> ORGANISM: Mus musculus

<400> SEQUENCE: 20

Lys Ser Ser Gln Ser Leu Leu Asn Ser Gly Asn Gln Lys Asn Tyr Leu
1               5                   10                  15

Ala

<210> SEQ ID NO 21
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 21 ggg gca tcc act agg gaa tct                                           21
Gly Ala Ser Thr Arg Glu Ser
1               5

<210> SEQ ID NO 22
<211> LENGTH: 7
<212> TYPE: PRT
<213> ORGANISM: Mus musculus

<400> SEQUENCE: 22

Gly Ala Ser Thr Arg Glu Ser
1               5

<210> SEQ ID NO 23
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 23 cag aat gat cat agt tat ccg tac acg                                    27
Gln Asn Asp His Ser Tyr Pro Tyr Thr
1               5

<210> SEQ ID NO 24
<211> LENGTH: 9
<212> TYPE: PRT
<213> ORGANISM: Mus musculus

<400> SEQUENCE: 24

Gln Asn Asp His Ser Tyr Pro Tyr Thr
1               5

<210> SEQ ID NO 25
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 25 gga ttc gat ttt agt aga tac tgg atg agt                                30
Gly Phe Asp Phe Ser Arg Tyr Trp Met Ser
1               5                   10

<210> SEQ ID NO 26
<211> LENGTH: 10
<212> TYPE: PRT
<213> ORGANISM: Mus musculus

<400> SEQUENCE: 26

Gly Phe Asp Phe Ser Arg Tyr Trp Met Ser
1               5                   10

<210> SEQ ID NO 27
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 27 gaa att aat cca gat agc agt acg ata aac tat acg cca tct cta aag        48
Glu Ile Asn Pro Asp Ser Ser Thr Ile Asn Tyr Thr Pro Ser Leu Lys
1               5                   10                  15 gat                                                                    51
Asp

<210> SEQ ID NO 28
<211> LENGTH: 17
<212> TYPE: PRT
<213> ORGANISM: Mus musculus

<400> SEQUENCE: 28

```
Glu Ile Asn Pro Asp Ser Ser Thr Ile Asn Tyr Thr Pro Ser Leu Lys
1               5                   10                  15

Asp
```

<210> SEQ ID NO 29
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 29

```
ccg gtt gat ggt tac tac gat gct atg gac tac                          33
Pro Val Asp Gly Tyr Tyr Asp Ala Met Asp Tyr
1               5                   10
```

<210> SEQ ID NO 30
<211> LENGTH: 11
<212> TYPE: PRT
<213> ORGANISM: Mus musculus

<400> SEQUENCE: 30

```
Pro Val Asp Gly Tyr Tyr Asp Ala Met Asp Tyr
1               5                   10
```

<210> SEQ ID NO 31
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 31

```
aga tct agt cag agc att gta cat agt aat gga aac acc tat tta gaa     48
Arg Ser Ser Gln Ser Ile Val His Ser Asn Gly Asn Thr Tyr Leu Glu
1               5                   10                  15
```

<210> SEQ ID NO 32
<211> LENGTH: 16
<212> TYPE: PRT
<213> ORGANISM: Mus musculus

<400> SEQUENCE: 32

```
Arg Ser Ser Gln Ser Ile Val His Ser Asn Gly Asn Thr Tyr Leu Glu
1               5                   10                  15
```

<210> SEQ ID NO 33
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 33

```
aaa gtt tcc aac cga ttt tct                                          21
Lys Val Ser Asn Arg Phe Ser
1               5
```

<210> SEQ ID NO 34
<211> LENGTH: 7
<212> TYPE: PRT
<213> ORGANISM: Mus musculus

<400> SEQUENCE: 34

Lys Val Ser Asn Arg Phe Ser
1               5

<210> SEQ ID NO 35
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 35 ttt caa ggt tca cat gtt ccg tgg acg                                      27
Phe Gln Gly Ser His Val Pro Trp Thr
1               5

<210> SEQ ID NO 36
<211> LENGTH: 9
<212> TYPE: PRT
<213> ORGANISM: Mus musculus

<400> SEQUENCE: 36

Phe Gln Gly Ser His Val Pro Trp Thr
1               5

<210> SEQ ID NO 37
<211> LENGTH: 36
<212> TYPE: DNA
<213> ORGANISM: Mus musculus
<220> FEATURE:
<221> NAME/KEY: CDS
<222> LOCATION: (1)..(36)

<400> SEQUENCE: 37 ggg ttt tca ctg agc act tct ggt atg ggt gta ggc                          36
Gly Phe Ser Leu Ser Thr Ser Gly Met Gly Val Gly
1               5                   10

<210> SEQ ID NO 38
<211> LENGTH: 12
<212> TYPE: PRT
<213> ORGANISM: Mus musculus

<400> SEQUENCE: 38

Gly Phe Ser Leu Ser Thr Ser Gly Met Gly Val Gly
1               5                   10

<210> SEQ ID NO 39
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 39 gac att tgg tgg gat gac aat aag tac tat aac cca tcc ctg aag agc          48
Asp Ile Trp Trp Asp Asp Asn Lys Tyr Tyr Asn Pro Ser Leu Lys Ser
1               5                   10                  15

```
<210> SEQ ID NO 40
<211> LENGTH: 16
<212> TYPE: PRT
<213> ORGANISM: Mus musculus

<400> SEQUENCE: 40

Asp Ile Trp Trp Asp Asp Asn Lys Tyr Tyr Asn Pro Ser Leu Lys Ser
1               5                   10                  15

<210> SEQ ID NO 41
<211> LENGTH: 39
<212> TYPE: DNA
<213> ORGANISM: Mus musculus
<220> FEATURE:
<221> NAME/KEY: CDS
<222> LOCATION: (1)..(39)

<400> SEQUENCE: 41 aga gct aac tat ggt aac ccc tac tat gct atg gac tac                  39
Arg Ala Asn Tyr Gly Asn Pro Tyr Tyr Ala Met Asp Tyr
1               5                   10

<210> SEQ ID NO 42
<211> LENGTH: 13
<212> TYPE: PRT
<213> ORGANISM: Mus musculus

<400> SEQUENCE: 42

Arg Ala Asn Tyr Gly Asn Pro Tyr Tyr Ala Met Asp Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 43

Gly Phe Asp Phe Ser His Tyr Trp Met Ser
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 44

Gly Phe Asp Phe Ser Arg Tyr Trp Ile Ser
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 45

Gly Phe Asp Phe Ser Arg Tyr Trp Met Thr
1               5                   10
```

```
<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 46

Gly Phe Asp Phe Ser Arg Tyr Trp Met Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 47

Gly Phe Asp Phe Ser Arg Tyr Trp Met Gly
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 48

Glu Ile Asn Pro Asp Ser Ser Thr Ala Asn Tyr Thr Pro Ser Leu Lys
1               5                   10                  15

Asp

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 49

Glu Ile Asn Pro Asp Ser Ser Thr Ser Asn Tyr Thr Pro Ser Leu Asp
1               5                   10                  15

Lys

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 50

Glu Ile Asn Pro Asp Ser Ser Thr Ile Asn Tyr Thr Pro Tyr Leu Lys
1               5                   10                  15

Asp
```

```
<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 51

Glu Ile Asn Pro Asp Ser Ser Thr Ile Asn Tyr Thr Pro Ala Leu Lys
1               5                   10                  15
Asp

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 52

Glu Ile Asn Pro Asp Ser Ser Thr Ile Asn Tyr Thr Pro His Leu Lys
1               5                   10                  15
Asp

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 53

Glu Ile Asn Pro Asp Ser Ser Thr Ile Asn Tyr Thr Pro Gly Leu Lys
1               5                   10                  15
Asp

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 54

Glu Ile Asn Pro Asp Ser Ser Thr Ile Asn Tyr Thr Pro Ser Leu Gln
1               5                   10                  15
Asp

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 55

Glu Ile Asn Pro Asp Ser Ser Thr Ile Asn Tyr Thr Pro Ser Leu Lys
1               5                   10                  15
Ser
```

```
<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 56

Pro Val Pro Gly Tyr Tyr Asp Ala Met Asp Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 57

Pro Val Gly Gly Tyr Tyr Asp Ala Met Asp Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 58

Pro Val Thr Gly Tyr Tyr Asp Ala Met Asp Tyr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 59

Pro Val Ala Gly Tyr Tyr Asp Ala Met Asp Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 60

Pro Val Asp Pro Tyr Tyr Asp Ala Met Asp Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation
```

```
<400> SEQUENCE: 61

Pro Val Asp Ala Tyr Tyr Asp Ala Met Asp Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 62

Pro Val Asp His Tyr Tyr Asp Ala Met Asp Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 63

Pro Val Asp Gly Tyr Tyr Asp Ala Met Asp Pro
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 64

Pro Val Asp Gly Tyr Tyr Asp Ala Met Asp Asn
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 65

Lys Ser Ser Arg Ser Leu Leu Asn Ser Gly Asn Gln Lys Asn Tyr Leu
1               5                   10                  15

Ala

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 66

Lys Ser Ser Ser Ser Leu Leu Asn Ser Gly Asn Gln Lys Asn Tyr Leu
1               5                   10                  15

Ala
```

```
<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 67

Lys Ser Ser Gln Ser Leu Leu Ser Ser Gly Asn Gln Lys Asn Tyr Leu
1               5                   10                  15

Ala

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 68

Lys Ser Ser Gln Ser Leu Leu Asn Tyr Gly Asn Gln Lys Asn Tyr Leu
1               5                   10                  15

Ala

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 69

Lys Ser Ser Gln Ser Leu Leu Asn Trp Gly Asn Gln Lys Asn Tyr Leu
1               5                   10                  15

Ala

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 70

Lys Ser Ser Gln Ser Leu Leu Asn His Gly Asn Gln Lys Asn Tyr Leu
1               5                   10                  15

Ala

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 71

Lys Ser Ser Gln Ser Leu Leu Asn Arg Gly Asn Gln Lys Asn Tyr Leu
1               5                   10                  15

Ala
```

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 72

Lys Ser Ser Gln Ser Leu Leu Asn Ser Tyr Asn Gln Lys Asn Tyr Leu
1               5                   10                  15

Ala

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 73

Lys Ser Ser Gln Ser Leu Leu Asn Ser Arg Asn Gln Lys Asn Tyr Leu
1               5                   10                  15

Ala

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 74

Lys Ser Ser Gln Ser Leu Leu Asn Ser His Asn Gln Lys Asn Tyr Leu
1               5                   10                  15

Ala

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 75

Lys Ser Ser Gln Ser Leu Leu Asn Ser Ile Asn Gln Lys Asn Tyr Leu
1               5                   10                  15

Ala

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 76

Lys Ser Ser Gln Ser Leu Leu Asn Ser Gly Asn Lys Lys Asn Tyr Leu
1               5                   10                  15

Ala

```
<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 77

Gln Asn Asp His Gln Tyr Pro Tyr Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 78

Gln Asn Asp His Gly Tyr Pro Tyr Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 79

Gln Asn Asp His Leu Tyr Pro Tyr Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 80

Gln Asn Asp His Ala Tyr Pro Tyr Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 81

Gln Asn Asp His Thr Tyr Pro Tyr Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation
```

```
<400> SEQUENCE: 82

Gln Asn Asp His Val Tyr Pro Tyr Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 83

Gln Asn Asp His Ser Asn Pro Tyr Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 84

Gln Asn Asp His Ser Ser Pro Tyr Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 85

Gln Asn Asp His Ser Pro Pro Tyr Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 86

Gln Asn Asp His Ser Met Pro Tyr Thr
1               5

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 87

Gly Phe Ser Leu Ser Thr Pro Gly Met Gly Val Gly
1               5                   10
```

```
<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 88

Gly Phe Ser Leu Ser Thr Trp Gly Met Gly Val Gly
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 89

Gly Phe Ser Leu Ser Thr Ser Gly Met Gly Val Trp
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 90

Gly Phe Ser Leu Ser Thr Ser Gly Met Gly Val Leu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 91

Gly Phe Ser Leu Ser Thr Ser Gly Met Gly Val Ala
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 92

Asp Ile Trp Trp Asp Asp Asn Lys Tyr Ser Asn Pro Ser Leu Lys Ser
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation
```

-continued

```
<400> SEQUENCE: 93

Asp Ile Trp Trp Asp Asp Asn Lys Tyr Ala Asn Pro Ser Leu Lys Ser
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 94

Asp Ile Trp Trp Asp Asp Asn Lys Tyr Pro Asn Pro Ser Leu Lys Ser
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 95

Asp Ile Trp Trp Asp Asp Asn Lys Tyr Tyr Asn Pro Ser Leu Pro Ser
1               5                   10                  15

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 96

Pro Ala Asn Tyr Gly Asn Pro Tyr Tyr Ala Met Asp Tyr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 97

Gln Ala Asn Tyr Gly Asn Pro Tyr Tyr Ala Met Asp Tyr
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 98

Leu Ala Asn Tyr Gly Asn Pro Tyr Tyr Ala Met Asp Tyr
1               5                   10
```

```
<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 99

Thr Ala Asn Tyr Gly Asn Pro Tyr Tyr Ala Met Asp Tyr
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 100

Val Ala Asn Tyr Gly Asn Pro Tyr Tyr Ala Met Asp Tyr
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 101

Arg Ala Asn Tyr Gly Val Pro Tyr Tyr Ala Met Asp Tyr
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 102

Arg Ala Asn Tyr Gly Trp Pro Tyr Tyr Ala Met Asp Tyr
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 103

Arg Ala Asn Tyr Gly Asn Pro Tyr Tyr Ala Gln Asp Tyr
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation
```

<400> SEQUENCE: 104

Arg Ala Asn Tyr Gly Asn Pro Tyr Tyr Ala Asn Asp Tyr
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 105

Arg Ala Asn Tyr Gly Asn Pro Tyr Tyr Ala Thr Asp Tyr
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 106

Arg Ala Asn Tyr Gly Asn Pro Tyr Tyr Ala Met Asp Lys
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 107

Arg Ala Asn Tyr Gly Asn Pro Tyr Tyr Ala Met Asp Thr
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 108

Arg Ala Asn Tyr Gly Asn Pro Tyr Tyr Ala Met Asp Met
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 109

Arg Ala Asn Tyr Gly Asn Pro Tyr Tyr Ala Met Asp His
1               5                   10

```
<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 110

Arg Ser Ser Gln Ser Ile Pro His Ser Asn Gly Asn Thr Tyr Leu Glu
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 111

Arg Ser Ser Gln Ser Ile Trp His Ser Asn Gly Asn Thr Tyr Leu Glu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 112

Arg Ser Ser Gln Ser Ile Val Leu Ser Asn Gly Asn Thr Tyr Leu Glu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 113

Arg Ser Ser Gln Ser Ile Val Ser Ser Asn Gly Asn Thr Tyr Leu Glu
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 114

Arg Ser Ser Gln Ser Ile Val His Trp Asn Gly Asn Thr Tyr Leu Glu
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation
```

-continued

```
<400> SEQUENCE: 115

Arg Ser Ser Gln Ser Ile Val His Ser Tyr Gly Asn Thr Tyr Leu Glu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 116

Arg Ser Ser Gln Ser Ile Val His Ser Trp Gly Asn Thr Tyr Leu Glu
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 117

Arg Ser Ser Gln Ser Ile Val His Ser Asn Gly Tyr Thr Tyr Leu Glu
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 118

Arg Ser Ser Gln Ser Ile Val His Ser Asn Gly Asn Thr Tyr Phe Glu
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 119

Arg Ser Ser Gln Ser Ile Val His Ser Asn Gly Asn Thr Tyr Val Glu
1               5                   10                  15

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 120

Ser Val Ser Asn Arg Phe Ser
1               5
```

```
<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 121

Lys Ala Ser Asn Arg Phe Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 122

Lys Val Ser Ser Arg Phe Ser
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 123

Lys Val Ser Asn Leu Phe Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 124

Lys Val Ser Asn Arg Phe Trp
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 125

Lys Val Ser Asn Arg Phe Phe
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation
```

```
<400> SEQUENCE: 126

Val Gln Gly Ser His Val Pro Trp Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 127

His Gln Gly Ser His Val Pro Trp Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 128

Phe Arg Gly Ser His Val Pro Trp Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 129

Phe Trp Gly Ser His Val Pro Trp Thr
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 130

Phe Gln Ser Ser His Val Pro Trp Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 131

Phe Gln Gly Trp His Val Pro Trp Thr
1               5
```

```
<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 132

Phe Gln Gly Glu His Val Pro Trp Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 133

Phe Gln Gly Ser Leu Val Pro Trp Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 134

Phe Gln Gly Ser Thr Val Pro Trp Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 135

Phe Gln Gly Ser Ser Val Pro Trp Thr
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 136

Phe Gln Gly Ser Ala Val Pro Trp Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation
```

```
<400> SEQUENCE: 137

Phe Gln Gly Ser Gln Val Pro Trp Thr
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 138

Phe Gln Gly Ser His Thr Pro Trp Thr
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 139

Phe Gln Gly Ser His Val Pro Trp Ala
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 140

Phe Gln Gly Ser His Val Pro Trp Arg
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 141

Phe Gln Gly Ser His Val Pro Trp His
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 142

Phe Gln Gly Ser His Val Pro Trp Lys
1               5
```

```
<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 143

Phe Gln Gly Ser His Val Pro Trp Ile
1               5

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 144

Asp Ile Trp Trp Asp Asp Asn Lys Tyr Thr Asn Pro Ser Leu Lys Ser
1               5                   10                  15

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 145

Phe Gln Gly Ser His Phe Pro Trp Thr
1               5

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 146

Arg Ser Ser Gln Ser Ile Val His Ser Gln Gly Asn Thr Tyr Leu Glu
1               5                   10                  15

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 147

Gly Phe Ser Leu Ser Thr Pro Gly Met Gly Val Trp
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      antibody mutation
```

```
<400> SEQUENCE: 148

Gly Phe Ser Leu Ser Thr Pro Gly Met Gly Val Ala
1               5                   10

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 149

Arg Ser Ser Gln Ser Ile Val Ser Ser Trp Gly Asn Thr Tyr Leu
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 150

Arg Ser Ser Gln Ser Ile Val Ser Ser Tyr Gly Asn Thr Tyr Leu
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 151

Arg Ser Ser Gln Ser Ile Val Ser Ser Gln Gly Asn Thr Tyr Leu
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 152

Arg Ser Ser Gln Ser Ile Val His Ser Gln Gly Asn Thr Tyr Phe
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 153

Arg Ser Ser Gln Ser Ile Val Ser Ser Trp Gly Asn Thr Tyr Phe
1               5                   10                  15
```

```
<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 154

Glu Ile Asn Pro Asp Ser Ser Thr Ala Asn Tyr Thr Pro Ala Leu Lys
1               5                   10                  15

Asp

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 155

Glu Ile Asn Pro Asp Ser Ser Thr Ala Asn Tyr Thr Pro Tyr Leu Lys
1               5                   10                  15

Asp

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 156

Glu Ile Asn Pro Asp Ser Ser Thr Ala Asn Tyr Thr Pro His Leu Lys
1               5                   10                  15

Asp

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 157

Lys Ser Ser Gln Ser Leu Leu Asn Trp Tyr Asn Gln Lys Asn Tyr Leu
1               5                   10                  15

Ala

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 158

Lys Ser Ser Gln Ser Leu Leu Asn Tyr Tyr Asn Gln Lys Asn Tyr Leu
1               5                   10                  15

Ala
```

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 159

Lys Ser Ser Gln Ser Leu Leu Asn Tyr His Asn Gln Lys Asn Tyr Leu
1               5                   10                  15

Ala

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 160

Lys Ser Ser Gln Ser Leu Leu Asn Arg Tyr Asn Gln Lys Asn Tyr Leu
1               5                   10                  15

Ala

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 161

Lys Ser Ser Gln Ser Leu Leu Asn Trp His Asn Gln Lys Asn Tyr Leu
1               5                   10                  15

Ala

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 162

Glu Ile Asn Pro Asp Ser Ser Thr Val Asn Tyr Thr Pro Ser Leu Lys
1               5                   10                  15

Asp

<210> SEQ ID NO 163
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tctctggaga tggtgaattt acgtactgct atctggatt                              39

<210> SEQ ID NO 164
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ctaagtagtt cttttggttg ttataacaga ctctggctgg a                41

<210> SEQ ID NO 165
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tggagcctgg cggacccagg hcatccaata tctactaaag gtgaatccag a        51

<210> SEQ ID NO 166
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tctctggaga tggtgaatyt atcctttagg gmtggcgtat agttggccgt actgctatct    60
ggatt                                                                65

<210> SEQ ID NO 167
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
tctctggaga tggtgaatyt atcctttagg trtggcgtat agttggccgt actgctatct    60
ggatt                                                                65

<210> SEQ ID NO 168
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ctaagtagtt cttttggttg trgtrgytta acagactctg gctgga              46

<210> SEQ ID NO 169
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 169
ctaagtagtt cttttggttg csgtrgytta acagactctg gctgga              46

<210> SEQ ID NO 170
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ctaagtagtt cttttggttg trgckgytta acagactctg gctgga              46

<210> SEQ ID NO 171
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ctaagtagtt cttttggttg csgckgytta acagactctg gctgga              46

<210> SEQ ID NO 172
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ctaagtagtt cttttggttg trccagytta acagactctg gctgga              46

<210> SEQ ID NO 173
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ctaagtagtt cttttggttg csccagytta acagactctg gctgga              46

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cttctgcagg taccattcgt tatacaatgc tctgactaga                     40

<210> SEQ ID NO 175
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 175
tgggggctga cggatccacm acacacccat tccacragtg ctgagtgaga acccaga      57

<210> SEQ ID NO 176
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tgggggctga cggatccags ccacacccat tccacractg ctgagtgaga acccaga      57

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gctcttcaga gatgggttag vgtatttatt gtcatcccac                          40

<210> SEQ ID NO 178
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
cttctgcagg taccattcma aataggtgtt tccccaactc ratacaatgc tctgactaga    60

<210> SEQ ID NO 179
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cttctgcagg taccattcma aataggtgtt tccgtaactc ratacaatgc tctgactaga    60

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cttctgcagg taccattcma aataggtgtt tccctgactc ratacaatgc tctgactaga    60

<210> SEQ ID NO 181
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 181
cttctgcagg taccattcma aataggtgtt tccccaactg tgtacaatgc tctgactaga        60

<210> SEQ ID NO 182
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cttctgcagg taccattcma aataggtgtt tccctaactg tctacaatgc tctgactaga        60

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cttctgcagg taccattcma aataggtgtt tccctcactg tgtacaatgc tctgactaga        60

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ttggtgctga tgttctgg                                                      18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
atcttcttgc tgttctgg                                                      18

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tgggtgctgc tgctctgg                                                      18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 187
gggctgcttg tgctctgg                                                 18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ggaatcttgt tgctctgg                                                 18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
rtrttsctgc tgctrtgg                                                 18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ggtctcctgt tgctctgt                                                 18

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
atatttctac tgctctgt                                                 18

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gtcataatrt ccagagga                                                 18

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 193
ctgagctgtg tattcct                                                    17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ctcarmttga ttttcct                                                    17

<210> SEQ ID NO 195
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tggrtcatst tcttcct                                                    17

<210> SEQ ID NO 196
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tksrtctttc tcttcct                                                    17

<210> SEQ ID NO 197
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tgtatcatsc tcttctt                                                    17

<210> SEQ ID NO 198
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tggrtctttc tcttttt                                                    17

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 199
ttaaacttgg gtttttct                                              18

<210> SEQ ID NO 200
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gkgctgytcy tctgcct                                               17

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ttaagtcttc tgtacctg                                              18

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tcagtaactg caggtgtcca                                            20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ttttaaaagg tgtccagtgt                                            20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
gcaacagcta caggtgtcca                                            20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 205
cagctacagr tgtccactcc                                                   20

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
atttccaagc tgtgtcctgt cc                                                22

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctcctgtcag gaactgcagg tgt                                               23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cagtggttac aggggtcaat tca                                               23

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ctgttsacag cchttcckgg t                                                 21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ctgatggcag ctgcccaaag t                                                 21

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 211
tttatcaagg tgtgcattgt                                         20

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tcactggatg gtgggaagat ggataca                                 27

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gacatttggg aaggactgac tctc                                    24

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214 caggggctc tcgcaggaga cgag                                     24

<210> SEQ ID NO 215
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
atcttcttgc tgttctgggt atctggaacc tgtggg                       36

<210> SEQ ID NO 216
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
ttggtgctga tgttctggat tcctgcttcc agcagt                       36

<210> SEQ ID NO 217
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 217
gtggacgttc ggccaaggga ccaaggtgga aatcaaac                    38

<210> SEQ ID NO 218
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218 tgtacactttt tggccagggg accaagctgg agatcaaac                  39

<210> SEQ ID NO 219
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
attactacta ctactacggt atggacgtct ggggccaagg gaccacggtc accgtctcct    60
cag                                                         63

<210> SEQ ID NO 220
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ttactcgctg cccaaccagc catggcc                               27

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gacagatggt gcagccacag t                                     21

<210> SEQ ID NO 222
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ttactgttta ccccctgtgac aaaagcc                              27

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 223
gaagaccgat gggcccttgg t                                              21

<210> SEQ ID NO 224
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(45)
<223> OTHER INFORMATION: a, c, g, or t

<400> SEQUENCE: 224
cttggtcccc tggccaaaag tgtacggata actatgatca ttmnnacagt aataaactgc    60
cacatc                                                               66

<210> SEQ ID NO 225
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 225
cttggtcccc tggccaaaag tgtacggata actatgatcm nnctgacagt aataaactgc    60
cacatc                                                               66

<210> SEQ ID NO 226
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 226
cttggtcccc tggccaaaag tgtacggata actatgmnna ttctgacagt aataaactgc    60
cacatc                                                               66

<210> SEQ ID NO 227
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 227
cttggtcccc tggccaaaag tgtacggata actmnnatca ttctgacagt aataaactgc    60
cacatc                                                               66
```

```
<210> SEQ ID NO 228
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 228
cttggtcccc tggccaaaag tgtacggata mnnatgatca ttctgacagt aataaactgc      60
cacatc                                                                66

<210> SEQ ID NO 229
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 229
cttggtcccc tggccaaaag tgtacggmnn actatgatca ttctgacagt aataaactgc      60
cacatc                                                                66

<210> SEQ ID NO 230
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 230
cttggtcccc tggccaaaag tgtamnnata actatgatca ttctgacagt aataaactgc      60
cacatc                                                                66

<210> SEQ ID NO 231
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 231
cttggtcccc tggccaaaag tmnncggata actatgatca ttctgacagt aataaactgc      60
cacatc                                                                66
```

<210> SEQ ID NO 232
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 232
cttggtcccc tggccaaamn ngtacggata actatgatca ttctgacagt aataaactgc    60
cacatc                                                                66

<210> SEQ ID NO 233
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (50)..(51)
<223> OTHER INFORMATION: a, c, g, or t

<400> SEQUENCE: 233
cgtggttcct tgcccccagt agtccatagc atcgtagtaa ccatcaacmn ntctcgcaca    60
gtaatacac                                                             69

<210> SEQ ID NO 234
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (47)..(48)
<223> OTHER INFORMATION: a, c, g, or t

<400> SEQUENCE: 234
cgtggttcct tgcccccagt agtccatagc atcgtagtaa ccatcmnncg gtctcgcaca    60
gtaatacac                                                             69

<210> SEQ ID NO 235
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(45)
<223> OTHER INFORMATION: a, c, g, or t

<400> SEQUENCE: 235
cgtggttcct tgcccccagt agtccatagc atcgtagtaa ccmnnaaccg gtctcgcaca    60
gtaatacac                                                             69

```
<210> SEQ ID NO 236
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 236
cgtggttcct tgcccccagt agtccatagc atcgtagtam nnatcaaccg gtctcgcaca      60
gtaatacac                                                              69

<210> SEQ ID NO 237
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 237
cgtggttcct tgcccccagt agtccatagc atcgtamnna ccatcaaccg gtctcgcaca      60
gtaatacac                                                              69

<210> SEQ ID NO 238
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 238
cgtggttcct tgcccccagt agtccatagc atcmnngtaa ccatcaaccg gtctcgcaca      60
gtaatacac                                                              69

<210> SEQ ID NO 239
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 239
cgtggttcct tgcccccagt agtccatagc mnngtagtaa ccatcaaccg gtctcgcaca      60
gtaatacac                                                              69
```

-continued

```
<210> SEQ ID NO 240
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 240
cgtggttcct tgcccccagt agtccatmnn atcgtagtaa ccatcaaccg gtctcgcaca       60
gtaatacac                                                              69

<210> SEQ ID NO 241
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 241
cgtggttcct tgcccccagt agtcmnnagc atcgtagtaa ccatcaaccg gtctcgcaca       60
gtaatacac                                                              69

<210> SEQ ID NO 242
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 242
cgtggttcct tgcccccagt amnncatagc atcgtagtaa ccatcaaccg gtctcgcaca       60
gtaatacac                                                              69

<210> SEQ ID NO 243
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 243
cgtggttcct tgcccccamn ngtccatagc atcgtagtaa ccatcaaccg gtctcgcaca       60
gtaatacac                                                              69
```

```
<210> SEQ ID NO 244
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(45)
<223> OTHER INFORMATION: a, c, g, or t

<400> SEQUENCE: 244
cttggtgccc tggccgaacg tccacggaac atgtgaacct tgmnngcagt aataaactcc    60
aacatc                                                               66

<210> SEQ ID NO 245
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 245
cttggtgccc tggccgaacg tccacggaac atgtgaaccm nnaaagcagt aataaactcc    60
aacatc                                                               66

<210> SEQ ID NO 246
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 246
cttggtgccc tggccgaacg tccacggaac atgtgamnnt tgaaagcagt aataaactcc    60
aacatc                                                               66

<210> SEQ ID NO 247
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 247
cttggtgccc tggccgaacg tccacggaac atgmnnacct tgaaagcagt aataaactcc    60
aacatc                                                               66
```

```
<210> SEQ ID NO 248
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 248
cttggtgccc tggccgaacg tccacggaac mnntgaacct tgaaagcagt aataaactcc    60
aacatc                                                               66

<210> SEQ ID NO 249
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 249
cttggtgccc tggccgaacg tccacggmnn atgtgaacct tgaaagcagt aataaactcc    60
aacatc                                                               66

<210> SEQ ID NO 250
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 250
cttggtgccc tggccgaacg tccamnnaac atgtgaacct tgaaagcagt aataaactcc    60
aacatc                                                               66

<210> SEQ ID NO 251
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 251
cttggtgccc tggccgaacg tmnncggaac atgtgaacct tgaaagcagt aataaactcc    60
aacatc                                                               66
```

```
<210> SEQ ID NO 252
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 252
cttggtgccc tggccgaamn nccacggaac atgtgaacct tgaaagcagt aataaactcc      60
aacatc                                                                66

<210> SEQ ID NO 253
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (56)..(57)
<223> OTHER INFORMATION: a, c, g, or t

<400> SEQUENCE: 253
cgtggttcct tgcccccagt agtccatagc atagtagggg ttaccatagt tagcmnntcg      60
agcacagtaa tacgt                                                      75

<210> SEQ ID NO 254
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (53)..(54)
<223> OTHER INFORMATION: a, c, g, or t

<400> SEQUENCE: 254
cgtggttcct tgcccccagt agtccatagc atagtagggg ttaccatagt tmnntcttcg      60
agcacagtaa tacgt                                                      75

<210> SEQ ID NO 255
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (50)..(51)
<223> OTHER INFORMATION: a, c, g, or t

<400> SEQUENCE: 255
cgtggttcct tgcccccagt agtccatagc atagtagggg ttaccatamn nagctcttcg      60
agcacagtaa tacgt                                                      75
```

<210> SEQ ID NO 256
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (47)..(48)
<223> OTHER INFORMATION: a, c, g, or t

<400> SEQUENCE: 256
cgtggttcct tgcccccagt agtccatagc atagtagggg ttaccmnngt tagctcttcg      60
agcacagtaa tacgt                                                       75

<210> SEQ ID NO 257
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(45)
<223> OTHER INFORMATION: a, c, g, or t

<400> SEQUENCE: 257
cgtggttcct tgcccccagt agtccatagc atagtagggg ttmnnatagt tagctcttcg      60
agcacagtaa tacgt                                                       75

<210> SEQ ID NO 258
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 258
cgtggttcct tgcccccagt agtccatagc atagtagggm nnaccatagt tagctcttcg      60
agcacagtaa tacgt                                                       75

<210> SEQ ID NO 259
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 259
cgtggttcct tgcccccagt agtccatagc atagtamnng ttaccatagt tagctcttcg      60
agcacagtaa tacgt                                                       75

<210> SEQ ID NO 260
<211> LENGTH: 75
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (35)..(36)
<223> OTHER INFORMATION: a, c, g, or t

<400> SEQUENCE: 260
cgtggttcct tgcccccagt agtccatagc atamnnggggg ttaccatagt tagctcttcg    60
agcacagtaa tacgt                                                      75

<210> SEQ ID NO 261
<211> LENGTH: 75
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (32)..(33)
<223> OTHER INFORMATION: a, c, g, or t

<400> SEQUENCE: 261
cgtggttcct tgcccccagt agtccatagc mnngtagggg ttaccatagt tagctcttcg     60
agcacagtaa tacgt                                                      75

<210> SEQ ID NO 262
<211> LENGTH: 75
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (29)..(30)
<223> OTHER INFORMATION: a, c, g, or t

<400> SEQUENCE: 262
cgtggttcct tgcccccagt agtccatmnn atagtagggg ttaccatagt tagctcttcg     60
agcacagtaa tacgt                                                      75

<210> SEQ ID NO 263
<211> LENGTH: 75
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (26)..(27)
<223> OTHER INFORMATION: a, c, g, or t

<400> SEQUENCE: 263
cgtggttcct tgcccccagt agtcmnnagc atagtagggg ttaccatagt tagctcttcg     60
agcacagtaa tacgt                                                      75

```
<210> SEQ ID NO 264
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 264
cgtggttcct tgcccccagt amnncatagc atagtagggg ttaccatagt tagctcttcg    60
agcacagtaa tacgt                                                    75

<210> SEQ ID NO 265
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 265
cgtggttcct tgcccccamn ngtccatagc atagtagggg ttaccatagt tagctcttcg    60
agcacagtaa tacgt                                                    75

<210> SEQ ID NO 266
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 266
gttcttttgg tttccgcwgt ttaacagact ctggctggam nngcagttga tggtggccct    60

<210> SEQ ID NO 267
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 267
gttcttttgg tttccgcwgt ttaacagact ctggctmnnc ttgcagttga tggtggccct    60

<210> SEQ ID NO 268
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (35)..(36)
<223> OTHER INFORMATION: a, c, g, or t

<400> SEQUENCE: 268
gttcttttgg tttccgcwgt ttaacagact ctgmnnggac ttgcagttga tggtggccct        60

<210> SEQ ID NO 269
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 269
gttcttttgg tttccgcwgt ttaacagact mnngctggac ttgcagttga tggtggccct        60

<210> SEQ ID NO 270
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 270
gttcttttgg tttccgcwgt ttaacagmnn ctggctggac ttgcagttga tggtggccct        60

<210> SEQ ID NO 271
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 271
gttcttttgg tttccgcwgt ttaamnnact ctggctggac ttgcagttga tggtggccct        60

<210> SEQ ID NO 272
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 272
gttcttttgg tttccgcwgt tmnncagact ctggctggac ttgcagttga tggtggccct        60
```

<210> SEQ ID NO 273
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 273 gttctttttgg tttccgcwmn ntaacagact ctggctggac ttgcagttga tggtggccct      60

<210> SEQ ID NO 274
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(45)
<223> OTHER INFORMATION: a, c, g, or t

<400> SEQUENCE: 274
tggtttctgc tggtaccaag ctaagtagtt cttttggttt ccmnngttta acagactctg      60
gct                                                                   63

<210> SEQ ID NO 275
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 275
tggtttctgc tggtaccaag ctaagtagtt cttttggttm nngcwgttta acagactctg      60
gct                                                                   63

<210> SEQ ID NO 276
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 276
tggtttctgc tggtaccaag ctaagtagtt cttttgmnnt ccgcwgttta acagactctg      60
gct                                                                   63

<210> SEQ ID NO 277
<211> LENGTH: 63
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 277
tggtttctgc tggtaccaag ctaagtagtt cttmnngttt ccgcwgttta acagactctg      60
gct                                                                   63

<210> SEQ ID NO 278
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 278
tggtttctgc tggtaccaag ctaagtagtt mnnttggttt ccgcwgttta acagactctg      60
gct                                                                   63

<210> SEQ ID NO 279
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 279
tggtttctgc tggtaccaag ctaagtamnn cttttggttt ccgcwgttta acagactctg      60
gct                                                                   63

<210> SEQ ID NO 280
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 280
tggtttctgc tggtaccaag ctaamnngtt cttttggttt ccgcwgttta acagactctg      60
gct                                                                   63

<210> SEQ ID NO 281
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (23)..(24)
<223> OTHER INFORMATION: a, c, g, or t

<400> SEQUENCE: 281
tggtttctgc tggtaccaag cmnngtagtt cttttggttt ccgcwgttta acagactctg      60
gct                                                                    63

<210> SEQ ID NO 282
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 282
tggtttctgc tggtaccamn ntaagtagtt cttttggttt ccgcwgttta acagactctg      60
gct                                                                    63

<210> SEQ ID NO 283
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 283
gaatcggtca gggaccccgg attccctggt agatgcmnng taaatgagca gcttagg         57

<210> SEQ ID NO 284
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 284
gaatcggtca gggaccccgg attccctggt agamnncccg taaatgagca gcttagg         57

<210> SEQ ID NO 285
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t
```

<400> SEQUENCE: 285
gaatcggtca gggaccccgg attccctggt mnntgccccg taaatgagca gcttagg    57

<210> SEQ ID NO 286
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 286
gaatcggtca gggaccccgg attccctmnn agatgccccg taaatgagca gcttagg    57

<210> SEQ ID NO 287
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 287
gaatcggtca gggaccccgg attcmnnggt agatgccccg taaatgagca gcttagg    57

<210> SEQ ID NO 288
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 288
gaatcggtca gggaccccgg amnncctggt agatgccccg taaatgagca gcttagg    57

<210> SEQ ID NO 289
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 289
gaatcggtca gggaccccmn nttccctggt agatgccccg taaatgagca gcttagg    57

<210> SEQ ID NO 290
<211> LENGTH: 51
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 290
tggagcctgg cggacccagc tcatccaata mnnactaaag gtgaatccag a            51

<210> SEQ ID NO 291
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 291
tggagcctgg cggacccagc tcatccamnn tctactaaag gtgaatccag a            51

<210> SEQ ID NO 292
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 292
tggagcctgg cggacccagc tcatmnnata tctactaaag gtgaatccag a            51

<210> SEQ ID NO 293
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 293
tggagcctgg cggacccagc tmnnccaata tctactaaag gtgaatccag a            51

<210> SEQ ID NO 294
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 294
tggagcctgg cggacccamn ncatccaata tctactaaag gtgaatccag a            51
```

<210> SEQ ID NO 295
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(45)
<223> OTHER INFORMATION: a, c, g, or t

<400> SEQUENCE: 295
tagagatggc gtatagttta tcgtactgct atctggattt atmnngccaa yccactccag      60
cccttc                                                                67

<210> SEQ ID NO 296
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 296
tagagatggc gtatagttta tcgtactgct atctggattm nnttcgccaa yccactccag      60
cccttc                                                                67

<210> SEQ ID NO 297
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 297
tagagatggc gtatagttta tcgtactgct atctggmnnt atttcgccaa yccactccag      60
cccttc                                                                67

<210> SEQ ID NO 298
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 298
tagagatggc gtatagttta tcgtactgct atcmnnattt atttcgccaa yccactccag      60
cccttc                                                                67

```
<210> SEQ ID NO 299
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 299
tagagatggc gtatagttta tcgtactgct mnntggattt atttcgccaa yccactccag      60
cccttc                                                                 67

<210> SEQ ID NO 300
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 300
tagagatggc gtatagttta tcgtactmnn atctggattt atttcgccaa yccactccag      60
cccttc                                                                 67

<210> SEQ ID NO 301
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 301
tagagatggc gtatagttta tcgtmnngct atctggattt atttcgccaa yccactccag      60
cccttc                                                                 67

<210> SEQ ID NO 302
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 302
tagagatggc gtatagttta tmnnactgct atctggattt atttcgccaa yccactccag      60
cccttc                                                                 67
```

```
<210> SEQ ID NO 303
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 303
tagagatggc gtatagttmn ncgtactgct atctggattt atttcgccaa yccactccag    60
cccttc                                                               67

<210> SEQ ID NO 304
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (48)..(49)
<223> OTHER INFORMATION: a, c, g, or t

<400> SEQUENCE: 304
cgttgtctct ggagatgrtg aatytatcct ttagagatgg cgtatamnnt atcgtactgc    60
tatctgg                                                              67

<210> SEQ ID NO 305
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (45)..(46)
<223> OTHER INFORMATION: a, c, g, or t

<400> SEQUENCE: 305
cgttgtctct ggagatgrtg aatytatcct ttagagatgg cgtmnngttt atcgtactgc    60
tatctgg                                                              67

<210> SEQ ID NO 306
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (42)..(43)
<223> OTHER INFORMATION: a, c, g, or t

<400> SEQUENCE: 306
cgttgtctct ggagatgrtg aatytatcct ttagagatgg mnnatagttt atcgtactgc    60
tatctgg                                                              67
```

-continued

```
<210> SEQ ID NO 307
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (39)..(40)
<223> OTHER INFORMATION: a, c, g, or t

<400> SEQUENCE: 307
cgttgtctct ggagatgrtg aatytatcct ttagagamnn cgtatagttt atcgtactgc    60
tatctgg                                                              67

<210> SEQ ID NO 308
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (36)..(37)
<223> OTHER INFORMATION: a, c, g, or t

<400> SEQUENCE: 308
cgttgtctct ggagatgrtg aatytatcct ttagmnntgg cgtatagttt atcgtactgc    60
tatctgg                                                              67

<210> SEQ ID NO 309
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(34)
<223> OTHER INFORMATION: a, c, g, or t

<400> SEQUENCE: 309
cgttgtctct ggagatgrtg aatytatcct tmnnagatgg cgtatagttt atcgtactgc    60
tatctgg                                                              67

<210> SEQ ID NO 310
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(31)
<223> OTHER INFORMATION: a, c, g, or t

<400> SEQUENCE: 310
cgttgtctct ggagatgrtg aatytatcmn ntagagatgg cgtatagttt atcgtactgc    60
tatctgg                                                              67
```

```
<210> SEQ ID NO 311
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(28)
<223> OTHER INFORMATION: a, c, g, or t

<400> SEQUENCE: 311
cgttgtctct ggagatgrtg aatytmnnct ttagagatgg cgtatagttt atcgtactgc    60
tatctgg                                                              67

<210> SEQ ID NO 312
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 312
ataggtgttt ccattactat gtacaatgct ctgactagam nngcaggaga tggaggcc      58

<210> SEQ ID NO 313
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 313
ataggtgttt ccattactat gtacaatgct ctgactmnnc ctgcaggaga tggaggcc      58

<210> SEQ ID NO 314
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 314
ataggtgttt ccattactat gtacaatgct ctgmnnagac ctgcaggaga tggaggcc      58

<210> SEQ ID NO 315
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (32)..(33)
<223> OTHER INFORMATION: a, c, g, or t

<400> SEQUENCE: 315
ataggtgttt ccattactat gtacaatgct mnnactagac ctgcaggaga tggaggcc        58

<210> SEQ ID NO 316
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 316
ataggtgttt ccattactat gtacaatmnn ctgactagac ctgcaggaga tggaggcc        58

<210> SEQ ID NO 317
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 317
ataggtgttt ccattactat gtacmnngct ctgactagac ctgcaggaga tggaggcc        58

<210> SEQ ID NO 318
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 318
ataggtgttt ccattactat gmnnaatgct ctgactagac ctgcaggaga tggaggcc        58

<210> SEQ ID NO 319
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 319
ataggtgttt ccattactmn ntacaatgct ctgactagac ctgcaggaga tggaggcc        58
```

```
<210> SEQ ID NO 320
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 320
tggcttctgc aggtaccatt ccaaataggt gtttccattm nnatgtacaa tgctctgact      60

<210> SEQ ID NO 321
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 321
tggcttctgc aggtaccatt ccaaataggt gtttccmnna ctatgtacaa tgctctgact      60

<210> SEQ ID NO 322
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 322
tggcttctgc aggtaccatt ccaaataggt gttmnnatta ctatgtacaa tgctctgact      60

<210> SEQ ID NO 323
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 323
tggcttctgc aggtaccatt ccaaataggt mnntccatta ctatgtacaa tgctctgact      60

<210> SEQ ID NO 324
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t
```

```
<400> SEQUENCE: 324
tggcttctgc aggtaccatt ccaaatamnn gtttccatta ctatgtacaa tgctctgact      60

<210> SEQ ID NO 325
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 325
tggcttctgc aggtaccatt ccaamnnggt gtttccatta ctatgtacaa tgctctgact      60

<210> SEQ ID NO 326
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 326
tggcttctgc aggtaccatt cmnnataggt gtttccatta ctatgtacaa tgctctgact      60

<210> SEQ ID NO 327
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 327
tggcttctgc aggtaccamn ncaaataggt gtttccatta ctatgtacaa tgctctgact      60

<210> SEQ ID NO 328
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 328
gaacctgtct gggactccag aaaaccggtt ggaaacmnna tagatcagga gctgtgg         57

<210> SEQ ID NO 329
<211> LENGTH: 57
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 329
gaacctgtct gggactccag aaaaccggtt ggamnnttta tagatcagga gctgtgg      57

<210> SEQ ID NO 330
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 330
gaacctgtct gggactccag aaaaccggtt mnnaacttta tagatcagga gctgtgg      57

<210> SEQ ID NO 331
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 331
gaacctgtct gggactccag aaaaccgmnn ggaaacttta tagatcagga gctgtgg      57

<210> SEQ ID NO 332
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 332
gaacctgtct gggactccag aaaamnngtt ggaaacttta tagatcagga gctgtgg      57

<210> SEQ ID NO 333
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 333
gaacctgtct gggactccag amnnccggtt ggaaacttta tagatcagga gctgtgg      57
```

<210> SEQ ID NO 334
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 334
gaacctgtct gggactccmn naaaccggtt ggaaacttta tagatcagga gctgtgg    57

<210> SEQ ID NO 335
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 335
tgggggctga cggatccagc ccacacccat tccagamnng ctgagtgaga acccaga    57

<210> SEQ ID NO 336
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 336
tgggggctga cggatccagc ccacacccat tccmnnagtg ctgagtgaga acccaga    57

<210> SEQ ID NO 337
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 337
tgggggctga cggatccagc ccacacccat mnnagaagtg ctgagtgaga acccaga    57

<210> SEQ ID NO 338
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

```
<400> SEQUENCE: 338
tgggggctga cggatccagc ccacaccmnn tccagaagtg ctgagtgaga acccaga      57

<210> SEQ ID NO 339
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 339
tgggggctga cggatccagc ccacmnncat tccagaagtg ctgagtgaga acccaga      57

<210> SEQ ID NO 340
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 340
tgggggctga cggatccagc cmnnacccat tccagaagtg ctgagtgaga acccaga      57

<210> SEQ ID NO 341
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 341
tgggggctga cggatccamn ncacacccat tccagaagtg ctgagtgaga acccaga      57

<210> SEQ ID NO 342
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 342
cagagatggg ttgtagtatt tattgtcatc ccaccaaatm nntgcaagcc actccagggc   60

<210> SEQ ID NO 343
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 343
cagagatggg ttgtagtatt tattgtcatc ccaccamnng tctgcaagcc actccagggc      60

<210> SEQ ID NO 344
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t

<400> SEQUENCE: 344
cagagatggg ttgtagtatt tattgtcatc ccamnnaatg tctgcaagcc actccagggc      60

<210> SEQ ID NO 345
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 345
cagagatggg ttgtagtatt tattgtcatc mnnccaaatg tctgcaagcc actccagggc      60

<210> SEQ ID NO 346
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 346
cagagatggg ttgtagtatt tattgtcmnn ccaccaaatg tctgcaagcc actccagggc      60

<210> SEQ ID NO 347
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 347
cagagatggg ttgtagtatt tattmnnatc ccaccaaatg tctgcaagcc actccagggc      60
```

```
<210> SEQ ID NO 348
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 348
cagagatggg ttgtagtatt tmnngtcatc ccaccaaatg tctgcaagcc actccagggc    60

<210> SEQ ID NO 349
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 349
cagagatggg ttgtagtamn nattgtcatc ccaccaaatg tctgcaagcc actccagggc    60

<210> SEQ ID NO 350
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(42)
<223> OTHER INFORMATION: a, c, g, or t

<400> SEQUENCE: 350
cttggagatg gtgagcctgc tcttcagaga tgggttgtam nntttattgt catcccacca    60

<210> SEQ ID NO 351
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, g, or t

<400> SEQUENCE: 351
cttggagatg gtgagcctgc tcttcagaga tgggttmnng tatttattgt catcccacca    60

<210> SEQ ID NO 352
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, g, or t
```

<400> SEQUENCE: 352
cttggagatg gtgagcctgc tcttcagaga tggmnngtag tatttattgt catcccacca    60

<210> SEQ ID NO 353
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(33)
<223> OTHER INFORMATION: a, c, g, or t

<400> SEQUENCE: 353
cttggagatg gtgagcctgc tcttcagaga mnngttgtag tatttattgt catcccacca    60

<210> SEQ ID NO 354
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, g, or t

<400> SEQUENCE: 354
cttggagatg gtgagcctgc tcttcagmnn tgggttgtag tatttattgt catcccacca    60

<210> SEQ ID NO 355
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, g, or t

<400> SEQUENCE: 355
cttggagatg gtgagcctgc tcttmnnaga tgggttgtag tatttattgt catcccacca    60

<210> SEQ ID NO 356
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, or t

<400> SEQUENCE: 356
cttggagatg gtgagcctgc tmnncagaga tgggttgtag tatttattgt catcccacca    60

<210> SEQ ID NO 357
<211> LENGTH: 60
<212> TYPE: DNA
<213> ORGANISM: Artificial Sequence

```
-continued

<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, or t

<400> SEQUENCE: 357
cttggagatg gtgagcctmn ncttcagaga tgggttgtag tatttattgt catcccacca        60

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      antibody mutation

<400> SEQUENCE: 358

Phe Gln Ser Ser His Phe Pro Trp Thr
1               5
```